United States Patent
Wang et al.

(10) Patent No.: US 10,194,860 B2
(45) Date of Patent: Feb. 5, 2019

(54) VIRTUAL IMAGE DISPLAY SYSTEM

(71) Applicant: Industrial Technology Research Institute, Hsinchu (TW)

(72) Inventors: Chy-Lin Wang, Taipei (TW); Kuo-Tung Tiao, Hsinchu County (TW); Tian-Yuan Chen, Hsinchu (TW); Lung-Pin Chung, Miaoli County (TW); Chun-Chuan Lin, Hsinchu (TW); Jyh-Chern Chen, New Taipei (TW); Chi-Shen Chang, Hsinchu County (TW); Ching-Chieh Yang, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 218 days.

(21) Appl. No.: 15/173,571

(22) Filed: Jun. 3, 2016

(65) Prior Publication Data

US 2016/0278695 A1 Sep. 29, 2016

Related U.S. Application Data

(63) Continuation-in-part of application No. 14/291,015, filed on May 30, 2014, now Pat. No. 10,073,269.

(30) Foreign Application Priority Data

Sep. 11, 2013 (TW) .............................. 102132852 A

(51) Int. Cl.
*G02B 27/14* (2006.01)
*A61B 5/00* (2006.01)
(Continued)

(52) U.S. Cl.
CPC ............ *A61B 5/489* (2013.01); *A61B 5/0086* (2013.01); *A61B 5/745* (2013.01); *A61B 5/7445* (2013.01);
(Continued)

(58) Field of Classification Search
CPC .... G02B 27/017; G02B 27/0176; G02B 5/30; G02B 2027/0127; G02B 6/00; G02B 3/14; G02B 27/0149; A61B 34/25
See application file for complete search history.

(56) References Cited

U.S. PATENT DOCUMENTS

| 5,383,053 A | 1/1995 | Hegg et al. |
| 5,491,510 A | 2/1996 | Gove |

(Continued)

FOREIGN PATENT DOCUMENTS

| CN | 1115152 | 1/1996 |
| TW | 200630661 | 9/2006 |

(Continued)

OTHER PUBLICATIONS

"Office Action of China Counterpart Application", dated Apr. 26, 2016, p. 1-p. 11, in which the listed references were cited.

(Continued)

*Primary Examiner* — Alicia M Harrington
(74) *Attorney, Agent, or Firm* — JCIPRNET

(57) ABSTRACT

A virtual image display system adapted for venipuncture applications is provided. The virtual image display system includes at least one infrared light source, at least one image sensing module, and at least one virtual image display module. The at least one infrared light source is configured to emit at least one infrared light to a tissue having a vein. The at least one image sensing module is configured to receive the infrared light from the tissue so as to sense an image of the vein. The at least one virtual image display module is disposed in front of at least one eye of a user. The at least one virtual image display module includes an image display unit configured to show an image of the vein to the at least one eye of the user.

19 Claims, 50 Drawing Sheets

(51) Int. Cl.
| | |
|---|---|
| G02B 27/01 | (2006.01) |
| G02B 27/28 | (2006.01) |
| G02B 23/24 | (2006.01) |
| H04N 5/225 | (2006.01) |
| H04N 5/33 | (2006.01) |
| H04N 13/204 | (2018.01) |
| G02B 5/30 | (2006.01) |
| A61B 34/00 | (2016.01) |
| A61B 90/50 | (2016.01) |
| G02B 3/14 | (2006.01) |
| G02B 6/00 | (2006.01) |
| A61B 90/00 | (2016.01) |
| A61B 34/10 | (2016.01) |

(52) U.S. Cl.
CPC .......... *A61B 34/25* (2016.02); *A61B 90/50* (2016.02); *G02B 5/30* (2013.01); *G02B 23/2461* (2013.01); *G02B 23/2484* (2013.01); *G02B 27/017* (2013.01); *G02B 27/0172* (2013.01); *G02B 27/0176* (2013.01); *G02B 27/286* (2013.01); *H04N 5/2256* (2013.01); *H04N 5/2257* (2013.01); *H04N 5/33* (2013.01); *H04N 13/204* (2018.05); *A61B 2034/107* (2016.02); *A61B 2090/364* (2016.02); *A61B 2090/368* (2016.02); *A61B 2090/372* (2016.02); *A61B 2090/502* (2016.02); *G02B 3/14* (2013.01); *G02B 6/00* (2013.01); *G02B 27/0149* (2013.01); *G02B 2027/014* (2013.01); *G02B 2027/0118* (2013.01); *G02B 2027/0127* (2013.01); *G02B 2027/0138* (2013.01); *G02B 2027/0178* (2013.01)

(56) References Cited

U.S. PATENT DOCUMENTS

| | | | |
|---|---|---|---|
| 5,546,227 A | 8/1996 | Yasugaki et al. | |
| 5,808,801 A | 9/1998 | Nakayama et al. | |
| 5,886,822 A | 3/1999 | Spitzer | |
| 5,954,642 A | 9/1999 | Johnson et al. | |
| 6,011,653 A | 1/2000 | Karasawa | |
| 6,050,717 A | 4/2000 | Kosugi et al. | |
| 6,172,657 B1 | 1/2001 | Kamakura et al. | |
| 6,522,474 B2 | 2/2003 | Cobb et al. | |
| 6,937,400 B2 | 8/2005 | Olsson | |
| 6,947,219 B1 | 9/2005 | Ou | |
| 7,133,207 B2 | 11/2006 | Travers | |
| 7,369,317 B2 | 5/2008 | Li et al. | |
| 8,040,292 B2 | 10/2011 | Ronzani et al. | |
| 8,259,239 B2 | 9/2012 | Hua | |
| 9,004,683 B2 | 4/2015 | Caldeira et al. | |
| 2002/0024675 A1 | 2/2002 | Foxlin | |
| 2004/0263614 A1 | 12/2004 | Banju et al. | |
| 2006/0198027 A1 | 9/2006 | Li et al. | |
| 2009/0303212 A1 | 12/2009 | Akutsu et al. | |
| 2010/0113940 A1* | 5/2010 | Sen | A61B 5/0062 600/476 |
| 2010/0208054 A1* | 8/2010 | Farr | A61B 1/00103 348/80 |
| 2012/0206817 A1 | 8/2012 | Totani et al. | |
| 2012/0326948 A1 | 12/2012 | Crocco et al. | |
| 2013/0088415 A1 | 4/2013 | Totani | |
| 2013/0113973 A1 | 5/2013 | Miao | |
| 2013/0169925 A1 | 7/2013 | Caldeira et al. | |
| 2013/0170022 A1 | 7/2013 | Caldeira et al. | |
| 2014/0139405 A1* | 5/2014 | Ribble | G06F 19/3406 345/8 |

FOREIGN PATENT DOCUMENTS

| | | |
|---|---|---|
| TW | 200632409 | 9/2006 |
| TW | 200835321 | 8/2008 |
| TW | I319495 | 1/2010 |
| TW | I370277 | 8/2012 |
| TW | 201403128 | 1/2014 |

OTHER PUBLICATIONS

Hideya Takahashi, et al., "Stereoscopic see-through retinal projection head-mounted display," SPIE-IS&T, Feb. 29, 2008, vol. 6803, pp. 68031N-1-68031N-8.

Dewen Cheng, et al., "Design of a wide-angle, lightweight head-mounted display using free-form optics tiling," Optics Letters, Jun. 1, 2011, vol. 36, No. 11, pp. 2098-pp. 2100.

Dewen Cheng, et al., "Design of an optical see-through head-mounted display with a low f-number and large field of view using a freeform prism," Applied Optics, May 10, 2009, vol. 48, No. 14, pp. 2655-pp. 2668.

James P. McGuire, Jr., "Next-generation head-mounted display," Proc. of SPIE, Feb. 12, 2010, vol. 7618, pp. 761804-1-pp. 761804-8.

Takahisa Ando, et al., "Head Mounted Display using holographic optical element," SPIE, Mar. 18, 1998, vol. 3293, pp. 183-pp. 189.

Scott A. Nelson, et al., "Arthroscopic knee surgery using the Advanced Flat Panel high resolution color head-mounted display," SPIE, Jun. 18, 1997, vol. 3058, pp. 170-pp. 177.

"Office Action of China Counterpart Application", dated Dec. 20, 2016, p. 1-p. 16, in which the listed reference as cited.

\* cited by examiner

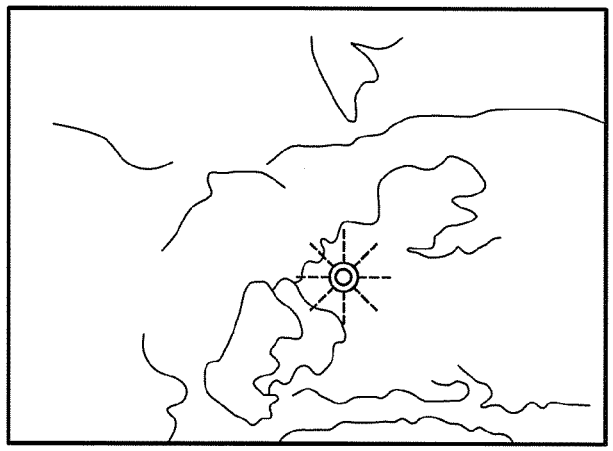
FIG. 5A
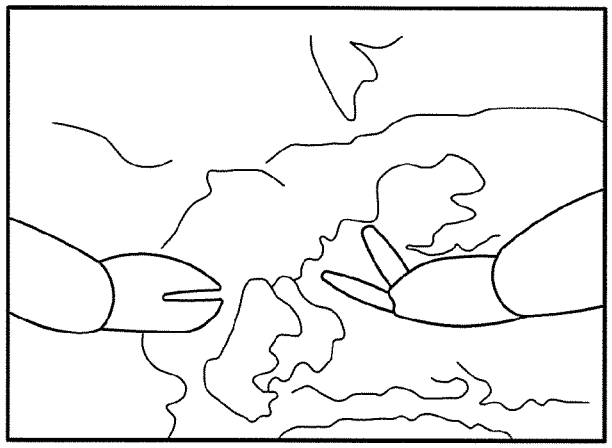
FIG. 5B
```
Temperature 37 C
Pulse 80
Pressure 70,110
Blood oxygen 80%
```
FIG. 5C

VIRTUAL IMAGE DISPLAY SYSTEM

CROSS-REFERENCE TO RELATED APPLICATION

This application is a continuation-in-part application of and claims the priority benefit of a prior application Ser. No. 14/291,015, filed on May 30, 2014, now pending. The prior application Ser. No. 14/291,015 claims the priority benefit of Taiwan application serial no. 102132852, filed on Sep. 11, 2013. The entirety of each of the above-mentioned patent applications is hereby incorporated by reference herein and made a part of this specification.

BACKGROUND

Technical Field

The technical field relates to a visual image display apparatus.

Background

The imaging system plays an important role in various medical applications and non-medical applications. For instance, when the imaging system is applied in endoscopy, an endoscopic imaging system allows the surgeon to examine the internal organs of the body or to perform an endoscopic surgery with minimally invasive means. In this way, larger wounds of traditional surgery can be avoided, thus retaining the integrity of organs and muscle tissue around the surgical incision. Moreover, the need for blood transfusion is reduced, the occurrence of complications such as tissue adhesion, stiffness, and bacterial infection are reduced, unsightly surgical scars are prevented, and hospital stay and recovery time are significantly shortened.

Generally, in an endoscopic surgery, the surgeon needs to rely on a monitor to observe the surgical conditions within the body to adjust the amount of displacement of surgical devices and correct the angle thereof. However, in the current endoscopic surgery, since the monitor is fixed at a distance, the surgeon needs to observe the monitor at a fixed viewing angle for long periods of time, causing not only fatigue of the eyes, the neck, and the shoulders, but also causing difficulty in controlling the sense of direction of the surgical devices to less-experienced surgeons. As a result, during surgery, the sense of direction needs to be constantly corrected and adjusted, resulting in lengthened operating time and increased surgical risk.

SUMMARY

A virtual image display system of an embodiment of the disclosure is adapted for venipuncture applications. The virtual image display system comprises at least one infrared light source, at least one image sensing module, and at least one virtual image display module. The at least one infrared light source is configured to emit at least one infrared light to a tissue having a vein. The at least one image sensing module is configured to receive the infrared light from the tissue so as to sense an image of the vein. The at least one virtual image display module is disposed in front of at least one eye of a user. The at least one virtual image display module comprises an image display unit configured to show an image of the vein to the at least one eye of the user.

The virtual image display system of an embodiment of the disclosure is adapted for medical surgical applications. With the virtual image display system, a surgical device is operated. The virtual image display system includes at least one virtual image display module and the virtual image display module is disposed in front of at least one eye of a user. The virtual image display module includes an image display unit and a beam splitting unit. The image display unit provides an image beam, wherein the image beam includes at least one type of surgical information. The beam splitting unit is disposed on the transmission path of the image beam and an object beam from an environment object, the beam splitting unit causes at least a part of the object beam to be transmitted to the eye, and the beam splitting unit causes at least a part of the image beam to be transmitted to the eye to display a virtual image.

The virtual image display system of an embodiment of the disclosure includes at least one virtual image display module and an ambient light adjustment unit. The virtual image display system is disposed in front of at least one eye of a user. The virtual image display module includes an image display unit and a beam splitting unit. The image display unit provides an image beam. The beam splitting unit is disposed on the transmission path of the image beam and an object beam from an environment object, the beam splitting unit causes at least a part of the object beam to be transmitted to the eye and at least a part of the image beam to be transmitted to the eye to display a virtual image. The ambient light adjustment unit is located on the transmission path of the object beam for adjusting the ratio of the brightness of at least a part of the object beam to the brightness of at least a part of the image beam.

Several exemplary embodiments accompanied with figures are described in detail below to further describe the disclosure in details.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

FIG. 5A to FIG. 5C are schematic diagrams of different image frames of the virtual image display system of FIG. 1.

DETAILED DESCRIPTION OF DISCLOSED EMBODIMENTS

Figure 1:
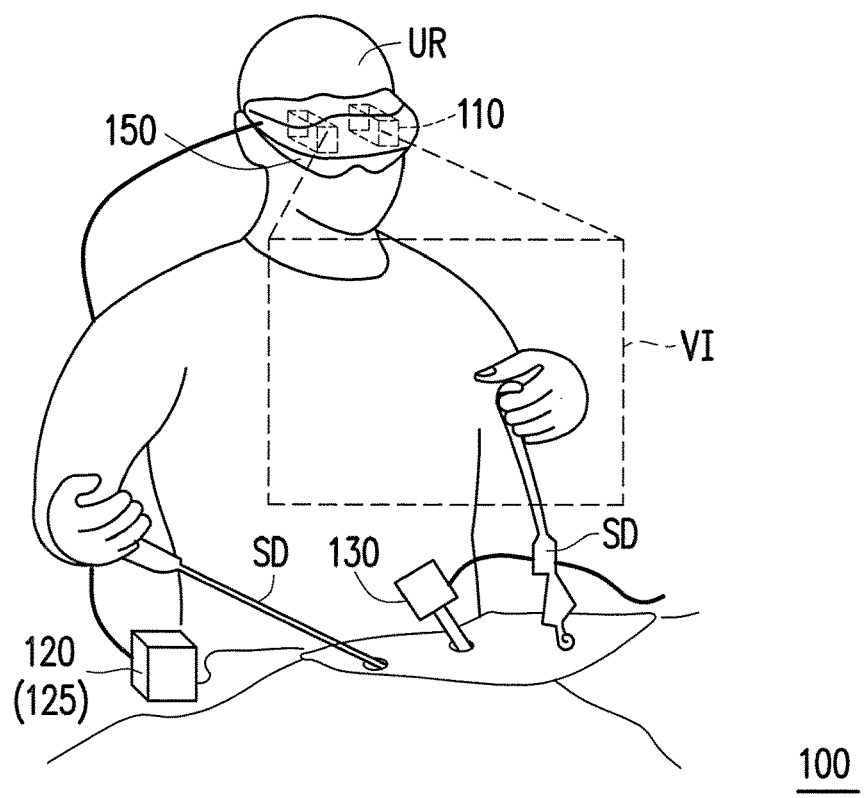
FIG. 1 is a schematic diagram of the architecture of a virtual image display system of an embodiment of the disclosure applied in a medical surgery.
Figure 2:
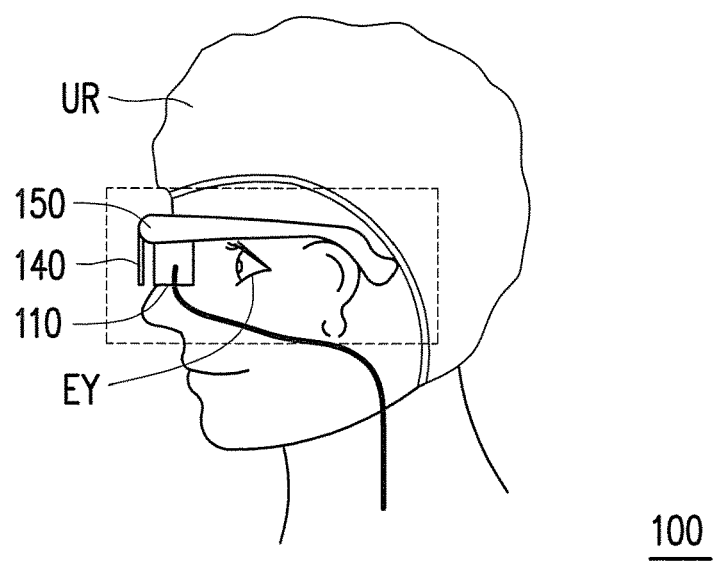
FIG. 2 is a schematic diagram of the virtual image display system of FIG. 1 worn on the head of a user.

FIG. 1 is a schematic diagram of the architecture of a virtual image display system of an embodiment of the disclosure applied in a medical surgery. FIG. 2 is a schematic diagram of the virtual image display system of FIG. 1 worn on the head of a user. Referring to FIG. 1 and FIG. 2, in the present embodiment, a virtual image display system 100 is adapted for medical surgical applications. With the virtual image display system 100, surgical devices SD are operated, so as to allow the surgeon or a user UR to examine the internal organs of a body or perform an endoscopic surgery with minimally invasive means. Specifically, in the present embodiment, the virtual image display system 100 includes a virtual image display module 110, a control storage module 120, an imaging unit 130, an ambient light adjustment unit 140, and a frame 150. More specifically, as shown in FIG. 1, the control storage module 120 further includes a casing 125, and the casing 125 can be disposed on the user UR such that the user UR can move conveniently. In the present embodiment, the casing 125 is, for instance, made of an antibacterial material or a sterilizing material.

Moreover, as shown in FIG. 2, the virtual image display module 110 and the ambient light adjustment unit 140 are disposed on the frame 150 so as to be disposed in front of at least one eye EY of the user UR.

Figure 3:
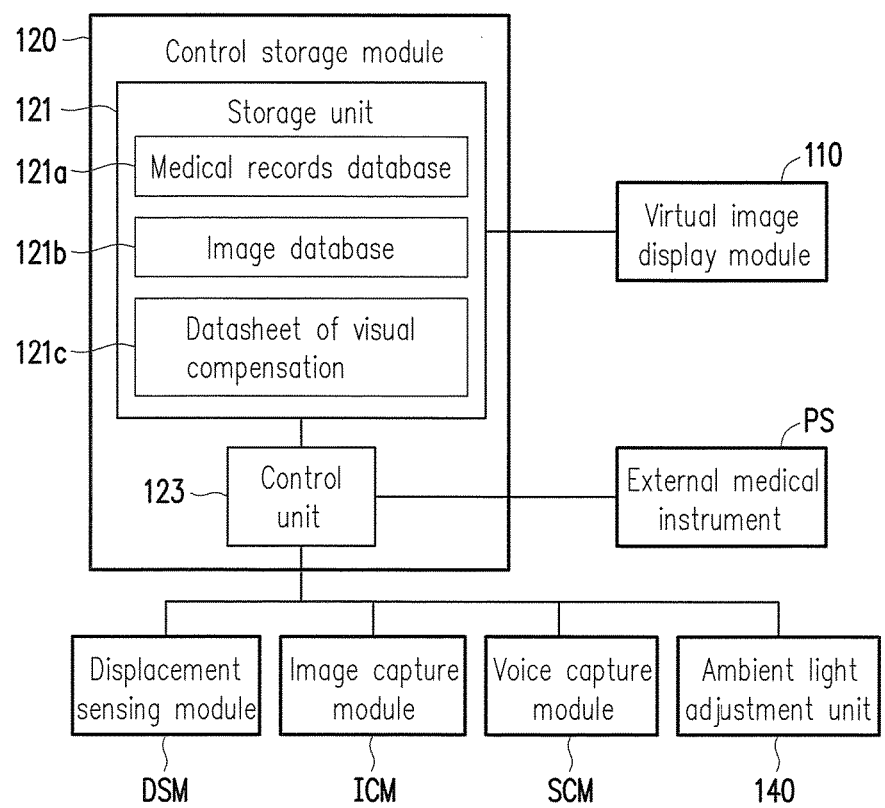
FIG. 3 is a schematic diagram of the architecture of the control storage module of FIG. 1.

Furthermore, referring again to FIG. 1, in the present embodiment, the imaging unit 130 is electrically connected to the virtual image display module 110 and the control storage module 120 for obtaining and transmitting image information to the virtual image display module 110 to obtain a tissue image of a patient. For instance, the imaging unit 130 can be inserted into the body cavity of a patient through a cannula inserted into the skin of the patient. The surgeon or the user UR can move the imaging unit 130 back and forth horizontally through the surgical devices SD such that the imaging unit 130 can capture a tissue image of the patient from different angles and transmit the tissue image to the virtual image display module 110 through the control storage module 120 such that the virtual image display module 110 can form a virtual image VI in front of the eye of the user UR. Moreover, the tissue image of the patient can also be stored in the control storage module 120. FIG. 3 is used to further explain the internal architecture of the control storage module 120 below.

FIG. 3 is a schematic diagram of the architecture of the control storage module of FIG. 1. Referring to FIG. 1 and FIG. 3, in the present embodiment, the control storage module 120 includes a storage unit 121 and a control unit 123 and the casing 125 of the control storage module 120 (as shown in FIG. 1) has an accommodating space for accommodating the storage unit 121 and the control unit 123. Specifically, the storage unit 121 stores relevant surgical information. For instance, in the present embodiment, the storage unit 121 includes an image database 121*b* and a medical records database 121*a*. More specifically, the image database 121*b* can, for instance, store the tissue image or an organ image of the patient obtained by the imaging unit 130. Moreover, the user UR can also input and store medical records of the patient such as name, age, diagnostic data, surgical site, surgical approach, and special considerations such as drug allergy, pacemaker, and infectious disease in the medical records database 121*a* beforehand.

Moreover, specifically, in the present embodiment, the control storage module 120 and the virtual image display module 110 are electrically connected, and the control unit 123 controls the storage unit 121 to adjust the output of the surgical information and transmits relevant surgical information to the image frame of the virtual image display module 110 such that the user UR can make the virtual image display module 110 display the needed surgical information according to actual need.

For instance, the control unit 123 can control the image output of the image database 121*b* of the storage unit 121 and control the display of the tissue image of the patient or replay the image during the surgery according to the actual need of the user UR. Alternatively, the control unit 123 can control the output of medical information of the medical records database 121*a* of the storage unit 121 such that the user UR can obtain the needed medical information according to actual need. Moreover, the control unit 123 can further be connected to at least one external medical instrument PS and receive parameter information generated by at least one external medical instrument PS. For instance, the control unit 123 can be connected to the surgical devices SD (as shown in FIG. 1) to obtain an operation control parameter of the surgical devices SD such that the user UR can more precisely control the positioning of the surgical devices SD. Alternatively, the control unit 123 can be connected to a physiological signal monitor and accordingly obtain physiological signals (information such as body temperature, heart rate, blood pressure, and blood oxygen level) of the patient during surgery to control the condition of the patient immediately.

Figure 4:
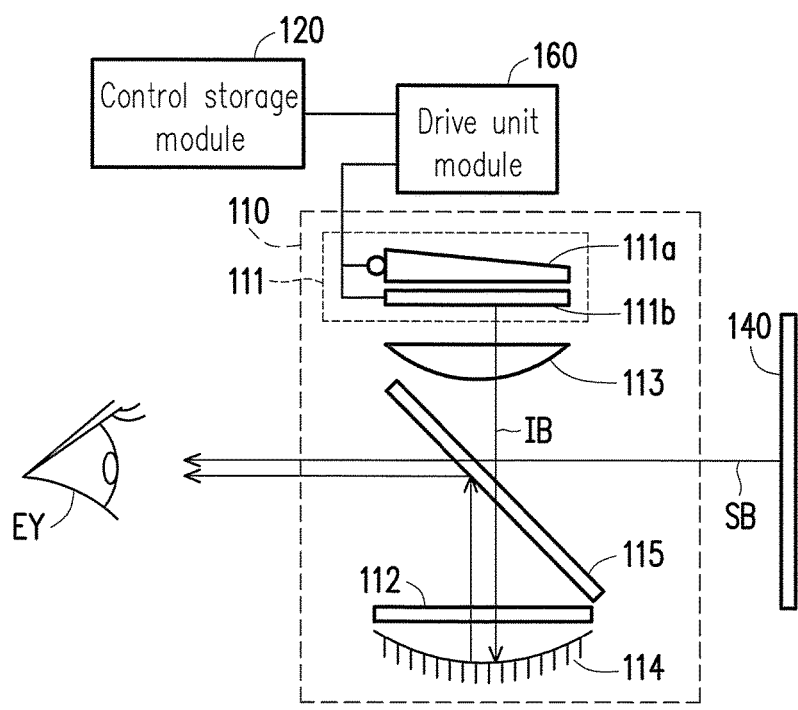
FIG. 4 is a schematic diagram of the architecture of the virtual image display system of FIG. 1.

FIG. 4 to FIG. 5C are used to further explain the structural design and the imaging principle of the virtual image display system 100 below.

FIG. 4 is a schematic diagram of the architecture of the virtual image display system of FIG. 1. FIG. 5A to FIG. 5C are schematic diagrams of different image frames of the virtual image display system of FIG. 1. Referring to FIG. 4, in the present embodiment, the virtual image display system 100 further includes a drive unit module 160 and the virtual image display module 110 includes an image display unit 111, a beam splitting unit 115, a wave plate 112, and a reflection unit 114. Specifically, in the present embodiment, the beam splitting unit 115 can be a polarization beam splitter (PBS), a wire grid type PBS, or a reflective type polarizer (e.g. a dual brightness enhancement film (DBEF)) and can provide effects of refraction or reflection to incident light having different polarization states. Moreover, the wave plate 112 is, for instance, a quarter-wave plate 112 for changing the polarization state of the incident light. Moreover, the reflection unit 114 is, for instance, coated with a reflective metal layer and can achieve the function of light reflection. For instance, in the present embodiment, the reflection unit 114 can be an aspheric concave mirror, but the disclosure is not limited thereto.

Specifically, referring to FIG. 4, the image display unit 111 can receive at least one type of surgical information from the control storage module 120 and accordingly provide an image beam IB. For instance, the image beam IB can include surgical information such as an organ tissue image, medical records, or physiological signals of the patient. The drive unit module 160 is electrically connected to the image display unit 111 of the virtual image display module 110 for driving the image display unit 111 to provide the image beam IB. More specifically, in the present embodiment, the image display unit 111, for instance, includes a light source module 111*a* and a display panel 111*b*. The light source module 111*a* provides an illumination beam, and the display panel 111*b* is disposed on the transmission path of the illumination beam and converts the illumination beam into the image beam IB. For instance, in the present embodiment, the display panel 111*b* can be a liquid crystal display panel 111*b* or a liquid-crystal-on-silicon (LCOS) display, but the disclosure is not limited thereto.

Moreover, also as shown in FIG. 4, the beam splitting unit 115 is disposed on the transmission path of the image beam IB and an object beam SB from an environment object, and the wave plate 112 and the reflection unit 114 are disposed on the transmission path of a part of the image beam IB. More specifically, the wave plate 112 is located between the beam splitting unit 115 and the reflection unit 114 and can be used to change the polarization state of the image beam IB. Furthermore, in the present embodiment, the beam splitting unit 115 causes at least a part of the object beam SB to be transmitted to the eye EY, and causes at least a part of the image beam IB to be transmitted to the eye EY. For instance, the beam splitting unit 115 can cause at least a part of the object beam SB to pass through and be transmitted to the eye EY, and cause at least a part of the image beam IB emitted by the image display unit 111 to pass through and be transmitted to the reflection unit 114. In particular, the at least a part of the image beam IB and the at least a part of object beam SB passing through the beam splitting unit 115 are of a first polarization state. Then, the image beam IB is transmitted to the reflection unit 114 after passing through the wave plate 112. In the present embodiment, since the wave plate 112 has the phase retardation effect of a quarter-wavelength, the polarization state of the image beam IB is changed to a circular polarization state.

Then, after the image beam IB is reflected by the reflection unit 114, the image beam IB passes through the wave plate 112 again, and therefore the polarization state is further changed to a second polarization state. In particular, the first polarization state and the second polarization state are, for instance, linear polarization states orthogonal to each other. Next, the image beam IB of the second polarization state is transmitted to the beam splitting unit 115 and can be reflected to the eye EY to display a virtual image VI.

Moreover, in the present embodiment, since the object beam SB from an environment object can also pass through the ambient light adjustment unit 140 and the beam splitting unit 115 and be transmitted to the eye EY, the user UR can also observe the physical image in front of the virtual image display system 100 and the virtual image VI at the same time. The user UR can also make the virtual image VI and the physical image be displayed independently or on top of one another in front of the eye (as shown in FIG. 5A to FIG. 5C) through the control unit 123 according to actual need.

However, in general, the smaller the focal length of the reflection unit 114, the greater the viewing angle of the virtual image display system 100, and the size of each of the other optical elements is also increased. As a result, aberration of off-axis light such as distortion, field curvature, and astigmatism become obvious, thereby affecting image quality. Therefore, the overall design of the optical structure of the virtual image display module 110 can be carried out with different optical assemblies according to actual need to maintain good image quality. FIG. 6A to FIG. 6D are used to further explain the overall design of the optical structure of the virtual image display module 110 below.

Figure 6A:
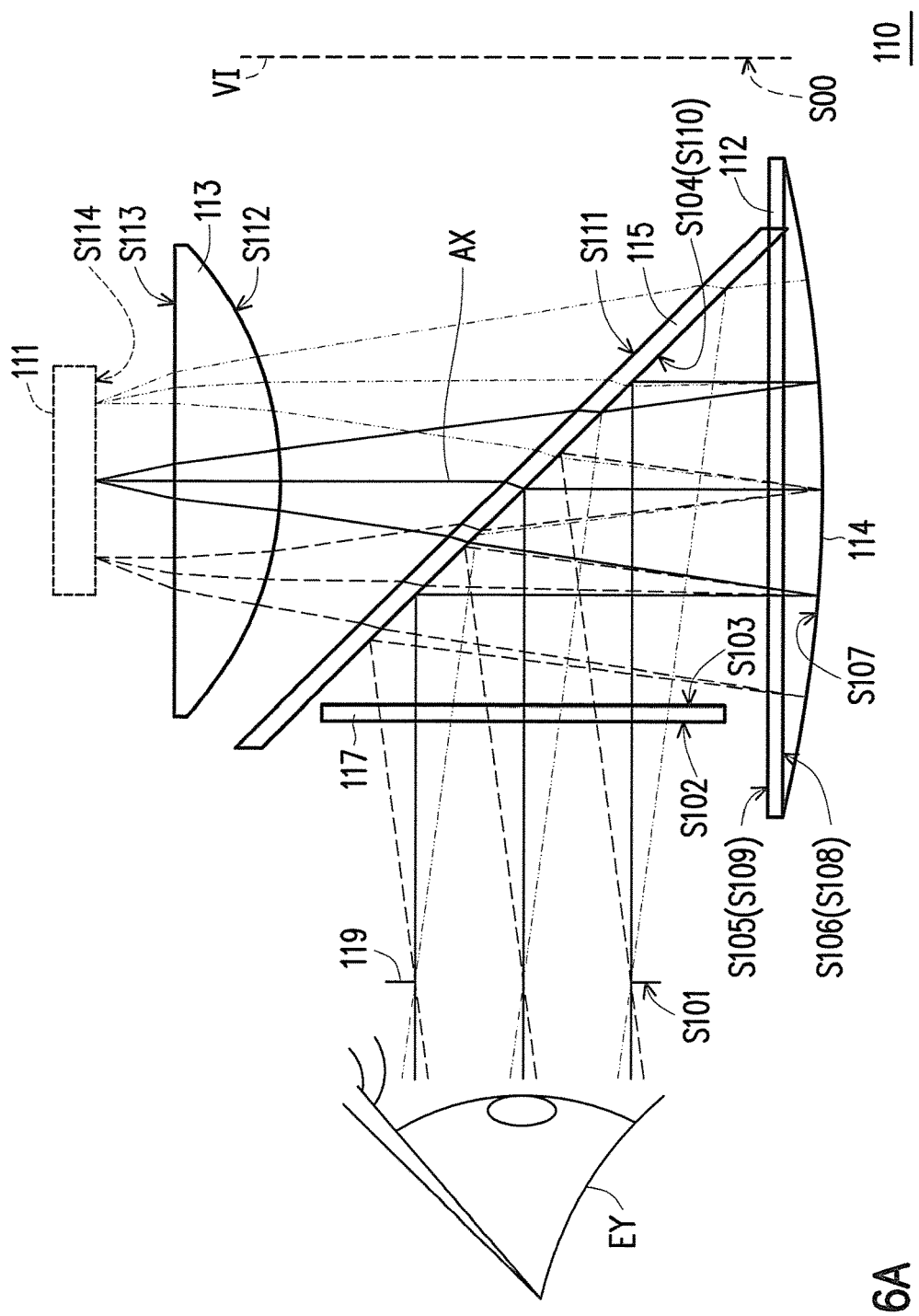
FIG. 6A is a schematic diagram of the architecture of a virtual image display module of FIG. 1.

FIG. 6A is a schematic diagram of the architecture of a virtual image display module of FIG. 1. Referring to FIG. 6A, in the present embodiment, the virtual image display system 100 can include a motion compensation lens group 113. In particular, the motion compensation lens group 113 is disposed on the transmission path of the image beam IB and located between the image display unit 111 and the beam splitting unit 115. When a smaller focal length is designed for the reflection unit 114 due to the need for a larger viewing angle, the motion compensation lens group 113 can compensate the aberration generated as a result to improve image quality. For instance, the motion compensation lens group 113 can be a convex lens. More specifically, in the present embodiment, the motion compensation lens group 113 is a plane-convex lens. However, the disclosure is not limited thereto. In other embodiments, the motion compensation lens group 113 can have different optical lens elements according to actual need and achieve a good overall optical design effect.

Specifically, in the present embodiment, the refractive power of each of the motion compensation lens group 113 and the reflection unit 114 is positive. In other words, in the present embodiment, the reflection unit 114 is a concave mirror. Moreover, the focal length of the motion compensation lens group 113 is less than the focal length of the reflection unit 114. Accordingly, in the present embodiment, the image display unit 111 can be disposed within the total focal length of the focal length of the reflection unit 114 and the focal length of the motion compensation lens group 113 to generate an upright magnified virtual image VI to the eye EY of the user UR. Moreover, when the motion compensation lens group 113 is disposed between the image display unit 111 and the beam splitting unit 115 and the focal length of the motion compensation lens group 113 is less than the effective focal length of the reflection unit 114, the aberration can be effectively corrected to improve image quality.

Moreover, referring to FIG. 6A, in the present embodiment, when the virtual image display system 100 is in a mode adapted for a user with normal vision, the virtual image display system 100 satisfies d-ΣA<f, wherein d is the distance between the image display unit 111 and a surface of the reflection unit 114, f is the focal length of the reflection unit 114, A is a specific value obtained by dividing the difference between an optical path length and an actual length of any location on an optical path along an optical axis AX between the image display unit 111 and the reflection unit 114 by an index of refraction of the location, and ΣA is the sum of A of all of the locations on the optical path along the optical axis AX between the image display unit 111 and the reflection unit 114, wherein at least a part of the A of all of the locations are different. Specifically, in the present embodiment, d-ΣA<f can be represented as:

$$d - \left(\sum_i ((OPL_i - t_i)/n_i)\right) < f$$

In particular, $OPL_i$ is the optical path length in a small actual length (such as a small distance between any location and the next location) adjacent to any location on an optical path along the optical axis AX between the image display unit 111 and the reflection unit 114, $t_i$ is the small actual length (such as a small distance between any location and the next location) adjacent to any location on an optical path along the optical axis AX between the image display unit 111 and the reflection unit 114, and $n_i$ is the index of refraction of any location on the optical path along the optical axis AX between the image display unit 111 and the reflection unit 114. Therefore, $OPL_i$ can also be represented as $n_i \times t_i$. When the number of locations on the optical path approaches infinity and $t_i$ approaches 0, the concept of the Σ operator becomes a concept of integration.

In the present embodiment, optical elements such as the motion compensation lens group 113, the beam splitting unit 115, the reflection unit 114, and the wave plate 112 are all disposed in the air (i.e., the index of refraction thereof is close to 1), so that the optical path length $OPL_i$ located in the optical elements is different than the actual length $t_i$ on the optical path along the optical axis AX between the image display unit 111 and the reflection unit 114. Moreover, a part of the optical path length $OPL_i$ located in the air is substantially the same as the actual length That is, the difference between the optical path length $OPL_i$ and the actual length $t_i$ is zero. Moreover, in the present embodiment, the index of refraction of each of the optical elements is assumed to be a constant value (i.e., the optical elements are assumed to be uniform materials). As a result, the formula above can be simplified as:

$$d - \left(\sum_{j=0}^{k} ((n_j - 1) * t_j)/n_j\right) < f$$

In particular, $n_j$ represents the index of refraction of any optical element (optical elements such as motion compensation lens group 113, beam splitting unit 115, reflection unit 114, and wave plate 112 illustrated in FIG. 1), k represents the number of optical elements included on the optical path along the optical axis AX between image display unit 111 and the reflection unit 114, and $t_j$ represents the thickness along the optical axis AX of any optical element (optical elements such as motion compensation lens group 113, beam splitting unit 115, reflection unit 114, and wave plate 112 illustrated in FIG. 1). For instance, in the present embodiment, m can represent the index of refraction of the motion compensation lens group 113, $n_z$ can represent the index of refraction of the beam splitting unit 115, $t_l$ can represent the thickness of the motion compensation lens group 113 along the optical axis AX, and $t_z$ can represent the thickness of the beam splitting unit 115 along the optical axis AX and so on. However, the number of the optical elements is only used as an example for explaining the present embodiment. Other embodiments can have different numbers of materials having different indexes of refraction. Moreover, the optical elements can also be disposed in a material having an index of refraction other than 1, but the disclosure is not limited thereto.

More specifically, in the present embodiment, the image display unit 111, the motion compensation lens group 113, the beam splitting unit 115, the reflection unit 114, and the wave plate 112 can be designed together to determine the imaging properties of the virtual image VI. In particular, the detailed optical parametric design is as shown in Table 1A:

virtual image display module 110 allows the location of the eye EY to have a larger horizontal visual range and the pupil of the eye EY to move within the range of the diameter of the exit pupil 119 of the surface S101 without affecting the quality of the virtual image VI. In other words, the pupil of the eye EY can still observe good quality of the virtual image VI within a specific movement range when the virtual image display system 100 is worn. As a result, the eye EY can naturally observe the contents displayed by the virtual image VI without readily causing fatigue to the eye EY. Moreover, in the present embodiment, the exit pupil 119 of the virtual image display module 110 is substantially equal to the aperture stop. The surface S102 and the surface S103 represent the two surfaces of a sheet glass 117 light passes through. In the present embodiment, the sheet glass 117 is a plain cover glass, but the disclosure is not limited thereto. In other embodiments, a suitable lens can be selected for the sheet glass 117 according to the actual need of the user UR to compensate for vision.

Next, the surface S104 represents the surface of the beam splitting unit 115 facing the sheet glass 117. The surfaces S105 and S106 represent the two surfaces of the wave plate 112. The surface S107 represents the reflecting surface of the reflection unit 114. The surfaces S108 and S109 represent the two surfaces of the wave plate 112 light passes through again in sequence. The surfaces S110 and S111 represent the two surfaces of the beam splitting unit 115 light passes through again in sequence. The surfaces S112 and S113 represent the two surfaces of the motion compensation lens group 113 (i.e., plane-convex lens).

TABLE 1A

| Surface | Surface type | Radius of curvature | Distance | Material | Note |
| --- | --- | --- | --- | --- | --- |
| S00 | Sphere | Infinity | −3000.00 | | Virtual image VI |
| S101 | Sphere | Infinity | 10.00 | | Exit pupil 119 |
| S102 | Sphere | Infinity | 0.70 | BK7 | Sheet glass 117 |
| S103 | Sphere | Infinity | 8.00 | | |
| S104 | Sphere | Infinity | −9.00 | | Beam splitting unit 115 |
| S105 | Sphere | Infinity | −0.55 | BK7 | Wave plate 112 |
| S106 | Sphere | Infinity | −1.50 | | |
| S107 | Aspheric surface | 53.54267 | 1.50 | | Reflecting unit 114 |
| S108 | Sphere | Infinity | 0.55 | BK7 | Wave plate 112 |
| S109 | Sphere | Infinity | 9.00 | | |
| S110 | Sphere | Infinity | 0.99 | BK7 | Beam splitting unit 115 |
| S111 | Sphere | Infinity | 8.11 | | |
| S112 | Sphere | 13.07314 | 3.8 | BK7 | Motion compensation lens group 113 |
| S113 | Sphere | Infinity | 3 | | |
| S114 | Sphere | Infinity | 0.00 | | Image display unit 111 |

In Table 1A, the unit of the radius of curvature is millimeter (mm), and BK7 in the materials represents an optical glass having an index of refraction of about 1.517 and an Abbe number of about 64.2. The numbering of the material column is the material numbering commonly used in the industry. Moreover, the surfaces S00 to S114 in Table 1A are respectively as illustrated in FIG. 6A and represent the surfaces the beam passes through in sequence on the path from the virtual image VI to the image display unit 111. In particular, the surface S00 represents the location of the virtual image VI and S114 represents the display surface of the image display unit 111.

More specifically, the surface S101 represents an exit pupil 119 of the virtual image display system 100. In the present embodiment, in the virtual image display module 110, the exit pupil 119 has a large diameter and therefore the More specifically, the distance of each of the surfaces represents the distance between each of the surfaces and the next surface, and in the present embodiment, a negative distance signifies the imaging thereof is a virtual image VI. However, the disclosure is not limited thereto. The description and the table above are only used as aids in describing the present embodiment.

Moreover, a number of important parameter values of the virtual image display module 110 are exemplified below. In the present embodiment, the field of view of the virtual image display module 110 is 30 degrees, the f-number is 2.6, the lateral color aberration is 7.95 μm, and the ratio of the diameter of the reflection unit 114 to the diameter of the exit pupil 119 is 2.89. Moreover, the asphericity of the aspheric surface (such as surface S107) is as shown in Table 1B:

TABLE 1B

|  | S107 |
| --- | --- |
| Radius of lens | 53.54267 |
| Conic constant (K) | −15.7244 |
| 4th order parameter ($A_4$) | $1.26 \times 10^{-05}$ |
| 6th order parameter ($A_6$) | $-2.68 \times 10^{-08}$ |
| 8th order parameter ($A_8$) | $9.75 \times 10^{-11}$ |
| 10th order parameter ($A_{10}$) | $-3.33 \times 10^{-13}$ |

In particular, the function of the aspheric surface is as shown in the following formula:

$$Z(Y) = \frac{CY^2}{1 + (1 - (1+K)(C)^2 Y^2)^{1/2}} + (A_4)Y^4 + (A_6)Y^6 + (A_8)Y^8 + (A_{10})Y^{10}$$

In the formula, Z(Y) is the sag of the surface apex or a relevant vertical line along the direction of the optical axis AX, and C is the reciprocal of the radius of an osculating sphere, that is, the reciprocal of the radius of curvature (such as the radius of curvature of S107 in Table 1A) adjacent to the optical axis AX. k is the conic coefficient, Y is the aspheric height, that is, the height from the center of the lens to the edge of the lens, and A4, A6, A8, and A10 are aspheric coefficients. Accordingly, the virtual image display system 100 can display good image quality while having a compact size.

Furthermore, in the present embodiment, as shown in FIG. 6A, the user UR can adjust the distance from the image display unit 111 to the reflection unit 114 through the control unit 123 according to personal habits to correspondingly change the imaging position and the size of the image frame of the virtual image VI to facilitate the use of the virtual image display system 100. More specifically, in the present embodiment, the image display unit 111 and the motion compensation lens group 113 can move along the optical axis AX at the same time to adjust the imaging position and the size of the image frame of the virtual image VI. In particular, the relationship between the distance from the image display unit 111 to the reflection unit 114 and the imaging position and the size of the image frame of the virtual image VI is as shown in Table 1C:

TABLE 1C

| Surface | Distance (mm) | Size of image frame (inch) |
| --- | --- | --- |
| S00 | −250 | 5.5" |
| S111 | 5.51 |  |
| S00 | −500 | 11" |
| S111 | 6.93 |  |
| S00 | −1000 | 22" |
| S111 | 7.64 |  |
| S00 | −2000 | 44" |
| S111 | 7.99 |  |
| S00 | −3000 | 66" |
| S111 | 8.11 |  |
| S00 | −4000 | 88" |
| S111 | 8.17 |  |
| S00 | −5000 | 110" |
| S111 | 8.2 |  |
| S00 | −6000 | 132" |
| S111 | 8.23 |  |

In Table 1C, the distance of the surface S00 represents the location of the virtual image VI seen by the eye of the user UR. In other words, in the present embodiment, the location of the eye EY and the location of the exit pupil 119 are similar. The distance of the surface S111 represents the distance between the lens surface closest to the beam splitting unit 115 along the direction of the optical axis AX and the beam splitting unit 115 in the motion compensation lens group 113. In the present embodiment, the control unit 123 can adjust the location of each of the image display unit 111 and the motion compensation lens group 113 along the direction of the optical axis AX relative to the beam splitting unit 115 according to actual need. In this way, the corresponding imaging position or size of the image frame of the virtual image VI can be obtained. Moreover, in the present embodiment, when the distance of the surface S111 is 8.334 mm, the largest size of the image frame of the virtual image VI can be obtained.

Furthermore, for users UR with myopia or hyperopia, the virtual image display system 100 can also change the distance from the image display unit 111 to the reflection unit 114 through the control unit 123 to adapt to the refractive power of the eye EY of different users UR. Therefore, in the present embodiment, users UR with myopia or hyperopia can clearly observe the image displayed by the virtual image display system 100 without having to wear additional corrective glasses.

Furthermore, referring again to FIG. 3, in the present embodiment, the storage unit 121 can further store a datasheet of visual compensation 121c. More specifically, in the present embodiment, the control unit 123 can search the datasheet of visual compensation 121c according to the actual need of the eyesight of the user UR to obtain information of visual compensation, and can adjust the location of each of the image display unit 111 and the motion compensation lens group 113 relative to the beam splitting unit 115 according to the information of visual compensation, and accordingly change the distance from the image display unit 111 to the reflection unit 114 to adjust the imaging position or the size of the image frame of the virtual image VI. For instance, the relationship between the location of each of the image display unit 111 and the motion compensation lens group 113 relative to the beam splitting unit 115 and the refractive power of the eye EY of the user UR is as exemplified in Table 1D and Table 1E below:

TABLE 1D

| Myopia | | | | | |
| --- | --- | --- | --- | --- | --- |
| Virtual image located 3 m in front of eye | | | Virtual image located 50 cm in front of eye | | |
| Refractive power | Degree | Distance of surface S111 (mm) | Refractive power | Degree | Distance of surface S111 (mm) |
| −1 D | −100 | 7.42 | −1 D | −100 | 6.25 |
| −2 D | −200 | 6.73 | −2 D | −200 | 5.59 |
| −3 D | −300 | 6.06 | −3 D | −300 | 4.93 |
| −4 D | −400 | 5.39 | −4 D | −400 | 4.28 |
| −5 D | −500 | 4.74 | −5 D | −500 |  |
| −6 D | −600 | 4.07 | −6 D | −600 |  |

TABLE 1E

Hyperopia

| | Virtual image located 3 m in front of eye | | | Virtual image located 50 cm in front of eye | |
|---|---|---|---|---|---|
| Refractive power | Degree | Distance of surface S111 (mm) | Refractive power | Degree | Distance of surface S111 (mm) |
| 1 D | 100 | 8.81 | 1 D | 100 | 7.62 |
| 2 D | 200 | 9.53 | 2 D | 200 | 8.32 |
| 3 D | 300 | 10.26 | 3 D | 300 | 9.03 |
| 4 D | 400 | 10.99 | 4 D | 400 | 9.74 |
| 5 D | 500 | 11.74 | 5 D | 500 | 10.47 |
| 6 D | 600 | 12.52 | 6 D | 600 | 11.23 |
| 7 D | 700 | 13.31 | 7 D | 700 | 12.00 |
| 8 D | 800 | 14.06 | 8 D | 800 | 12.73 |
| 9 D | 900 | 14.87 | 9 D | 900 | 13.52 |
| 10 D | 1000 | 15.68 | 10 D | 1000 | 14.30 |
| 15 D | 1500 | 20.11 | 15 D | 1500 | 18.59 |
| 20 D | 2000 | 24.70 | 20 D | 2000 | 23.02 |

In Table 1D and Table 1E, the positive and negative of the refractive power (e.g. diopter) of the eye EY of the user UR respectively represent hyperopia and myopia, and the magnitude of the refractive power can be converted to the corresponding degree of hyperopia or myopia. Moreover, the meaning of the distance of the surface S111 is as described in Table 1C and is not repeated herein.

Moreover, in Table 1D and Table 1E, although the virtual image display system 100 changes the distance from the image display unit 111 to the reflection unit 114 by adjusting the location of each of the image display unit 111 and the motion compensation lens group 113 relative to the beam splitting unit 115, the disclosure is not limited thereto. For instance, in the present embodiment, the virtual image display system 100 can also adjust the relative position of the image display unit 111 and the motion compensation lens group 113 according to the information of visual compensation to achieve a similar effect to changing the distance from the image display unit 111 to the reflection unit 114. Accordingly, the virtual image display system 100 can also adjust the imaging position or the size of the image frame of the virtual image VI to adapt to the need of the refractive power of the eye EY of different users UR. For instance, the relationship between the relative position of the image display unit 111 and the motion compensation lens group 113 and the refractive power of the eye EY of the user UR is as exemplified in Table 1F and Table 1G below:

TABLE 1F

Myopia

| | Virtual image located 3 m in front of eye | | | Virtual image located 50 cm in front of eye | |
|---|---|---|---|---|---|
| Refractive power | Degree | Distance of surface S113 (mm) | Refractive power | Degree | Distance of surface S113 (mm) |
| −1 D | −100 | 2.47 | −1 D | −100 | 1.68 |
| −2 D | −200 | 2.01 | −2 D | −200 | 1.20 |
| −3 D | −300 | 1.54 | −3 D | −300 | 0.70 |
| −4 D | −400 | 1.05 | −4 D | −400 | 0.18 |
| −5 D | −500 | 0.55 | −5 D | −500 | |
| −6 D | −600 | 0.01 | −6 D | −600 | |

TABLE 1G

Hyperopia

| | Virtual image located 3 m in front of eye | | | Virtual image located 50 cm in front of eye | |
|---|---|---|---|---|---|
| Refractive power | Degree | Distance of surface S113 (mm) | Refractive power | Degree | Distance of surface S113 (mm) |
| 1 D | 100 | 3.35 | 1 D | 100 | 2.61 |
| 2 D | 200 | 3.77 | 2 D | 200 | 3.05 |
| 3 D | 300 | 4.18 | 3 D | 300 | 3.48 |
| 4 D | 400 | 4.58 | 4 D | 400 | 3.89 |
| 5 D | 500 | 4.97 | 5 D | 500 | 4.30 |
| 6 D | 600 | 5.35 | 6 D | 600 | 4.70 |
| 7 D | 700 | 5.72 | 7 D | 700 | 5.09 |
| 8 D | 800 | 6.06 | 8 D | 800 | 5.45 |
| 9 D | 900 | 6.41 | 9 D | 900 | 5.82 |

In Table 1F and Table 1 G, the meaning of each of the refractive power and the degree is as described in Table 1D and Table 1E and is not repeated herein. Moreover, the meaning of the distance of the surface S113 represents the distance between the surface S113 in the motion compensation lens group 113 facing the image display unit 111 and the display surface (i.e., surface S114) of the image display unit 111 along the direction of the optical axis AX.

Moreover, in Table 1D to Table 1G, only information of visual compensation corresponding to the virtual image VI located 3 m and 50 cm in front of eye are shown, but the disclosure is not limited thereto. When the virtual image VI is in a different location, the corresponding information of visual compensation is also available and is not repeated herein.

Figure 6B:
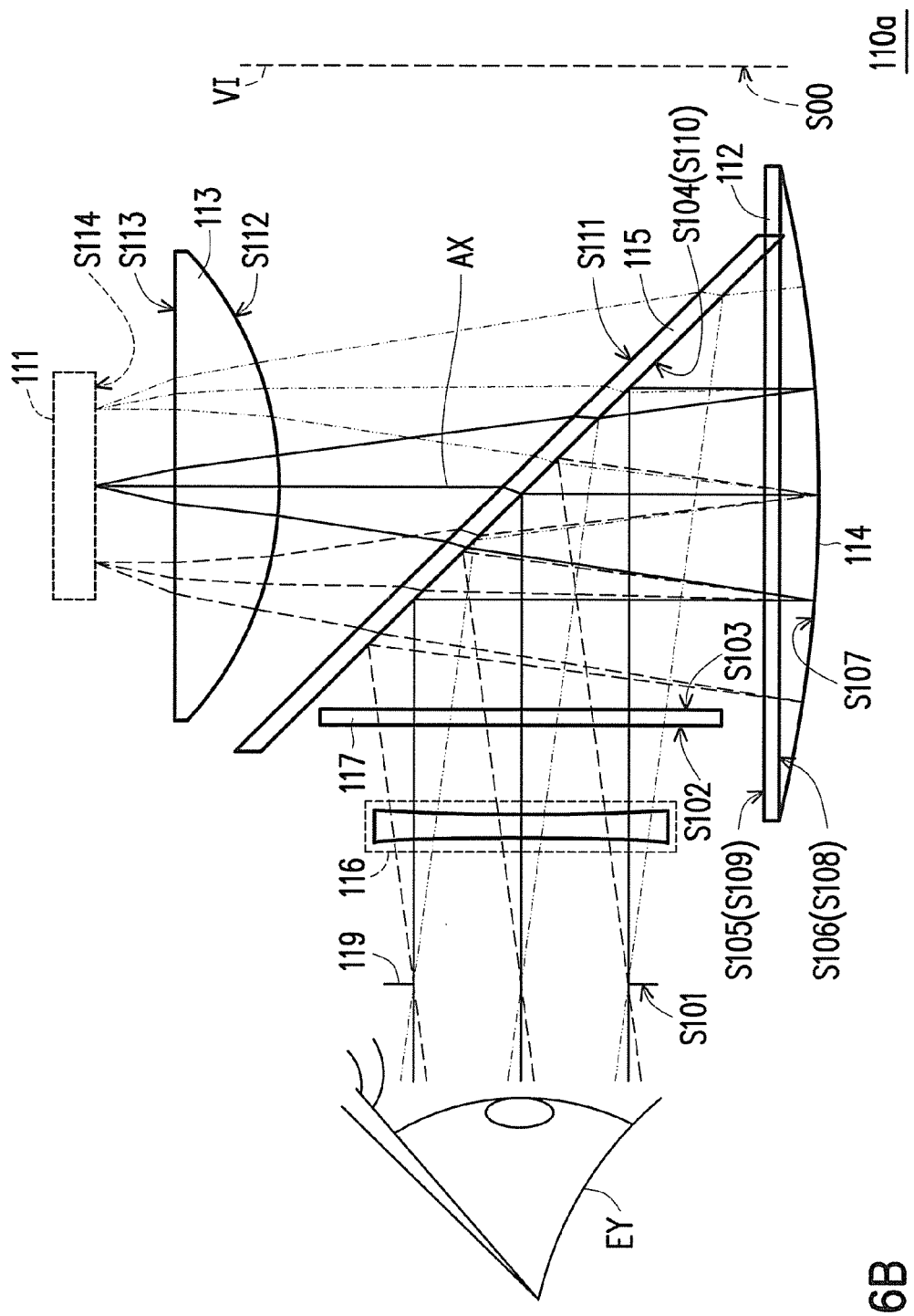
FIG. 6B is a schematic diagram of the architecture of another virtual image display module of FIG. 1.
Figure 6C:
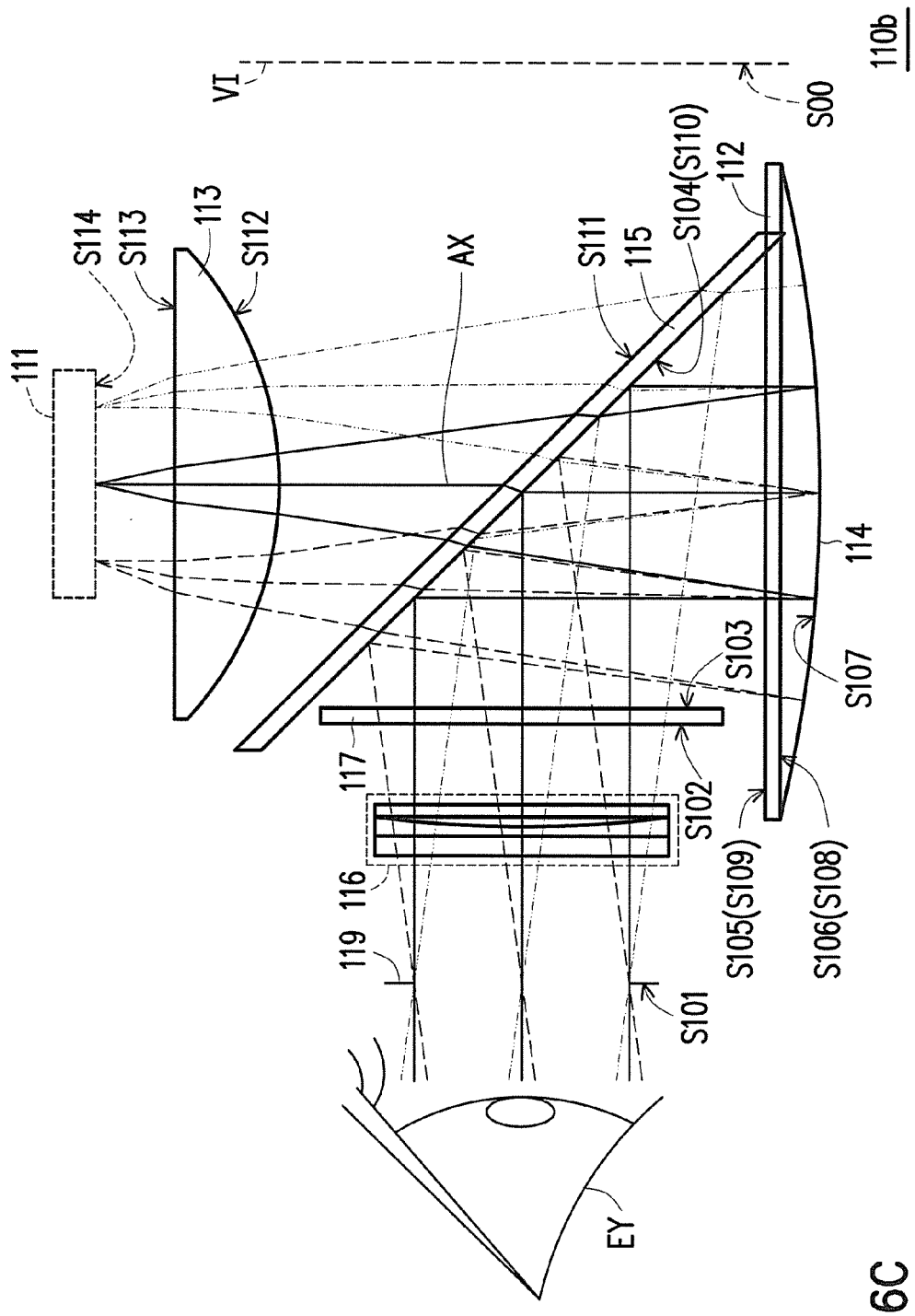
FIG. 6C is a schematic diagram of the architecture of yet another image display module of FIG. 1.
Figure 6D:
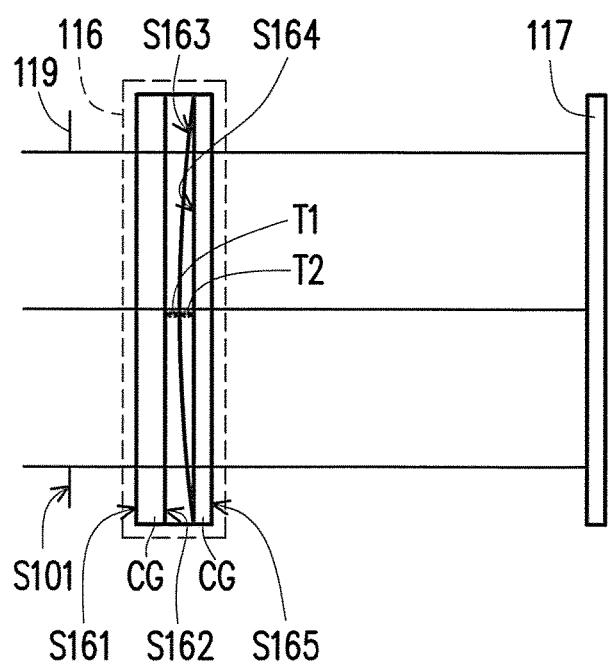
FIG. 6D is a schematic structural diagram of the liquid lens of FIG. 6C.

Furthermore, although the virtual image display module 110 achieves the function of adapting to the refractive power of the eye EY of different users UR by changing the distance from the image display unit 111 to the reflection unit 114, the disclosure is not limited thereto. In other embodiments, the virtual image display module 110 can also achieve the effect of adapting to the refractive power of the eye EY of different users UR through different optical properties of the internal optical elements. FIG. 6B to FIG. 6D are used for further explanation below.

FIG. 6B is a schematic diagram of the architecture of another virtual image display module of FIG. 1. Referring to FIG. 6B, the virtual image display module 110a of the present embodiment is similar to the virtual image display module 110 of FIG. 6A, and the difference between the two is as described below. In the present embodiment, the virtual image display module 110a further includes a first compensation lens 116 and the first compensation lens 116 is a lens having a refractive power. For instance, in the present embodiment, the material of the first compensation lens 116 can be glass. Specifically, the first compensation lens 116 is disposed on the transmission path of the image beam IB and is located between the beam splitting unit 115 and the eye EY. More specifically, in the present embodiment, the first compensation lens 116 is located between the sheet glass 117 and the exit pupil 119.

In the present embodiment, since the first compensation lens 116 has a refractive power, the first compensation lens 116 can also be used to compensate and adapt to the refractive power of the eye EY of different users UR. In other words, the user UR can select a first compensation lens 116 having a suitable focal length according to the information of visual compensation to compensate for vision. For instance, the relationship between the focal length of the first compensation lens 116 and the eyesight of the eye EY of the user UR is as exemplified in Table 1H below:

TABLE 1H

| | Myopia | | Hyperopia |
|---|---|---|---|
| Degree | Focus (mm) | Degree | Focus (mm) |
| 0 | 0 | 0 | 0 |
| −100 | −1000 | 100 | 1000 |
| −200 | −500 | 200 | 500 |
| −300 | −333.3333333 | 300 | 333.3333333 |
| −400 | −250 | 400 | 250 |
| −500 | −200 | 500 | 200 |
| −600 | −166.6666667 | 600 | 166.6666667 |
| −700 | −142.8571429 | 700 | 142.8571429 |
| −800 | −125 | 800 | 125 |
| −900 | −111.1111111 | 900 | 111.1111111 |
| −1000 | −100 | 1000 | 100 |
| −1500 | −66.66666667 | 1500 | 66.66666667 |
| −2000 | −50 | 2000 | 50 |

In Table 1H, the positive and negative of the degree of eyesight of the user UR respectively represent hyperopia and myopia, and the focal length represents the focal length of the first compensation lens 116.

Moreover, in the present embodiment, although the first compensation lens 116 is exemplified as a lens, the disclosure is not limited thereto. In other embodiments, the first compensation lens 116 can also be an optical assembly having other optical properties. FIG. 6C to FIG. 6D are used for further explanation below.

FIG. 6C is a schematic diagram of the architecture of yet another image display module of FIG. 1. FIG. 6D is a schematic structural diagram of the liquid lens of FIG. 6C. Referring to FIG. 6C and FIG. 6D, the virtual image display module 110b of the present embodiment is similar to the virtual image display module 110a of FIG. 6B, and the difference between the two is as described below. In the present embodiment, the first compensation lens 116 of the virtual image display module 110b is a liquid lens. For instance, in the present embodiment, the first compensation lens 116 is a liquid lens made by Varioptic Corporation having the model number Artic 416.

Specifically, in the present embodiment, the first compensation lens 116 can further be electrically connected to the control unit 123, and the control unit 123 can adjust the first compensation lens 116 according to the information of visual compensation to switch the imaging position of the virtual image VI and thereby achieve the function of adapting to the refractive power of the eye EY of different users UR. In particular, the detailed optical parametric design of the first compensation lens 116 is as shown in Table 1I and the relationship between the eyesight of the eye EY of the user UR and the optical parameters of the first compensation lens 116 is as exemplified in Table 1J:

TABLE 1I

| Surface | Surface type | Radius of curvature | Distance (mm) | Index of Refraction | Abbe Number | Notes |
|---|---|---|---|---|---|---|
| S101 | Sphere | Infinity | 0.6 | | | |
| S161 | Sphere | Infinity | 0.55 | 1.51 | 56.4 | Cover glass CG |
| S162 | Sphere | Infinity | 0.25 | 1.39 | 58.7 | With variable distance T1 |
| S163 | Sphere | 5.98 * variable radius of curvature R1 | 0.4 | 1.48 | 38.4 | With variable distance T2 |
| S164 | Sphere | Infinity | 0.3 | 1.51 | 56.4 | Cover glass CG |
| S165 | Sphere | Infinity | 0.6 | | | |

TABLE 1J

| | Myopia | | | | Hyperopia | | |
|---|---|---|---|---|---|---|---|
| Degree | R1 (mm) | T1 (mm) | T2 (mm) | Degree | R1 (mm) | T1 (mm) | T2 (mm) |
| 0 | Infinity | 0.34 | 0.31 | 0 | Infinity | 0.34 | 0.31 |
| −100 | 90.65626 | 0.34 | 0.31 | 100 | −90.6563 | 0.34 | 0.31 |
| −200 | 45.32813 | 0.33 | 0.32 | 200 | −45.3281 | 0.35 | 0.3 |
| −300 | 30.21845 | 0.32 | 0.33 | 300 | −30.2185 | 0.36 | 0.29 |
| −400 | 22.66406 | 0.32 | 0.33 | 400 | −22.6641 | 0.36 | 0.29 |
| −500 | 18.13125 | 0.31 | 0.34 | 500 | −18.1313 | 0.37 | 0.28 |
| −600 | 15.10877 | 0.3 | 0.35 | 600 | −15.1088 | 0.37 | 0.28 |
| −700 | 12.87319 | 0.3 | 0.35 | 700 | −12.8732 | 0.38 | 0.27 |
| −800 | 11.33203 | 0.29 | 0.36 | 800 | −11.332 | 0.39 | 0.26 |
| −900 | 10.06284 | 0.29 | 0.36 | 900 | −10.0628 | 0.39 | 0.26 |
| −1000 | 9.065626 | 0.28 | 0.37 | 1000 | −9.06563 | 0.4 | 0.25 |
| −1500 | 5.983313 | 0.25 | 0.4 | | | | |
| −2000 | 4.63 | 0.23 | 0.42 | | | | |

In Table 1I, the unit of the radius of curvature is millimeter (mm). The surfaces S161 and S162 are respectively the two surfaces of the two cover glasses CG having liquid lenses for the surfaces S163 and S164 for protecting the liquid lenses. Moreover, the surface S161 is the surface of the liquid lens facing the exit pupil 119 and S165 is the surface of the liquid lens facing the sheet glass 117. Furthermore, in the present embodiment, the liquid lenses can be formed by different materials, the surface S163 is an interface having a different material separating the liquid lenses, and the control unit 123 can control the variable radius of curvature of the surface S163 and the variable distances T1 and T2 of the surfaces S162 and S163 of the liquid lenses to modulate the focal length of each of the liquid lenses. Moreover, in Table 1J, the positive and negative of the degree of eyesight of the user UR respectively represent hyperopia and myopia and the variable radius of curvature of the surface S163 and the variable distances T1 and T2 of the surfaces S162 and S163 of the liquid lenses can be correspondingly adjusted to adapt to the need of the refractive power of the eye EY of different users UR.

FIG. 7A to FIG. 7D are used to further explain the exterior of the virtual image display system 100 below.

Figure 7A:
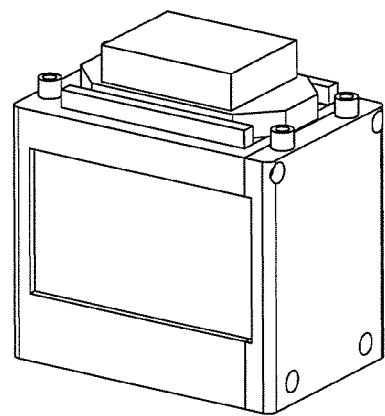
FIG. 7A is a schematic diagram of the exterior of the virtual image display module of FIG. 1.
Figure 7B:
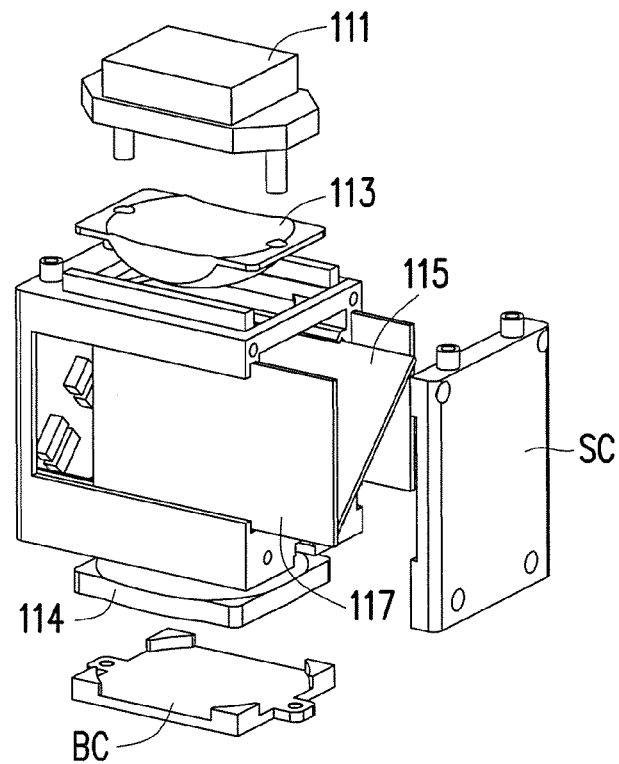
FIG. 7B is an exploded view of the virtual image display module of FIG. 1.
Figure 7C:
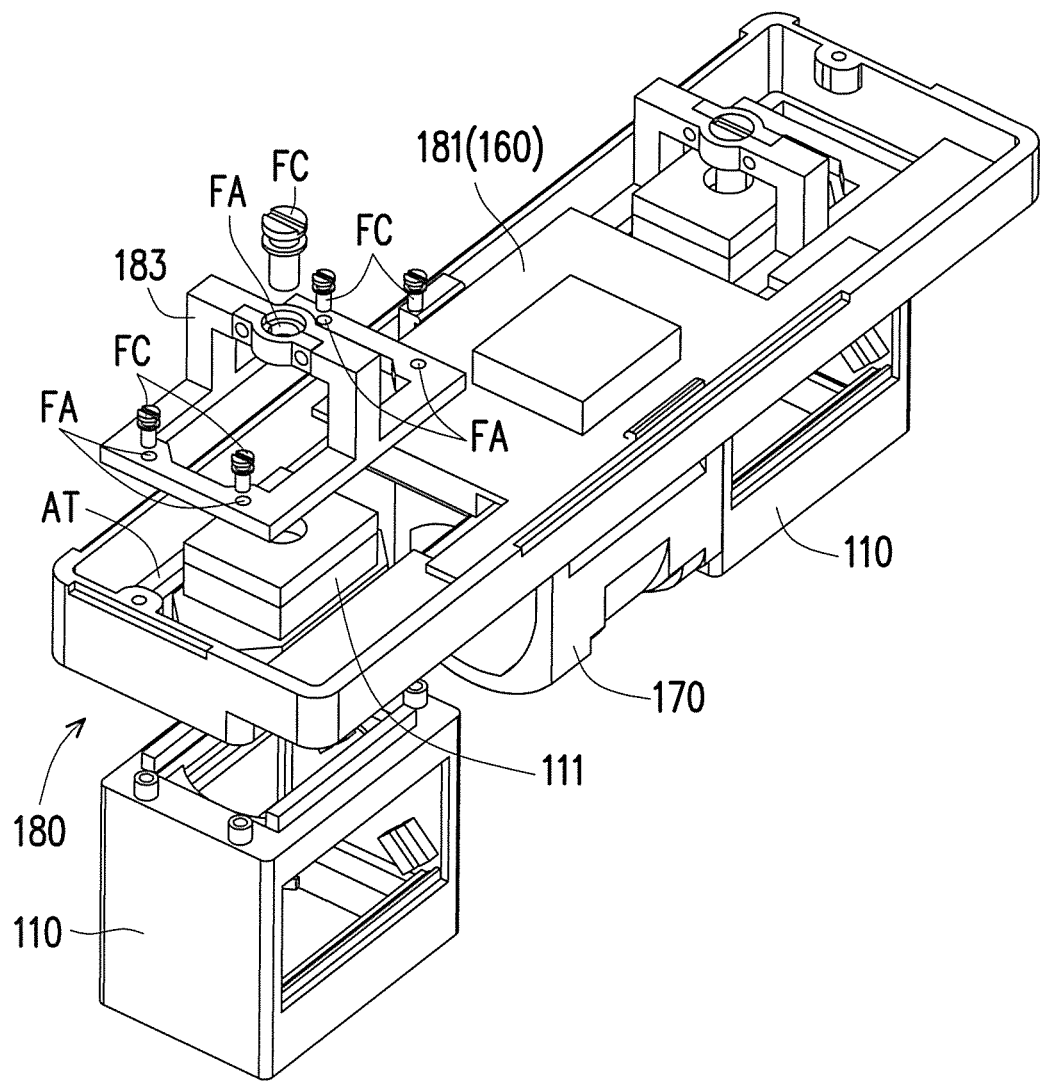
FIG. 7C is an exploded view of a portion of the virtual image display system of FIG. 1.
Figure 7D:
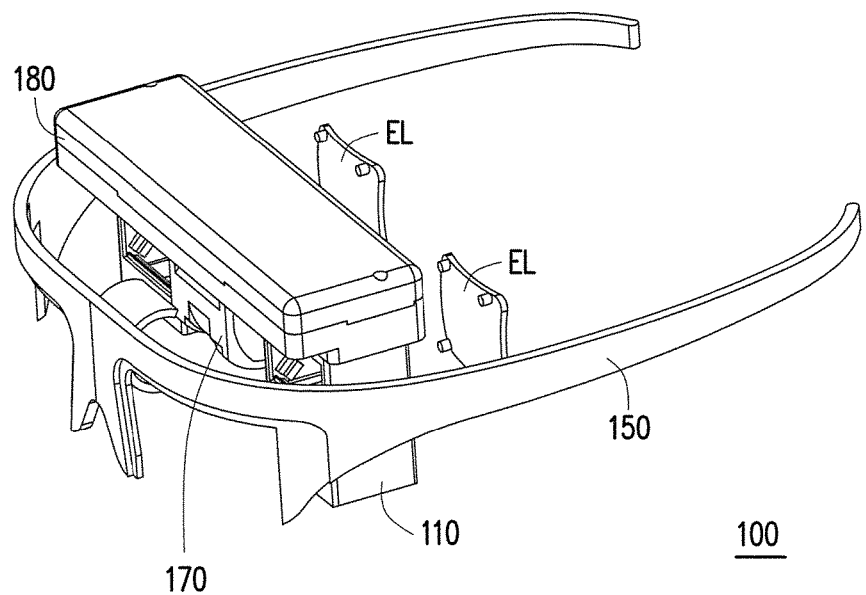
FIG. 7D is an exploded view of a portion of the virtual image display system of FIG. 1.

FIG. 7A is a schematic diagram of the exterior of the virtual image display module of FIG. 1. FIG. 7B is an exploded view of the virtual image display module of FIG. 1. FIG. 7C is an exploded view of a portion of the virtual image display system of FIG. 1. FIG. 7D is an exploded view of a portion of the virtual image display system of FIG. 1. Referring to FIG. 7A and FIG. 7B, in the present embodiment, optical elements such as the sheet glass 117, the beam splitting unit 115, the reflection unit 114, the motion compensation lens group 113, and the bottom cover BC of the virtual image display module 110 are assembled in sequence. Then, the side cover SC of the virtual image display module 110 is pushed in such that the sheet glass 117 and the beam splitting unit 115 can be snapped into the groove of the side cover SC. Next, the motion compensation lens group 113 and the image display unit 111 are fixed with screws to form the virtual image display module 110 (as shown in FIG. 7A). More specifically, in the present embodiment, the center of the virtual image display module 110 can further be positioned through the location of the motion compensation lens group 113.

Moreover, as shown in FIG. 7C, in the present embodiment, the virtual image display system 100 further includes a mechanism adjustment unit module 180 and a rotatable support base 170. Specifically, in the present embodiment, the mechanism adjustment unit module 180 includes a plurality of fastening assemblies FA, a fixing base 181, and at least one fixture 183. More specifically, in the present embodiment, the fixing base 181 can be the casing of a drive unit module 160 and the exterior of the fixing base 181 has an adjustment track AT. Moreover, the fixture 183 is located on the adjustment track AT and the fixture 183 has a plurality of fastening holes FC.

More specifically, at least one virtual image display module 110 is locked onto the fixture 183 through a part of the fastening assemblies FA such that at least one virtual image display module 110 is adapted to move along the adjustment track AT. As a result, in the present embodiment, the virtual image display system 100 can be moved in the lateral direction through the adjustment track AT on the fixing base 181. Moreover, the virtual image display system 100 can also couple the drive unit module 160 (i.e., fixing base 181) to the image display unit 111 of the virtual image display module 110 through the fixture 183 through one of the fastening assemblies FA, and the virtual image display system 100 is adapted to adjust the relative position of each of the drive unit module 160 and the image display unit 111 through the fastening assembly FA. Therefore, the virtual image display module 110 can perforin micro adjustment in the vertical direction.

Moreover, in the present embodiment, the rotatable support base 170 is disposed below the fixing base 181 (i.e., drive unit module 160). Specifically, the rotatable support base 170 is used to support the weight of the stereoscopic virtual image display system 100 on the nose of the user UR and can provide a little rotation on the frame 150 to compensate for the facial differences of different users UR. In this embodiment, at least one virtual image display module 110, the rotatable support base 170, and the frame 150 are combined into a glasses type virtual image display system.

Moreover, as shown in FIG. 7C, in the present embodiment, when the at least one virtual image display module 110 is two virtual image display modules 110, the function of forming a stereoscopic image or a planar image can be obtained. For instance, when each of the two virtual image display modules 110 displays an image and the viewing angles of the two images are different, a stereoscopic image can be formed. Moreover, when the viewing angles of the two images respectively displayed by the two virtual image display modules 110 are the same, a planar image can be formed.

Next, as shown in FIG. 7D, in the present embodiment, the four corners of an external lens EL can also be processed and a magnetic material can be implanted thereto. Moreover, the external lens EL can be directly attached on the virtual image display module 110. In this way, visual compensation can also be carried out according to the need of the eyesight of the eye EY of the user UR to achieve the function of rapidly replacing lenses to match the degree. Moreover, in the present embodiment, the frame 150 can be combined with the at least one virtual image display module 110, the rotatable support base 170, and the mechanism adjustment unit module 180 into a stereoscopic virtual image display system, but the disclosure is not limited thereto.

Figure 7E:
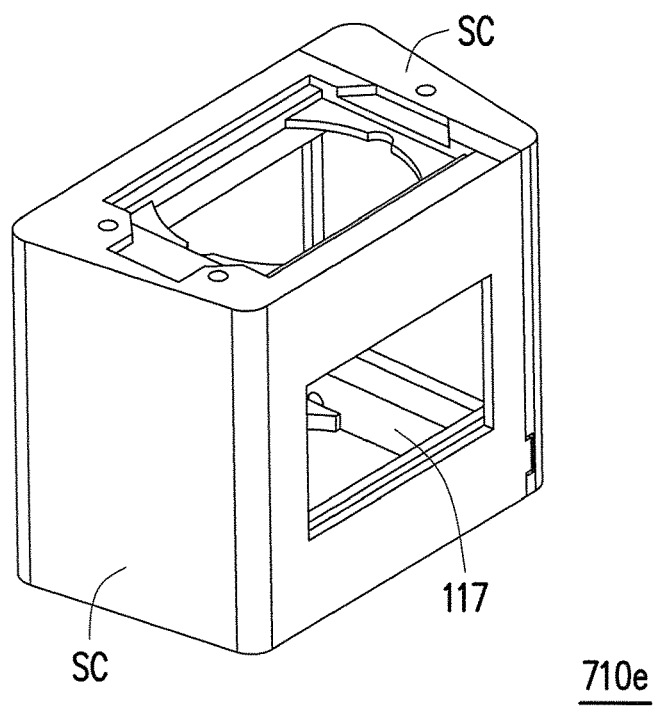
FIG. 7E is another schematic diagram of the exterior of the virtual image display module of FIG. 1.
Figure 7F:
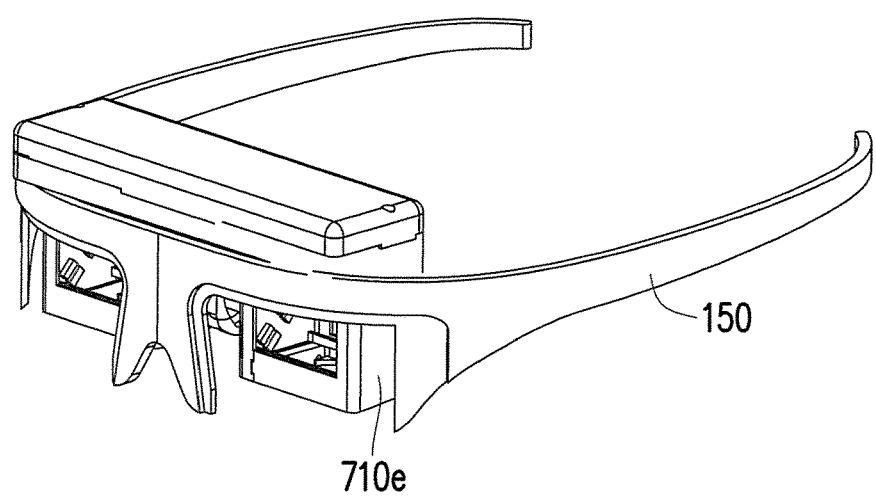
FIG. 7F is a schematic diagram of the exterior of the virtual image display module of FIG. 7E disposed on a frame.

FIG. 7E is another schematic diagram of the exterior of the virtual image display system of FIG. 1. FIG. 7F is a schematic diagram of the exterior of the virtual image display system of FIG. 7E disposed on a frame. Referring to FIG. 7E and FIG. 7F, the virtual image display module 710e of the present embodiment is similar to the virtual image display module 110 of FIG. 7A, and the difference between the two is as described below. In the present embodiment, the angle between the side cover SC located on two sides of the virtual image display module 710e and the sheet glass 117 is not perpendicular. Moreover, in the present embodiment, when the virtual image display module 710e is worn, the width of a side (i.e., the side the sheet glass 117 is on) adjacent to and facing the eye EY is less than the width of the other side away from and facing away from the eye EY. In other words, the appearance of the virtual image display module 710e has a trapezoid shape and the angle sandwiched between the side cover SC on the two sides becomes larger the farther away the angle is from the eye EY. In this way, light entering the virtual image display module 710e can match the viewing angle of the eye to lower the occurrence of light shielding.

Figure 8A:
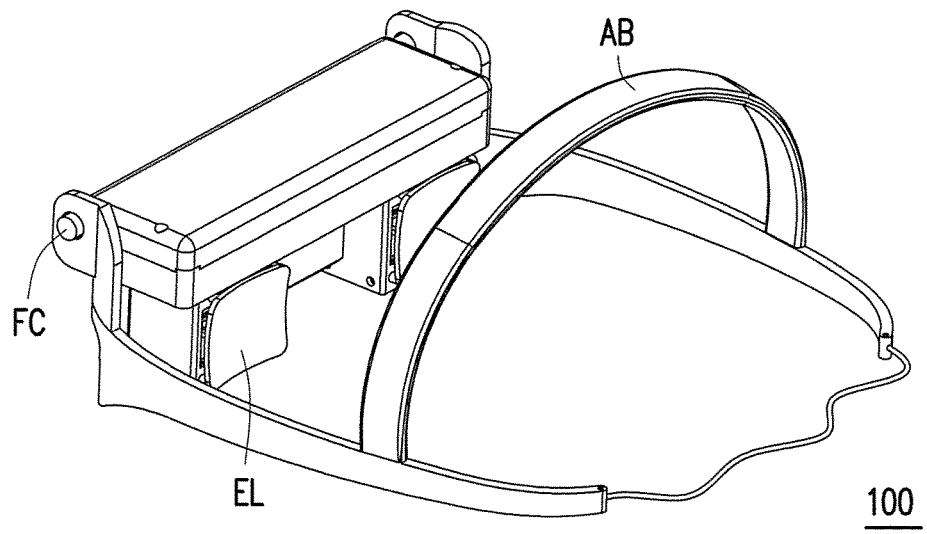
FIG. 8A and FIG. 8B are schematic diagrams of the exterior of another frame of FIG. 1.
Figure 8B:
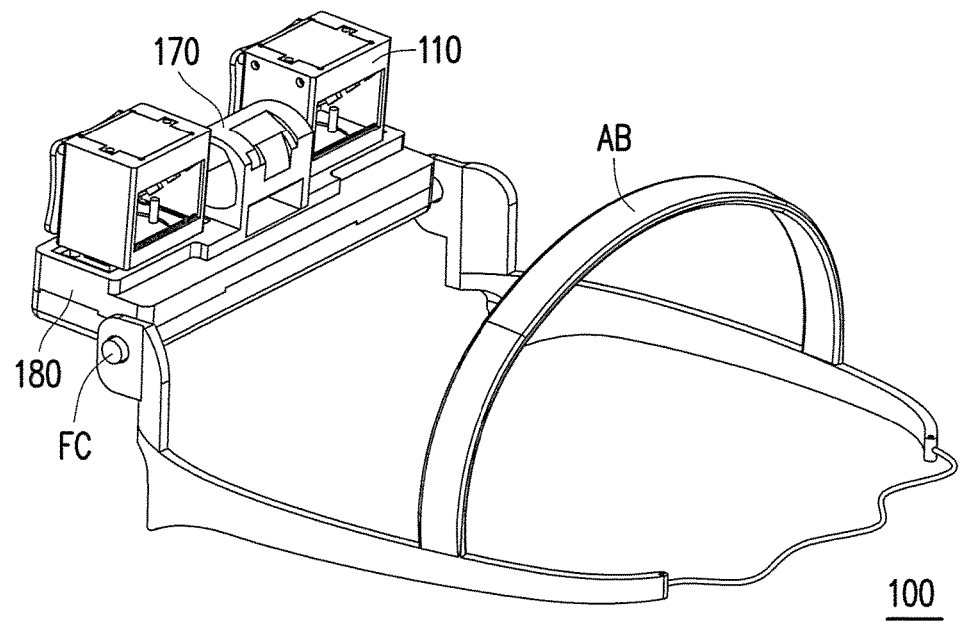
Figure 8C:
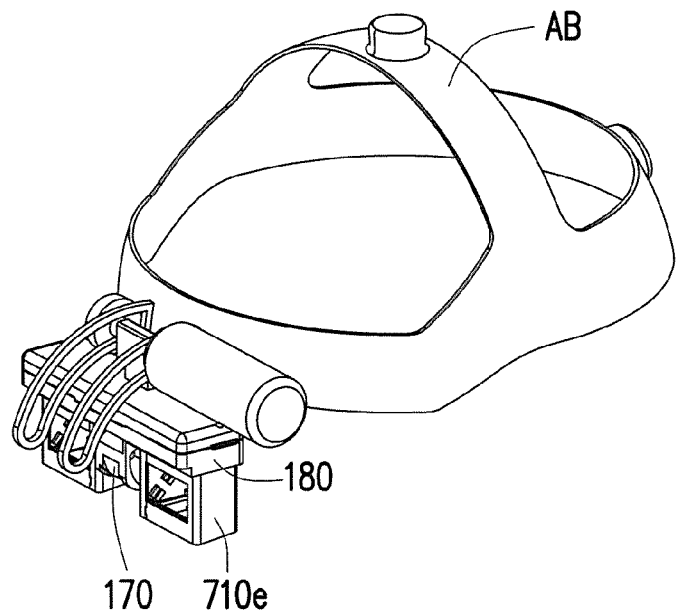
FIG. 8C and FIG. 8D are schematic diagrams of the exterior of the virtual image display module of FIG. 7E disposed on a frame.
Figure 8D:
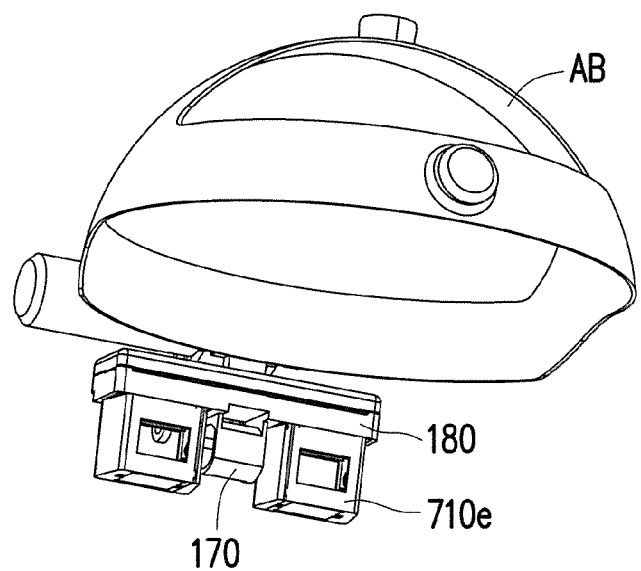

FIG. 8A and FIG. 8B are schematic diagrams of the exterior of another frame of FIG. 1. FIG. 8C and FIG. 8D are schematic diagrams of the exterior of the virtual image display system of FIG. 7E disposed on a frame. As shown in FIG. 8A and FIG. 8B, the frame 150 can also have an auxiliary headband AB and be combined with the at least one virtual image display module 110, the rotatable support base 170, and the mechanism adjustment unit module 180 into a head-mount virtual image display system. Moreover, in the present embodiment, a fastening hole FC can also be disposed on the frame 150 to couple the frame 150 to the two ends of the fixing base 181. More specifically, the coupling site at the two ends of the fixing base 181 with the frame 150 can be designed to be a rotation axis suitable for axial engagement. In this way, the user UR can rotate or open at least one virtual image display module 110 (as shown in FIG. 8B). Moreover, as shown in FIG. 8C and FIG. 8D, the virtual image display module 710e can also be used with the auxiliary headband AB and be combined with the rotatable support base 170 and the mechanism adjustment unit module 180 into a head-mount virtual image display system to achieve the above function.

Figure 9A:
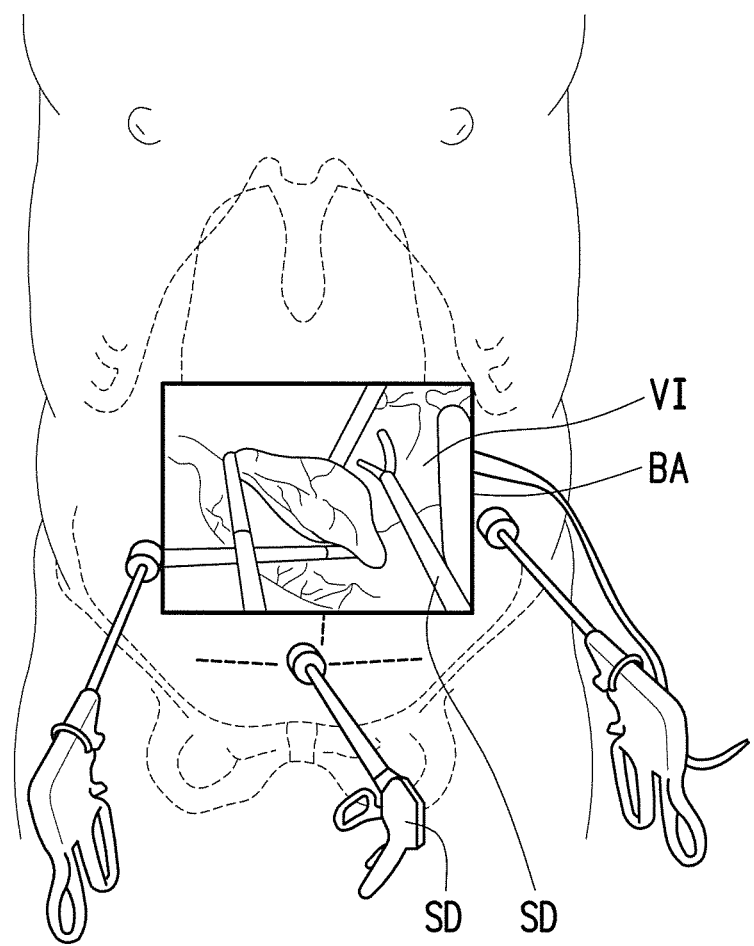
FIG. 9A is a schematic diagram of the blocking area of the object beam of the virtual image display system of FIG. 1.
Figure 9B:
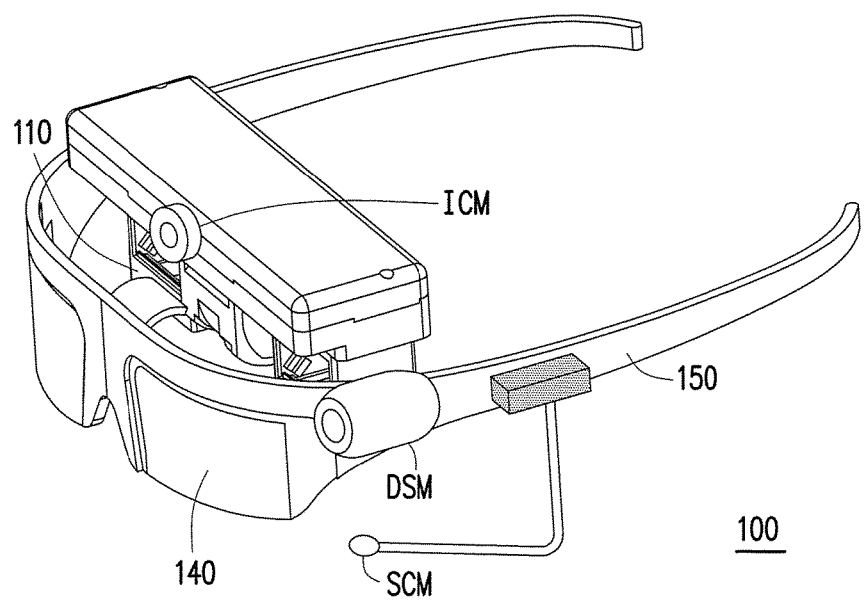
FIG. 9B to FIG. 9M are schematic diagrams of the exterior of different ambient light adjustment units of FIG. 1.
Figure 9C:
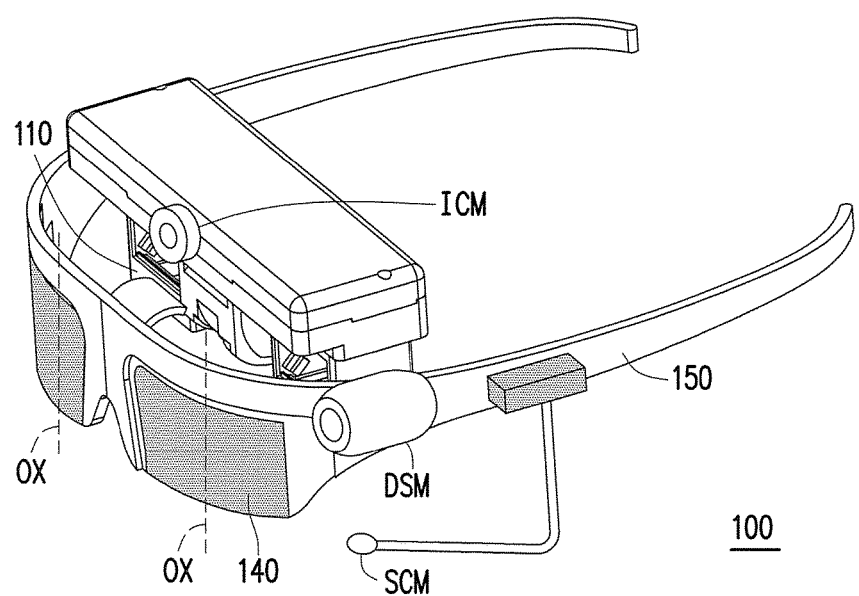
Figure 9D:
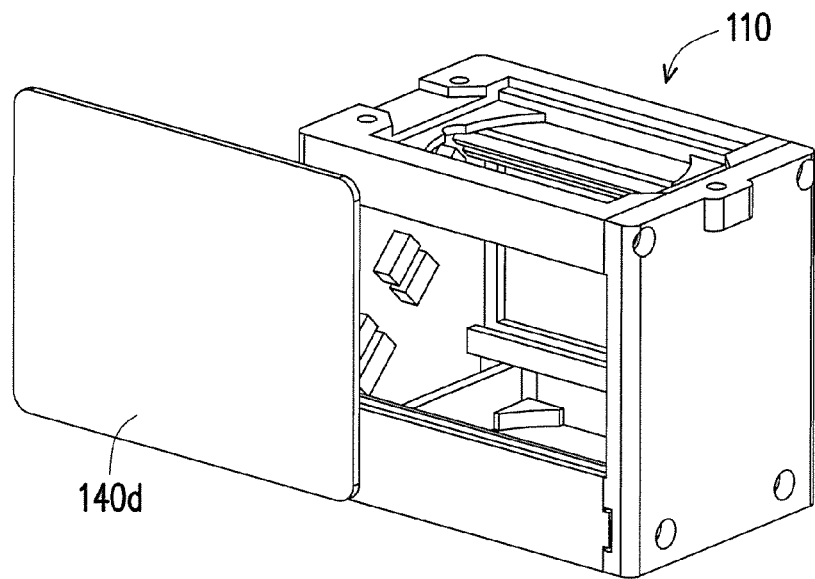
Figure 9E:
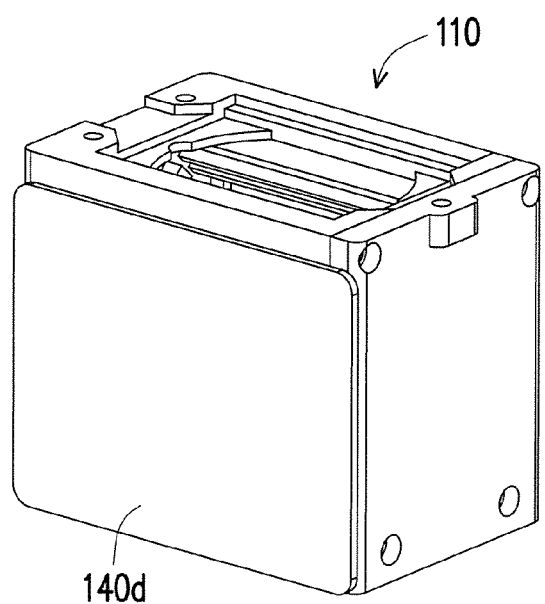
Figure 9F:
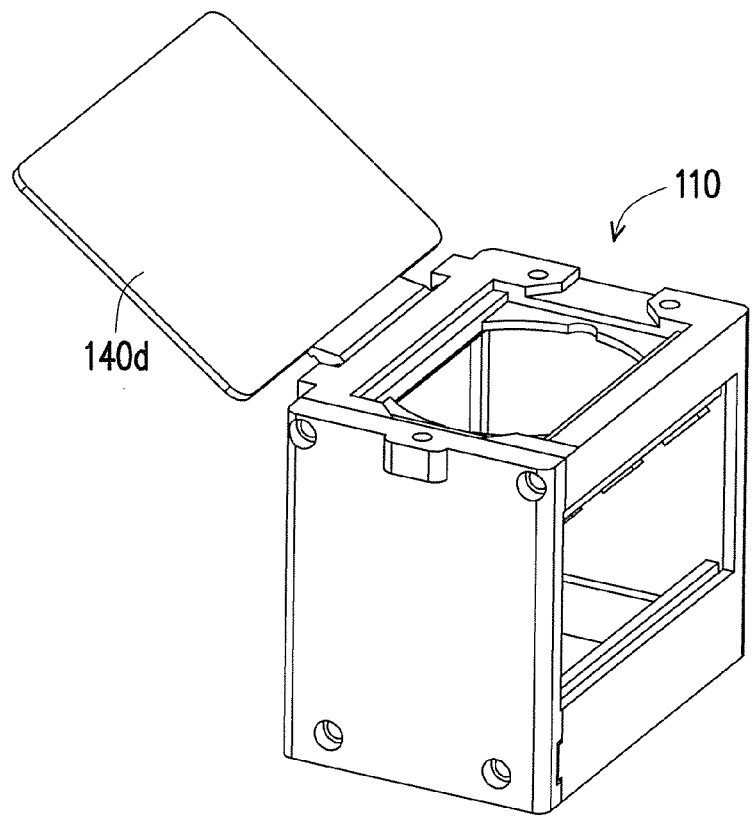
Figure 9G:
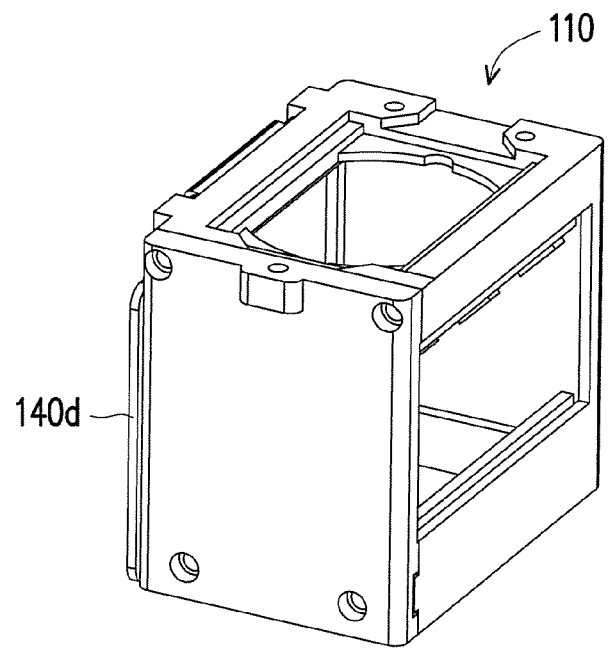
Figure 9H:
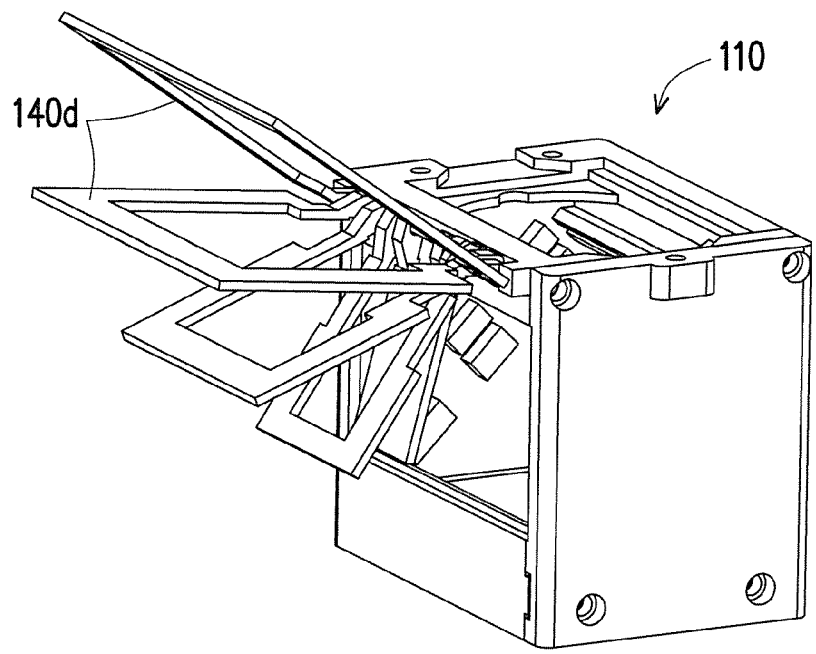
Figure 9I:
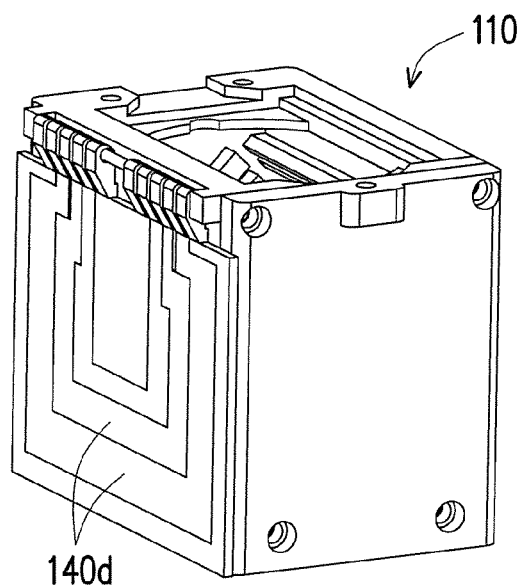
Figure 9J:
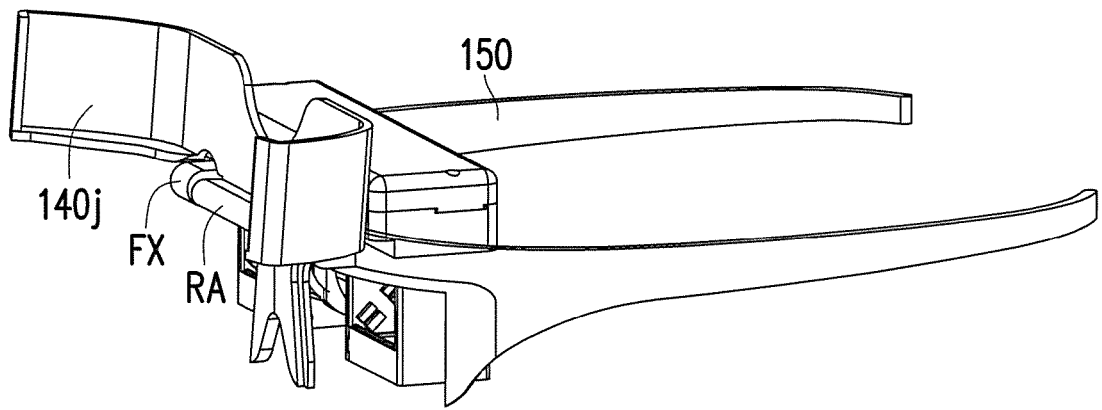
Figure 9K:
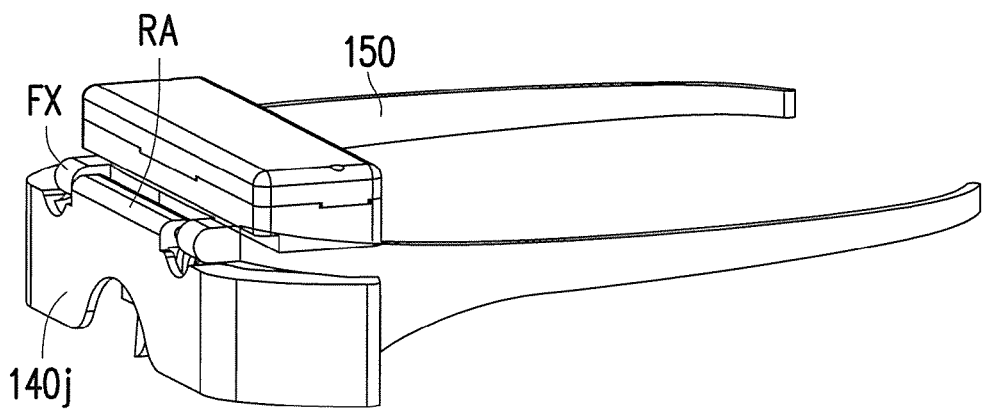
Figure 9L:
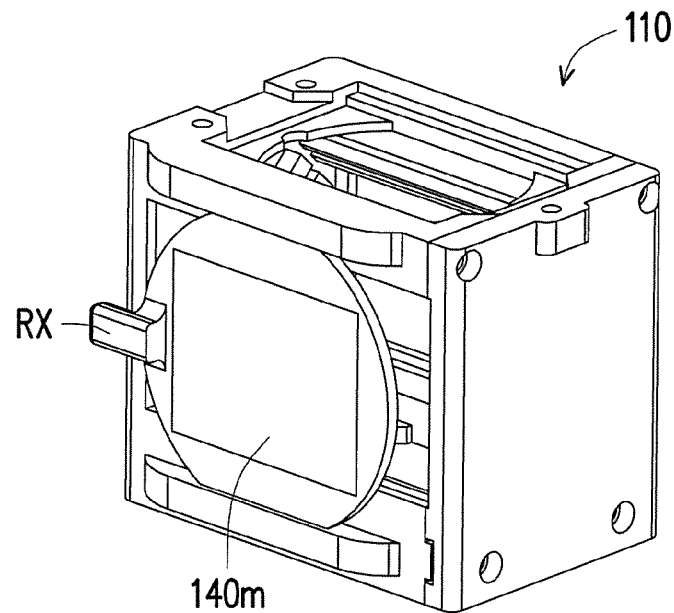
Figure 9M:
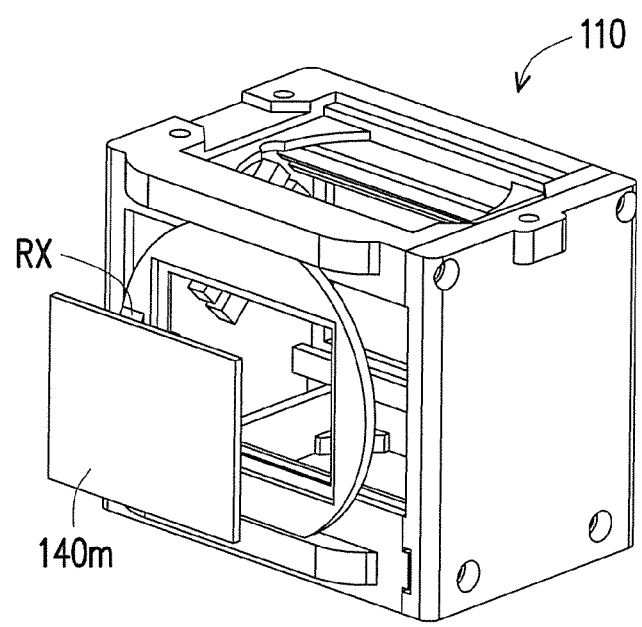
Figure 10:
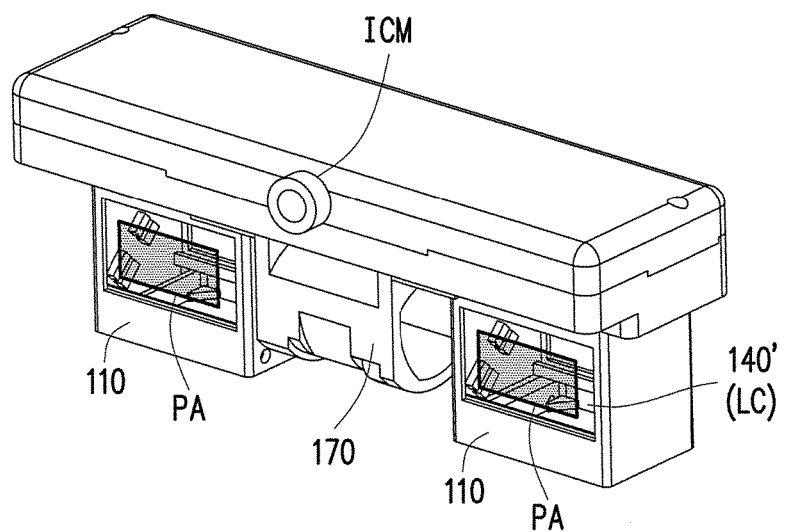
FIG. 10 is a schematic structural diagram of another ambient light adjustment unit of FIG. 1.

FIG. 9A to FIG. 10 are used to further explain the structural design and the function of the ambient light adjustment unit 140 below.

FIG. 9A is a schematic diagram of the blocking area of the object beam of the virtual image display system of FIG. 1. FIG. 9B and FIG. 9C are schematic diagrams of the exterior of different ambient light adjustment units of FIG. 1. Referring again to FIG. 2, FIG. 4, FIG. 9A, and FIG. 9B, in the present embodiment, the ambient light adjustment unit 140 is located on the transmission path of the object beam SB for adjusting the ratio of the brightness of at least a part of the object beam SB to the brightness of at least a part of the image beam IB. For instance, in the present embodiment, the ambient light adjustment unit 140 can include at least one filter and the filter can be used to adjust the brightness of at least a part of the object beam SB reflected to the eye EY and form a blocking area BA of the object beam in the eye EY. In this way, a clear area of the virtual image VI can be formed in the eye of the user UR to facilitate the surgery.

Moreover, as shown in FIG. 4 and FIG. 9C, since the beam splitting unit 115 of the present embodiment is also located on the transmission path of the object beam SB and between the ambient light adjustment unit 140 and the eye EY of the user UR, the ambient light adjustment unit 140 can also be a polarizer for adjusting the polarization state of at least a part of the object beam SB.

Moreover, although the ambient light adjustment unit 140 in each the embodiments of FIG. 9B and FIG. 9C is exemplified as disposed on the frame 150, the disclosure is not limited thereto. In other embodiments, the ambient light adjustment unit 140 can also be disposed on other components of the virtual image display system 100. FIG. 9D to FIG. 9M are used for further explanation below.

FIG. 9D to FIG. 9M are schematic diagrams of the exterior of different ambient light adjustment units of FIG. 1. Referring to FIG. 9D and FIG. 9E, in the present embodiment, the ambient light adjustment unit 140d can be any one of a filter, a polarizer, a shutter, and a photochromic lens to achieve a similar function to the ambient light adjustment unit 140 in each of the embodiments of FIG. 9B and FIG. 9C. Moreover, in the present embodiment, the ambient light adjustment unit 140d can be disposed on the outside of the virtual image display module 110 and can be adjusted and assembled in a sliding manner.

Moreover, referring to FIG. 9F and FIG. 9G, in the present embodiment, when the ambient light adjustment unit 140d is disposed on the outside of the virtual image display module 110, the ambient light adjustment unit 140d can also be assembled with other components of the virtual image display module 110 and be adjusted and opened/closed in a flipping manner.

Moreover, as shown in FIG. 9I and FIG. 9H, when the ambient light adjustment unit 140d is assembled on the virtual image display system 100 in a flipping manner, the ambient light adjustment unit 140d can further include a plurality of filters or any one of a filter, a polarizer, a shutter, and a photochromic lens, or a combination thereof. Moreover, the filters (or polarizers) have different sizes and can be assembled on one side of the virtual image display module 110 at the same time (as shown in FIG. 9I). In this way, the user UR can select one of the filters according to actual need to switch the size of the blocking area BA of the object beam to obtain the needed image frame.

Moreover, referring to FIG. 9J and FIG. 9K, the ambient light adjustment unit 140j of the present embodiment is similar to the ambient light adjustment unit 140 of FIG. 9B, and the difference between the two is as described below. In the present embodiment, the ambient light adjustment unit 140j can be any one of a filter, a polarizer, a shutter, and a photochromic lens having the shape of an eyepiece, and a fastening assembly FX can be disposed on the frame 150 to couple the frame 150 and the ambient light adjustment unit 140j. More specifically, the coupling site of the frame 150 with the ambient light adjustment unit 140j can also be designed to be a rotation axis RA suitable for axial engagement. In this way, the user UR can rotate or open the ambient light adjustment unit 140j (as shown in FIG. 9J).

Moreover, referring to FIG. 9L and FIG. 9M, the ambient light adjustment unit 140m of the present embodiment is similar to the ambient light adjustment unit 140d of FIG. 9D, and the difference between the two is as described below. In the present embodiment, the ambient light adjustment unit 140m includes a polarizer, and an optical axis OX of the polarizer can be adjusted according to the actual need of the user UR. For instance, as shown in FIG. 9M, the optical axis OX of the polarizer can be rotated through an external assembly RX. In this way, when the object beam SB passes through the beam splitting unit 115, the function of adjusting the brightness of at least a part of the object beam SB can also be achieved.

Moreover, it should also be mentioned that, although the ambient light adjustment unit 140 is exemplified as adjusting the brightness of at least a part of the object beam SB through a filter or a polarizer, the disclosure is not limited thereto. In other embodiments, the ambient light adjustment unit 140 can also achieve a similar effect through a liquid crystal unit LC. FIG. 10 is used for further explanation below.

FIG. 10 is a schematic structural diagram of another ambient light adjustment unit of FIG. 1. Referring to FIG. 10, the ambient light adjustment unit 140' of the present embodiment is similar to the ambient light adjustment unit 140 of each of FIG. 9A and FIG. 9B, and the difference is described below. In the present embodiment, the ambient light adjustment unit 140' further includes a liquid crystal unit LC. Specifically, in the present embodiment, the liquid crystal unit LC can be used to adjust the brightness or the polarization state of at least a part of the object beam SB passing through a partial area PA of the liquid crystal unit LC. Moreover, in the present embodiment, the virtual image display system 100 can also adjust the range of the partial area PA of the liquid crystal unit LC through the control unit 123 to switch the size of the blocking area BA of the object beam and achieve the function of adjusting the image contrast and the ratio of area size of the virtual image VI and the physical image.

Moreover, referring again to FIG. 3 and FIG. 9A (or FIG. 9B), in the present embodiment, the virtual image display system 100 can further include an image capture module ICM, a displacement sensing module DSM, and a voice capture module SCM disposed on the frame 150. Specifically, the image capture module ICM, the displacement sensing module DSM, and the voice capture module SCM are all electrically connected to the control unit 123 and the user UR can command the virtual image display system 100 to execute the needed function according to actual need through the image capture module ICM, the displacement sensing module DSM, or the voice capture module SCM. For instance, the function includes executing functions such as visual compensation, switching the focusing sharpness, size, location, or contents (such as arrow indication of surgical image, local positioning and magnification of surgical image, recording of surgical image, replay and slow motion, frame freeze, screen printing, and timely edit and input of medical records) of the image frame, or adjustment of ambient light.

Specifically, the image capture module ICM can be used to capture the gesture image of the user UR and generate gesture image information. Then, the gesture image information can be transmitted to the control unit 123 such that the control unit 123 executes a function corresponding to the gesture image information according to the gesture image information. In this way, the user UR can command the virtual image display system 100 to execute the above functions according to actual need. Moreover, the displacement sensing module DSM can include a gravity sensor, a gyroscope, or any combination thereof. When the head of the user UR performs a specific rotation or movement, the displacement sensing module DSM can be used for identifying the direction of rotation and the speed of the frame 150 and generating displacement information. Moreover, the displacement information is transmitted to the control unit 123, and the control unit 123 executes a function corresponding to the displacement information according to the displacement information. Moreover, the voice capture module SCM can also be used to capture voice information emitted by the user UR. The voice information is transmitted to the control unit 123 and the control unit 123 executes a function corresponding to the voice information according to the voice information. In this way, the user UR can also make the virtual image display system 100 execute the needed function according to actual need through different gestures, head movements, or voice commands. In this way, the interaction between the user UR and the virtual image display system 100 can be facilitated.

Moreover, in the present embodiment, when the ambient light adjustment unit 140j and the image capture module ICM, the displacement sensing module DSM, and the voice capture module SCM are used in combination, the user UR can also make the virtual image display system 100 adjust the opening or the rotation angle of the ambient light adjustment unit 140j according to actual need through different gestures, head movements, or voice commands to adapt to the need of different surgical situations. For instance, the user mode can be defined to be, when the user UR raises his head, the ambient light adjustment unit 140j can cover the visual field of the user (i.e., ambient light adjustment unit 140j and virtual image display system 100 have smaller angle or angle is 0) such that the virtual image VI can be clearly seen. When the user UR lowers his head, the ambient light adjustment unit 140j is raised to avoid covering the visual field of the user (i.e., ambient light adjustment unit 140j and virtual image display system 100 have larger angle) such that the surrounding environment can be clearly seen.

Figure 11A:
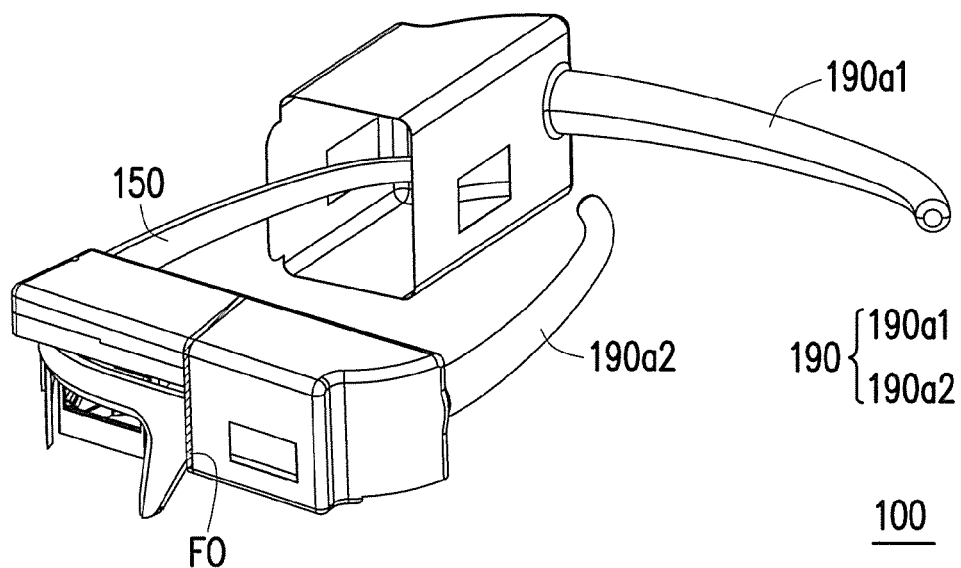
FIG. 11A and FIG. 11B are schematic diagrams of different casings adapted for storing the virtual image display system of FIG. 1.
Figure 11B:
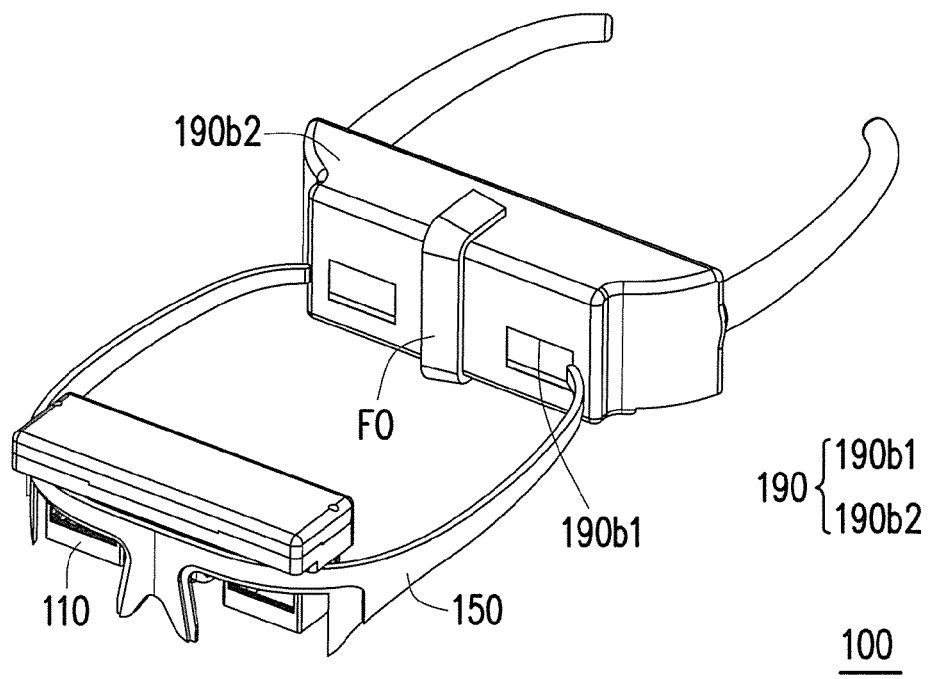

FIG. 11A and FIG. 11B are schematic diagrams of different casings adapted for storing the virtual image display system of FIG. 1. Referring to FIG. 11A and FIG. 11B, in the present embodiment, the virtual image display system 100 further includes a casing 190 and the casing 190 is made of an antibacterial material or a sterilizing material. Specifically, the casing 190 has an accommodating space. When the virtual image display system 100 needs to be used in a sterile environment, the casing 190 can be used to accommodate components such as the image display unit 111, the beam splitting unit 115, the reflection unit 114, the ambient light adjustment unit 140, and the frame 150 of the virtual image display system 100 and be worn by the user UR.

Moreover, in the present embodiment, the casing 190 is a removable casing. For instance, as shown in FIG. 11A, the casing 190 can be divided into left and right casings 190a1 and 190a2 capable of respectively accommodating the left and right portions of components of the virtual image display system 100. Moreover, the left and right casings 190a1 and 190a2 are in contact and are combined with each other by using a fixing object FO (such as Velcro). Alternatively, the casing 190 can be divided into a front cover 190b1 and a rear frame 190b2 capable of setting the end of the frame 150 into the rear frame 190b2 of the casing 190 and penetrating to the bottom. Then, the front cover 190b1 of the casing 190 is used to cover the opening of the rear frame 190b2 and a fixing object FO (such as Velcro) is used for fixing to complete the assembly of the virtual image display system 100.

Based on the above, since the virtual image display system 100 of the present embodiment is lightweight and convenient to wear, the surgeon can freely adjust the viewing angle during surgery to monitor the surgical screen, and therefore an additional monitor is not needed and the surgeon does not need to stare at the same viewing angle for long periods of time. As a result, the cost of the instrument is lowered and fatigue to the eyes, the neck, and the shoulders and physical burden of the surgeon are reduced. Moreover, for the less-experienced surgeons, the virtual image display system 100 of the present embodiment can help to control of the sense of direction of the surgical devices SD, therefore facilitating learning and proficiency of surgical techniques, and thereby shortening the time of surgical training. Moreover, the virtual image display system 100 of the embodiments of the disclosure is easy to operate, and therefore the operating time of long surgeries can be reduced and the risk of surgery is also reduced.

Figure 12:
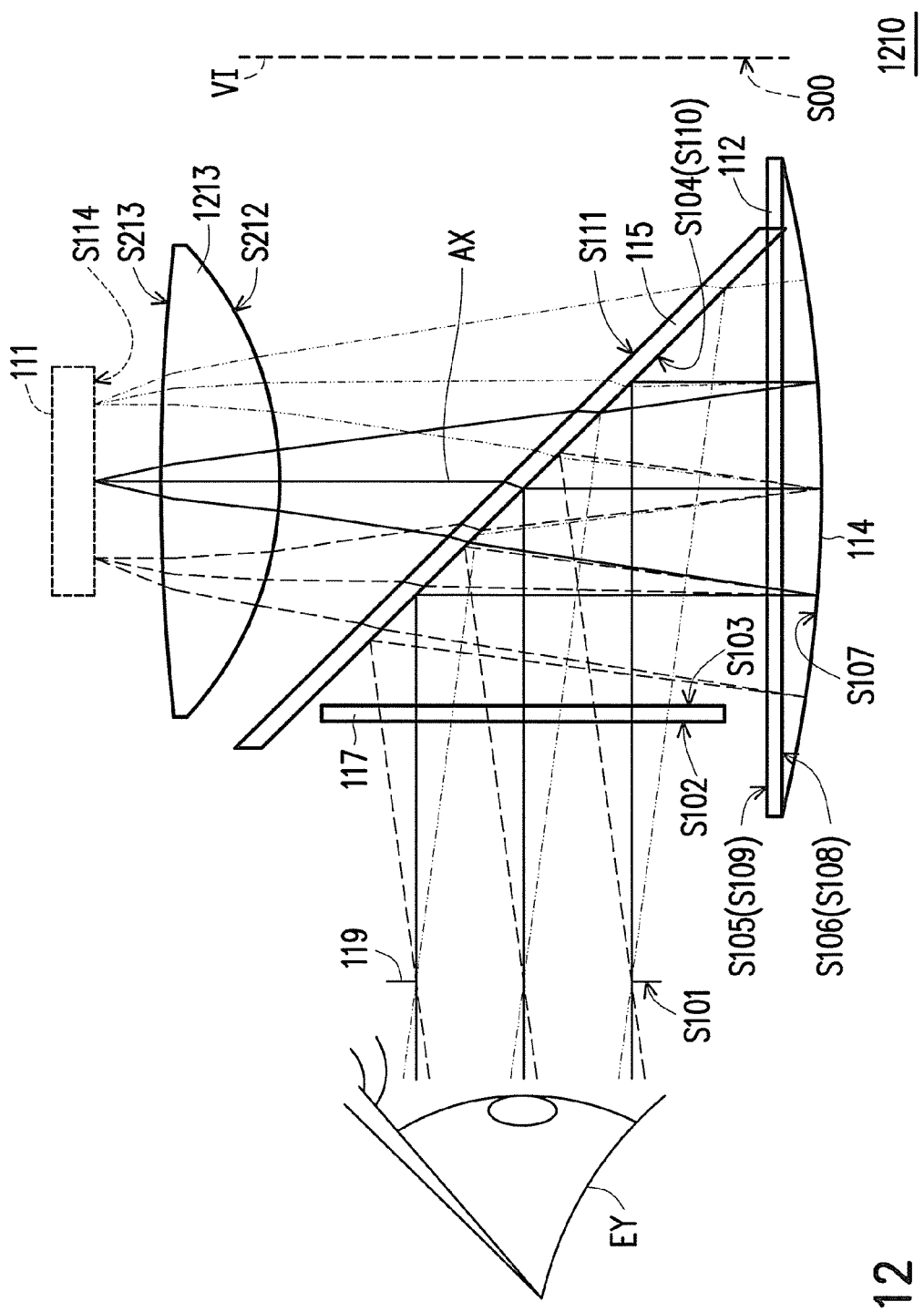
FIG. 12 is a schematic diagram of the architecture of a virtual image display module of another embodiment of the disclosure.

FIG. 12 is a schematic diagram of the architecture of a virtual image display module of another embodiment of the disclosure. Referring to FIG. 12, the virtual image display module 1210 of the present embodiment is similar to the virtual image display module 110 of FIG. 6A, and the difference between the two is as described below. In the present embodiment, the motion compensation lens group 1213 of the virtual image display module 1210 is a biconvex lens. In particular, the detailed optical parametric design of the virtual image display module 1210 is as shown in Table 2A:

TABLE 2A

| Surface | Surface type | Radius of curvature | Distance | Material | Note |
| --- | --- | --- | --- | --- | --- |
| S00 | Sphere | Infinity | −3000.00 | | Virtual image VI |
| S101 | Sphere | Infinity | 10.00 | | Exit pupil 119 |
| S102 | Sphere | Infinity | 0.70 | BK7 | Sheet glass 117 |
| S103 | Sphere | Infinity | 8.00 | | |
| S104 | Sphere | Infinity | −9.00 | | Beam splitting unit 115 |

TABLE 2A-continued

| Surface | Surface type | Radius of curvature | Distance | Material | Note |
|---|---|---|---|---|---|
| S105 | Sphere | Infinity | −0.55 | BK7 | Wave plate 112 |
| S106 | Sphere | Infinity | −1.50 | | |
| S107 | Aspheric surface | 51.89682 | 1.50 | | Reflecting unit 114 |
| S108 | Sphere | Infinity | 0.55 | BK7 | Wave plate 112 |
| S109 | Sphere | Infinity | 9.00 | | |
| S110 | Sphere | Infinity | 0.99 | BK7 | Beam splitting unit 115 |
| S111 | Sphere | Infinity | 6.33 | | |
| S212 | Sphere | 17.32028 | 3.8 | BK7 | Motion compensation lens group 1213 |
| S213 | Sphere | −51.864 | 3.73 | | |
| S114 | Sphere | Infinity | 0.00 | | Image display unit 111 |

In Table 2A, the unit of the radius of curvature is millimeter (mm), the surfaces S212 and S213 represent the two surfaces of the motion compensation lens group 1213 (i.e., biconvex lens), and the meaning of each of the other surfaces and materials is as described in Table 1A and is not repeated herein. Moreover, a number of important parameter values of the virtual image display module 1210 such as field of view, f-number, lateral color aberration, and the ratio of the diameter of the reflection unit 114 to the diameter of the exit pupil 119 are also the same as the virtual image display module 1210 and are not repeated herein. Moreover, the asphericity of the aspheric surface (such as surface S107) is as shown in Table 2B:

In Table 2B, the formula of the aspheric surface (such as surface S107) is the same as the formula for Table 1B, and the physical meaning of each of the parameters is as described in Table 1B and is not repeated herein.

Figure 13:
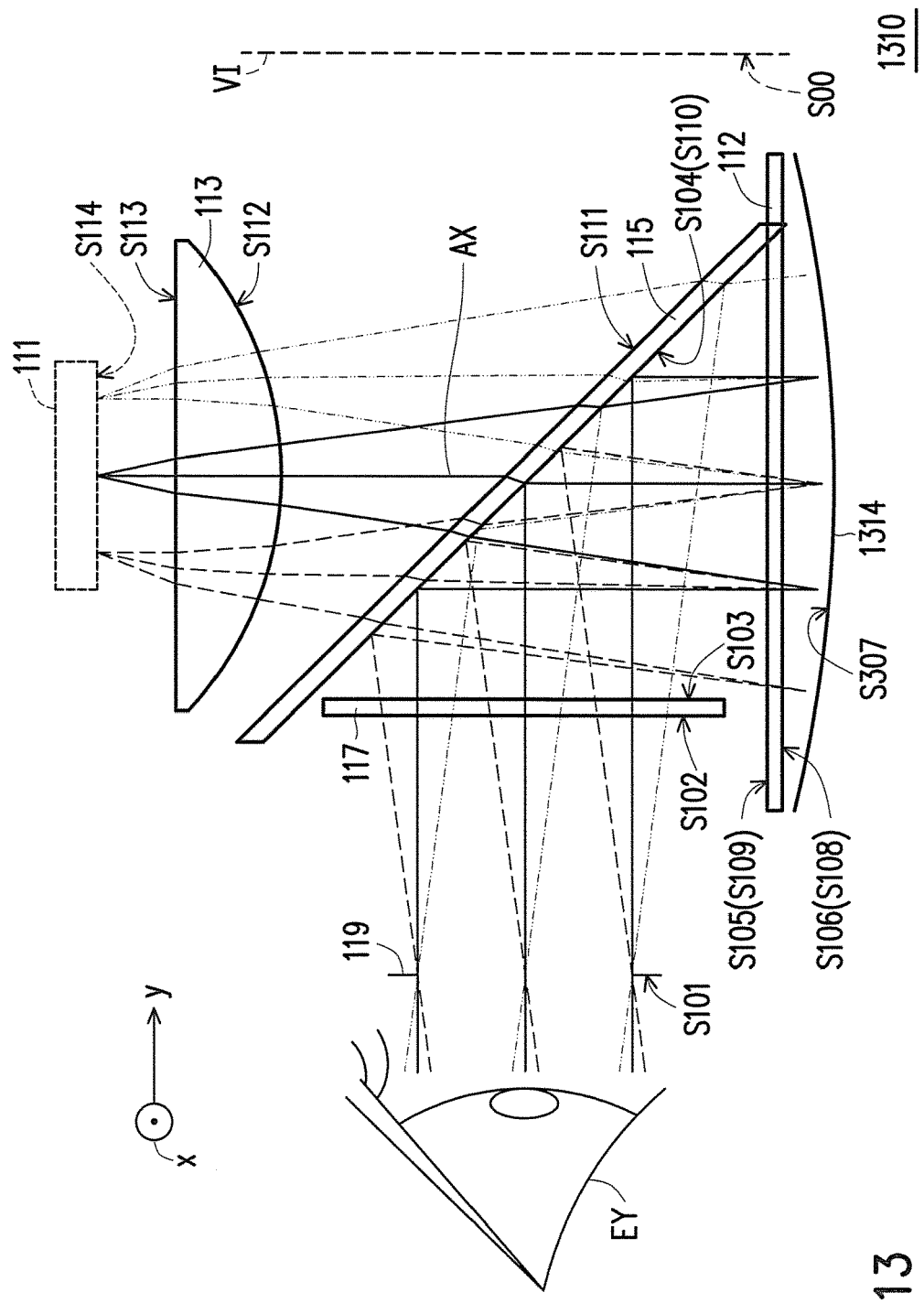
FIG. 13 is a schematic diagram of the architecture of a virtual image display module of yet another embodiment of the disclosure.

FIG. 13 is a schematic diagram of the architecture of a virtual image display module of yet another embodiment of the disclosure. Referring to FIG. 13, the virtual image display module 1310 of the present embodiment is similar to the virtual image display module 110 of FIG. 6A, and the difference between the two is as described below. In the present embodiment, the reflection unit 1314 of the virtual image display module 1310 is an anamorphic concave mirror. In particular, the detailed optical parametric design of the virtual image display module 1310 is as shown in Table 3A:

TABLE 3A

| Surface | Surface type | Radius of curvature Ry | Radius of curvature Rx | Distance | Material | Note |
|---|---|---|---|---|---|---|
| S00 | Sphere | Infinity | Infinity | −3000.00 | | Virtual image VI |
| S101 | Sphere | Infinity | Infinity | 5.00 | | Exit pupil 119 |
| S102 | Sphere | Infinity | Infinity | 0.70 | BK7 | Sheet glass 117 |
| S103 | Sphere | Infinity | Infinity | 8.50 | | |
| S104 | Sphere | Infinity | Infinity | −9.25 | | Beam splitting unit 115 |
| S105 | Sphere | Infinity | Infinity | −0.55 | BK7 | Wave plate 112 |
| S106 | Sphere | Infinity | Infinity | −1.50 | | |
| S307 | Anamorphic aspheric surface | 52.68 | 52.93 | 1.50 | | Reflecting unit 1314 |
| S108 | Sphere | Infinity | Infinity | 0.55 | BK7 | Wave plate 112 |
| S109 | Sphere | Infinity | Infinity | 9.25 | | |
| S110 | Sphere | Infinity | Infinity | 0.99 | BK7 | Beam splitting unit 115 |
| S111 | Sphere | Infinity | Infinity | 7.03 | | |
| S112 | Sphere | 12.98323 | Infinity | 3.00 | BK7 | Motion compensation lens group 113 |
| S113 | Sphere | Infinity | Infinity | 3.68 | | |
| S114 | Sphere | Infinity | Infinity | 0.00 | | Image display unit 111 |

TABLE 2B

| | S107 |
|---|---|
| Radius of lens | 51.896817 |
| Conic constant (K) | −11.33484 |
| 4th order parameter ($A_4$) | $1.07 \times 10^{-05}$ |
| 6th order parameter ($A_6$) | $-4.05 \times 10^{-08}$ |
| 8th order parameter ($A_8$) | $2.06 \times 10^{-10}$ |
| 10th order parameter ($A_{10}$) | $-5.76 \times 10^{-13}$ |

In Table 3A, the radius of curvature Rx is close to the radius of curvature in the x direction at the optical axis AX, the radius of curvature Ry is close to the radius of curvature in the y direction at the optical axis AX, and the unit of each thereof is millimeter (mm). Moreover, the meaning of each of the surfaces and materials is as described in Table 1A and is not repeated herein. Moreover, a number of important parameter values of the virtual image display module 1310 are exemplified below. In the present embodiment, the field of view of the virtual image display module 1310 is 30 degrees, the f-number is 2.53, the lateral color aberration is 9.4 μm, and the ratio of the diameter of the reflection unit 114 to the diameter of the exit pupil 119 is 2.56. Moreover, the asphericity of the aspheric surface (such as surface S307) is as shown in Table 3B below:

TABLE 3B

|  | S107 |
| --- | --- |
| Reciprocal of radius of curvature (cx) | $1.90 \times 10^{-02}$ |
| Conic coefficient (ky) | 0.487827339 |
| 4th order parameter (AR) | $-5.48 \times 10^{-09}$ |
| 6th order parameter (BR) | $4.05 \times 10^{-15}$ |
| Reciprocal of radius of curvature (CX) | $1.89 \times 10^{-02}$ |
| Conic coefficient (KX) | 0.308085726 |
| 4th order parameter (AP) | $7.56 \times 10^{+00}$ |
| 6th order parameter (BP) | $-1.11 \times 10^{+02}$ |

In the present embodiment, the surface S307 is one type of free-form surfaces and the function of the aspheric surface is as shown below:

$$Z = \frac{c_x X^2 + c_y Y^2}{1 + \sqrt{1 - (1+k_x)c_x^2 X^2 - (1+k_y)c_y^2 Y^2}} +$$

$$AR[(1-AP)X^2 + (1+AP)Y^2]^2 + BR[(1-BP)X^2 + (1+BP)Y^2]^3$$

In the formula, Z is the sag in the direction of the optical axis AX, $C_x$ is the reciprocal of the radius of the osculating sphere in the x direction, that is, close to the reciprocal of the radius of curvature (such as the radius of curvature in the x direction of S307 in Table 1) in the x direction at the optical axis AX, $C_y$ is the reciprocal of the radius of the osculating sphere in the y direction, that is, close to the reciprocal of the radius of curvature (such as the radius of curvature in the y direction of S307 in Table 1) in the y direction at the optical axis AX. $k_x$ is the conic coefficient in the x direction and $k_y$ is the conic coefficient in the y direction. X is the height of the biconic surface in the x direction, that is, the height from the center of the lens to the edge of the lens along the x direction, and Y is the height of the biconic surface in the y direction, that is, the height from the center of the lens to the edge of the lens along the y direction. Moreover, AR, BR, AP, and BP are aspheric coefficients.

Moreover, in the previous embodiments, the user UR can also adjust the distance from the image display unit 111 of each of the virtual image display modules 1210 and 1310 to the reflection unit 114 through the control unit 123 according to personal habits to correspondingly change the imaging position and the size of the image frame of the virtual image VI to facilitate the use of the virtual image display system 100 or perform relevant visual compensation. In the previous embodiments, the relationship between the distance of the image display unit 111 of each of the virtual image display modules 1210 and 1310 and the reflection unit 114 (or reflection unit 1314) and the imaging position and the size of the image frame of the virtual image VI is also as shown in Table 1C and is not repeated herein. The relationship between the location of each of the image display unit 111 and the motion compensation lens group 113 (or motion compensation lens group 1213) of each of the virtual image display modules 1210 and 1310 relative to the beam splitting unit 115 and the refractive power of the eye EY of the user UR is also as shown in Table 1D and Table 1E and is not repeated herein. The relationship between the relative position of each of the image display unit 111 and the motion compensation lens group 113 (or motion compensation lens group 1213) and the refractive power of the eye EY of the user UR is as described in Table 1F and Table 1G and is not repeated herein.

Figure 14A:
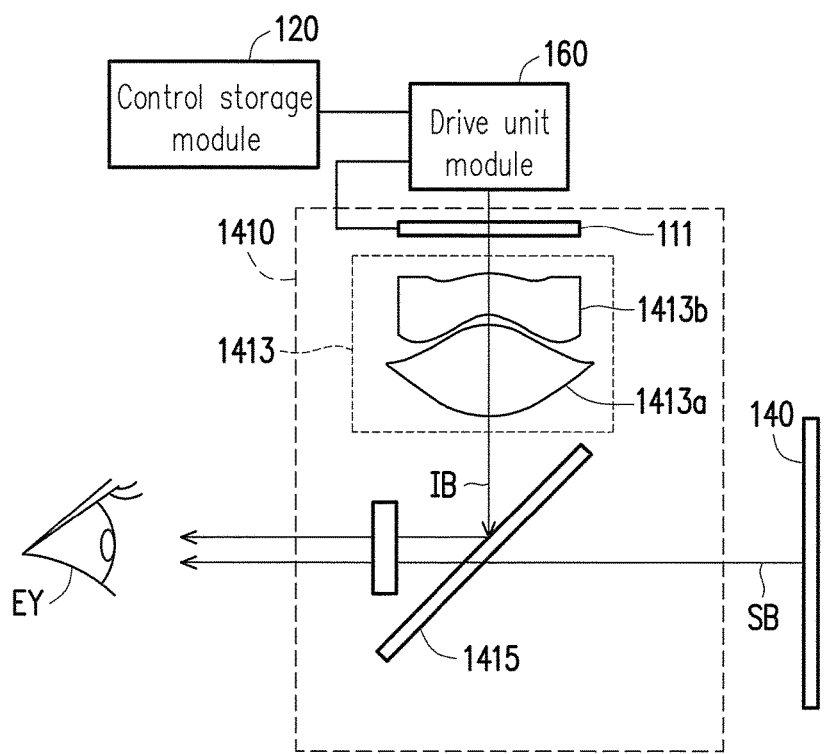
FIG. 14A is a schematic diagram of the architecture of a virtual image display system of still yet another embodiment of the disclosure.
Figure 14B:
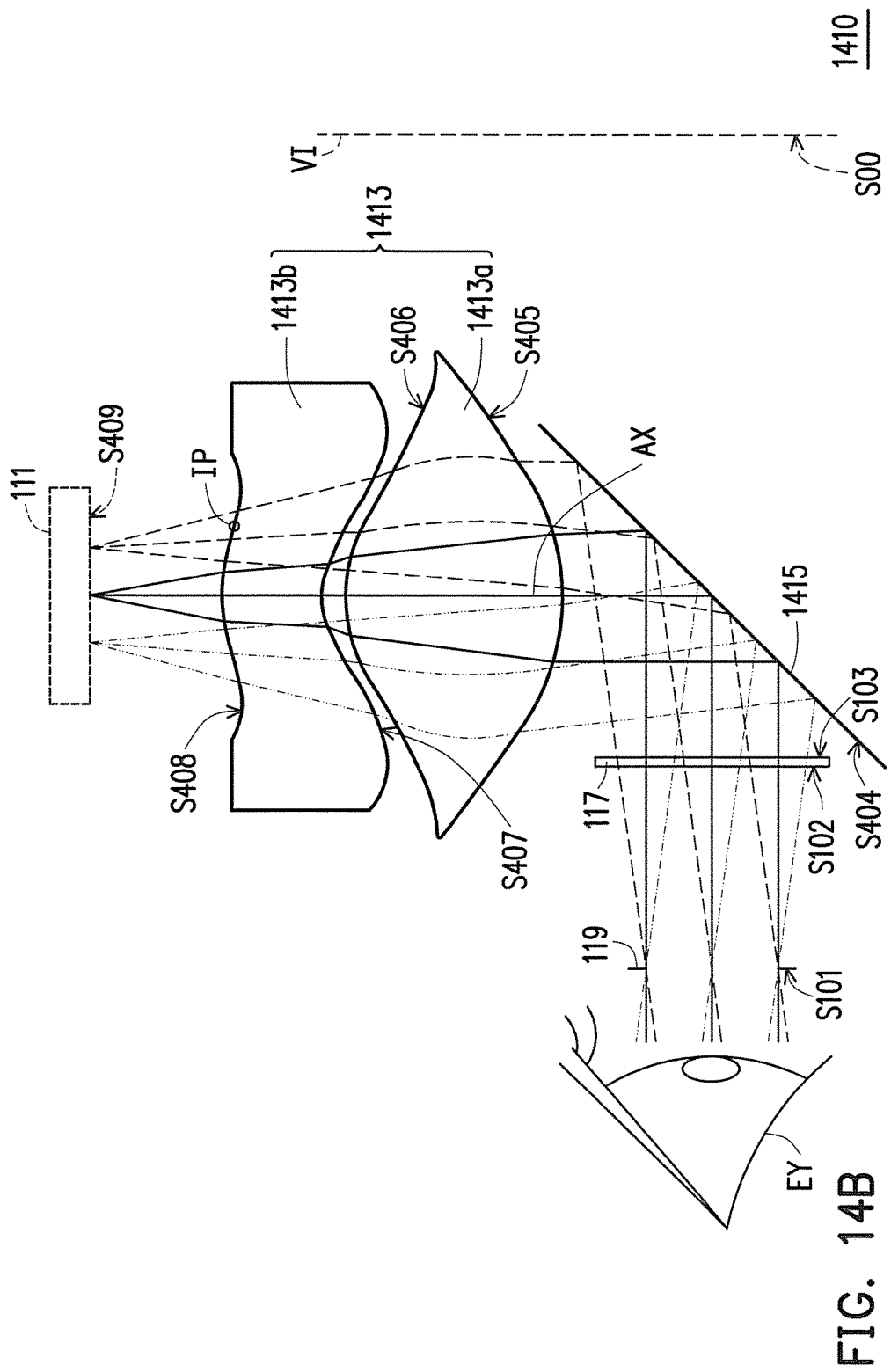
FIG. 14B is a schematic diagram of the architecture of a virtual image display module of FIG. 14A.

FIG. 14A is a schematic diagram of the architecture of a virtual image display system of still yet another embodiment of the disclosure. FIG. 14B is a schematic diagram of the architecture of a virtual image display module of FIG. 14A. Referring to FIG. 14A and FIG. 14B, the virtual image display system 200 of the present embodiment is similar to the virtual image display system 100 of FIG. 4, and the difference between the two is as described below. Specifically, in the present embodiment, the beam splitting unit 1415 of the virtual image display system 200 is a partially-transmissive partially-reflective beam splitting element, and therefore the effect of partial light penetration and partial reflection can be provided to the incident light. For instance, in the present embodiment, the beam splitting unit 1415 can be an optical coated element having 30-70% transmittance and 30-70% reflectance. The parameter range of the ratio of the transmittance to the reflectance is only used as an aid to explain the present embodiment, and the endpoint values and the size of the range thereof are not used to limit the disclosure.

More specifically, as shown in FIG. 14A, the beam splitting unit 1415 of the virtual image display system 200 can cause at least a part of the object beam SB to pass through the beam splitting unit 1415 and be transmitted to the eye EY. Moreover, at least a part of the image beam IB emitted by the image display unit 111 can also be reflected by the beam splitting unit 1415 and be transmitted to the eye EY. In other words, the beam splitting unit 1415 of the virtual image display system 200 can also achieve a similar function to the combination of the beam splitting unit 115, the reflection unit 114, and the wave plate 112 included in the virtual image display module 110, and can allow the user UR to observe the physical image in front of the virtual image display system 200 and the virtual image VI to be displayed by the image beam IB provided by the image display unit 111 at the same time.

Moreover, in the present embodiment, since the beam splitting unit 1415 of the present embodiment does not achieve the function of beam splitting by selecting the polarization state of incident light, the image display unit 111 can not be limited to the combination of including the light source module 111a and the display panel 111b (such as liquid crystal display panel 111b or a liquid-crystal-on-silicon display) and can also be a display apparatus such as an organic light emitting diode display panel, a light emitting diode display panel, or a field emission display panel.

Moreover, in the present embodiment, as shown in FIG. 14A, the motion compensation lens group 1413 includes at least two aspheric lenses to achieve a good overall optical design effect and maintain good image quality. In the following, the overall design of the optical structure of the virtual image display module 1410 is further explained.

Specifically, as shown in FIG. 14B, in the present embodiment, the motion compensation lens group 1413 includes a first lens 1413a and a second lens 1413b arranged in sequence from the beam splitting unit 1415 toward the image display unit 111, and the refractive power of the first lens 1413a and the second lens 1413b are respectively positive and negative. More specifically, the first lens 1413a and the second lens 1413b are aspheric lenses and the first lens 1413a and the second lens 1413b are respectively a biconvex lens and a convex-concave lens having a convex surface facing the image display unit 111. Moreover, a cut curve obtained by cutting the convex surface of the second lens 1413b facing the image display unit 111 along an optical axis AX of the second lens 1413b can have at least one inflection point IP, and the inflection point IP is where the sign of the slope derivative of the obtained cut curve changes.

In the present embodiment, the material of each of the first lens 1413a and the second lens 1413b is, for instance, plastic. However, since the general lens generates dispersion to different wavelengths, visible light and infrared light can not focus on planes of the same distance, thereby causing an effect of color aberration. To overcome the issue of color aberration, in the present embodiment, the Abbe number of the first lens 1413a can be greater than 40 and the Abbe number of the second lens 1413b can be less than 40 to reduce the effect of color aberration caused by optical elements to the image beam IB. As a result, the image quality can be further enhanced.

More specifically, as shown in FIG. 14B, in the present embodiment, the image display unit 111, the motion compensation lens group 1413, and the beam splitting unit 115 can be designed together to determine the imaging properties of the virtual image VI. In particular, the detailed optical parametric design is as shown in Table 4A:

materials represents a polyester having an index of refraction of about 1.633 and an Abbe number of about 23.3. Z-E48R represents another optical glass having an index of refraction of about 1.53 and an Abbe number of about 55. The numbering of the material column is the material numbering commonly used in the industry. Moreover, the surfaces S00 to S409 in Table 4A are respectively as illustrated in FIG. 14B and represent the surfaces the beam passes through in sequence on the path from the virtual image VI to the image display unit 111.

More specifically, the surface S00 represents the location of the virtual image VI and S409 represents the display surface of the image display unit 111. Moreover, the meaning of each of the surfaces S101, S102, and S103 is as described in Table 1A and is not repeated herein. Next, the surface S404 represents the surface of the beam splitting unit 1415 facing the sheet glass 117. The surfaces S405 and S406 represent the two surfaces of the first lens 1413a of the motion compensation lens group 1413. The surfaces S407 and S408 represent the two surfaces of the second lens 1413b of the motion compensation lens group 1413.

Moreover, a number of important parameter values of the virtual image display module 1410 are exemplified below. In the present embodiment, the field of view of the virtual image display module 1410 is 30 degrees, the f-number is 2.54, the lateral color aberration is 11 μm, and the ratio of the

TABLE 4A

| Surface | Surface type | Radius of curvature | Distance | Material | Note |
|---|---|---|---|---|---|
| S00 | Sphere | Infinity | −3000.00 | | Virtual image VI |
| S101 | Sphere | Infinity | 12.00 | | Exit pupil 119 |
| S102 | Sphere | Infinity | 0.70 | BK7 | Sheet glass 117 |
| S103 | Sphere | Infinity | 10.00 | | |
| S404 | Sphere | Infinity | −9.00 | | Beam splitting unit 1415 |
| S405 | Aspheric surface | $-1.26 \times 10^{+01}$ | −13.06 | 'Z-E48R' | First lens 1413a |
| S406 | Aspheric surface | $7.45 \times 10^{+00}$ | −1.35 | | |
| S407 | Aspheric surface | 5.0092159 | −6.00 | 'OKP4HT' | Second lens 1413b |
| S408 | Aspheric surface | $1.03 \times 10^{+01}$ | −8.79 | | |
| S409 | Sphere | Infinity | $0.00 \times 10^{+00}$ | | Image display unit 111 |

In Table 4A, the unit of the radius of curvature is millimeter (mm), and BK7 in the materials represents an optical glass having an index of refraction of about 1.517 and an Abbe number of about 64.2. 'OKP4HT' in the diameter of the reflection unit 114 to the diameter of the exit pupil 119 is 3.44. Moreover, the asphericity of each of the aspheric surfaces (such as surfaces S405, S406, S407, and S408) is as shown in Table 4B below:

TABLE 4B

| | S405 | S406 | S407 | S408 |
|---|---|---|---|---|
| Radius of lens | −0.07965 | 0.1342857 | 0.199632 | 0.097246 |
| Conic constant (K) | −12.5554 | 7.4468084 | −1.815292 | 0 |
| 4th order parameter ($A_4$) | $-8.34 \times 10^{-01}$ | $-1.01 \times 10^{+00}$ | $-3.98 \times 10^{-04}$ | $-7.76 \times 10^{-04}$ |
| 6th order parameter ($A_6$) | $1.09 \times 10^{-05}$ | $-3.62 \times 10^{-04}$ | $1.74 \times 10^{-06}$ | $2.89 \times 10^{-06}$ |
| 8th order parameter ($A_8$) | $2.40 \times 10^{-07}$ | $1.32 \times 10^{-06}$ | $-4.54 \times 10^{-09}$ | $-3.09 \times 10^{-08}$ |
| 10th order parameter ($A_{10}$) | $0.00 \times 10^{+00}$ | $0.00 \times 10^{+00}$ | $0.00 \times 10^{+00}$ | $0.00 \times 10^{+00}$ |

In Table 4B, the formula of each of the aspheric surfaces (such as surfaces S405, S406, S407, and S408) is the same as the formula for Table 1B, and the physical meaning of each of the parameters is as described in Table 1B and is not repeated herein.

Moreover, in the present embodiment, the user UR can also adjust the relative position of each of the image display unit 111 and the motion compensation lens group 1413 of the virtual image display module 1410 through the control unit 123 according to personal habits to correspondingly change the imaging position and the size of the image frame of the virtual image VI to facilitate the use of the virtual image display system 200 or perform relevant visual compensation. More specifically, in the present embodiment, the image display unit 111 can move relative to the motion compensation lens group 1413 along the optical axis AX to adjust the imaging position and the size of the image frame of the virtual image VI. In particular, the relationship between the relative position of the image display unit 111 and the motion compensation lens group 1413 and the imaging position and the size of the image frame of the virtual image VI is as shown in Table 4C below:

TABLE 4C

| Surface | Distance (mm) | Size of image frame (inch) |
| --- | --- | --- |
| S00 | −250 | 5.5" |
| S408 | −7.14 | |
| S00 | −500 | 11" |
| S408 | −8.07 | |
| S00 | −2000 | 22" |
| S408 | −8.5 | |
| S00 | −2000 | 44" |
| S408 | −8.72 | |
| S00 | −3000 | 66" |
| S408 | −8.79 | |
| S00 | −4000 | 88" |
| S408 | −8.82 | |
| S00 | −5000 | 1410" |
| S408 | −8.84 | |
| S00 | −6000 | 132" |
| S408 | −8.85 | |

In Table 4C, the distance of the surface S00 represents the location of the virtual image VI seen by the eye of the user UR. In other words, in the present embodiment, the location of the eye EY and the location of the exit pupil 119 are similar. The distance of the surface S408 represents the distance between the surface S408 of the second lens 1413b of the motion compensation lens group 1413 facing the image display unit 111 and the display surface (i.e., surface S409) of the image display unit 111 along the direction of the optical axis AX. In the present embodiment, the control unit 123 can adjust the relative position of the image display unit 111 and the motion compensation lens group 1413 according to actual need. In this way, the corresponding imaging position or size of the image frame of the virtual image VI can be obtained. Moreover, in the present embodiment, when the distance of the surface S408 is 8.924 mm, the largest size of the image frame of the virtual image VI can be obtained.

Moreover, the relationship between the relative position of the image display unit 111 and the motion compensation lens group 1413 and the refractive power of the eye EY of the user UR is as described in Table 4D and Table 4E:

TABLE 4D

| Myopia | | | | | |
| --- | --- | --- | --- | --- | --- |
| Virtual image located 3 m in front of eye | | | Virtual image located 50 cm in front of eye | | |
| Refractive power | Degree | Distance of surface S408 (mm) | Refractive power | Degree | Distance of surface S408 (mm) |
| −1 D | −200 | −8.37 | −1 D | −200 | −7.64 |
| −2 D | −200 | −7.94 | −2 D | −200 | −7.21 |
| −3 D | −300 | −7.51 | −3 D | −300 | −6.77 |
| −4 D | −400 | −7.08 | −4 D | −400 | −6.32 |
| −5 D | −500 | −6.64 | −5 D | −500 | −5.87 |
| −6 D | −600 | −6.18 | −6 D | −600 | −5.40 |
| −7 D | −700 | −5.72 | −7 D | −700 | −4.93 |
| −8 D | −800 | −5.28 | −8 D | −800 | −4.48 |
| −9 D | −900 | −4.81 | −9 D | −900 | −4.00 |
| −10 D | −2000 | −4.34 | −10 D | −2000 | −3.52 |
| −15 D | −1500 | −1.80 | −15 D | −1500 | −0.90 |

TABLE 4E

| Hyperopia | | | | | |
| --- | --- | --- | --- | --- | --- |
| Virtual image located 3 m in front of eye | | | Virtual image located 50 cm in front of eye | | |
| Refractive power | Degree | Distance of surface S408 (mm) | Refractive power | Degree | Distance of surface S408 (mm) |
| 1 D | 200 | −9.20 | 1 D | 200 | −8.49 |
| 2 D | 200 | −9.60 | 2 D | 200 | −8.90 |
| 3 D | 300 | −10.01 | 3 D | 300 | −9.32 |
| 4 D | 400 | −10.40 | 4 D | 400 | −9.72 |
| 5 D | 500 | −10.79 | 5 D | 500 | −10.12 |
| 6 D | 600 | −11.19 | 6 D | 600 | −10.52 |
| 7 D | 700 | −11.58 | 7 D | 700 | −10.92 |
| 8 D | 800 | −11.94 | 8 D | 800 | −11.29 |
| 9 D | 900 | −12.31 | 9 D | 900 | −11.67 |
| 10 D | 2000 | −12.67 | 10 D | 2000 | −12.04 |
| 15 D | 1500 | −14.49 | 15 D | 1500 | −13.90 |
| 20 D | 2000 | −16.10 | 20 D | 2000 | −15.55 |

In Table 4D and Table 4E, the meaning of each of the refractive power and the degree is as described in Table 1D and Table 1E and is not repeated herein. Moreover, the meaning of the distance of the surface S408 is as described in Table 4C and is not repeated herein.

Figure 15A:
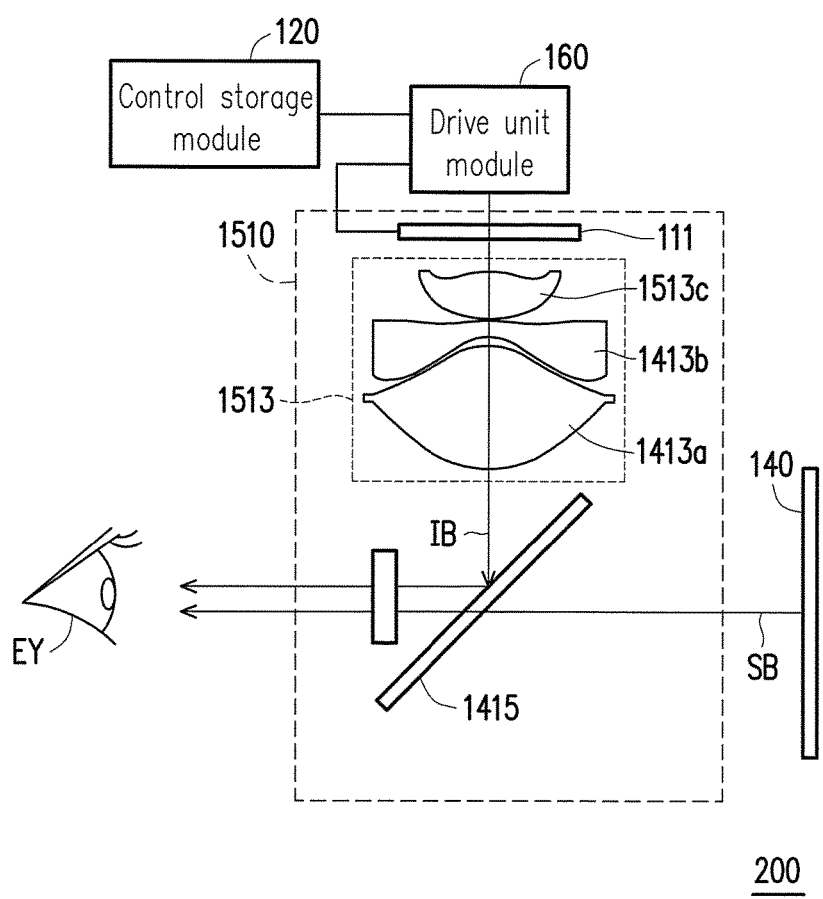
FIG. 15A is a schematic diagram of the architecture of a virtual image display system of still yet another embodiment of the disclosure.
Figure 15B:
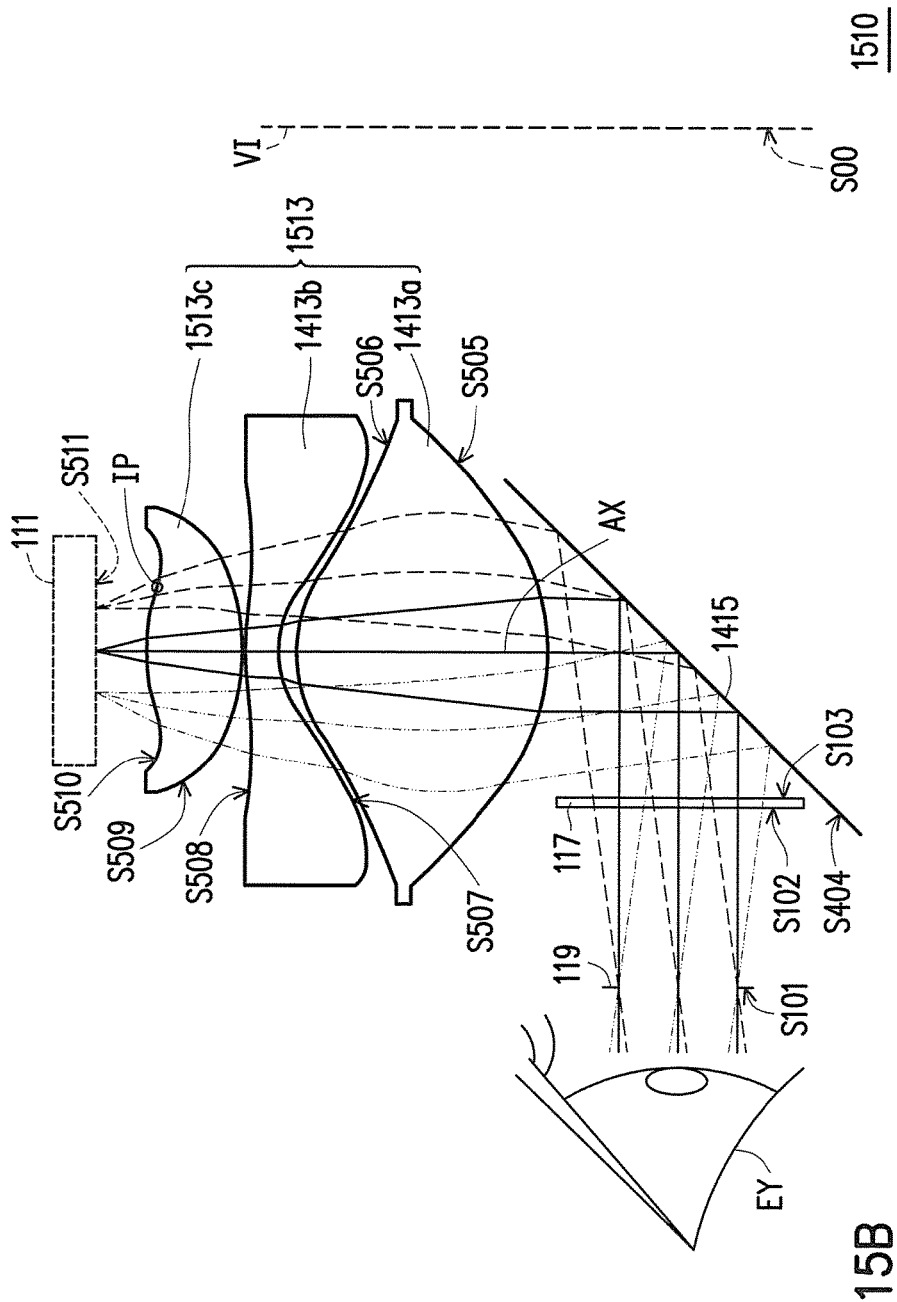
FIG. 15B is a schematic diagram of the architecture of a virtual image display module of FIG. 15A.

FIG. 15A is a schematic diagram of the architecture of a virtual image display system of still yet another embodiment of the disclosure. FIG. 15B is a schematic diagram of the architecture of a virtual image display module of FIG. 15A. Referring to FIG. 15A, the virtual image display system 200a of the present embodiment is similar to the virtual image display system 200 of FIG. 14A, and the difference between the two is as described below. Specifically, in the present embodiment, the motion compensation lens group 1513 of the virtual image display system 200a further includes a third lens 1513c, the refractive power of the third lens 1513c is positive, and the third lens 1513c is disposed between the image display unit 111 and the second lens 1413b. More specifically, the third lens 1513c is an aspheric lens and the third lens 1513c is a biconvex lens. Moreover, a cut curve obtained by cutting the convex surface of the third lens 1513c facing the image display unit 111 along an optical axis AX of the third lens 1513c can have at least one inflection point IP, and the inflection point IP is where the sign of the slope derivative of the obtained cut curve changes.

Moreover, the material of the third lens 1513c is, for instance, plastic. Moreover, in the present embodiment, the Abbe number of the third lens 1513c is greater than 40 to reduce the effect of color aberration caused by optical elements to the image beam IB. As a result, the image quality can be further enhanced. More specifically, as shown in FIG. 15B, in the present embodiment, the image display unit 111, the motion compensation lens group 1513, and the beam splitting unit 1415 can be designed together to determine the imaging properties of the virtual image VI. In particular, the detailed optical parametric design is as shown in Table 5A:

TABLE 5A

| Surface | Surface type | Radius of curvature | Distance | Material | Note |
|---|---|---|---|---|---|
| S00 | Sphere | Infinity | −3000.0000 | | Virtual image VI |
| S101 | Sphere | Infinity | 12.0000 | | Exit pupil 119 |
| S102 | Sphere | Infinity | 0.7000 | BK7 | Sheet glass 117 |
| S103 | Sphere | Infinity | 10.0000 | | |
| S404 | Sphere | Infinity | −9.0000 | | Beam splitting unit 1415 |
| S505 | Aspheric surface | −14.4419 | −16.9866 | 'Z-E48R' | First lens 1413a |
| S506 | Aspheric surface | 7.7927 | −1.2464 | | |
| S507 | Aspheric surface | 5.5831 | −2.2503 | 'OKP4HT' | Second lens 1413b |
| S508 | Aspheric surface | 26.5511 | −0.0989 | | |
| S509 | Aspheric surface | −12.6385 | −6.4998 | 'Z-E48R' | Third lens 1513c |
| S510 | Aspheric surface | 21.7691 | −4.1467 | | |
| S511 | Sphere | Infinity | 0.0000 | | Image display unit 111 |

In Table 5A, the unit of the radius of curvature is millimeter (mm) and the surfaces S505 and S506 respectively represent the two surfaces of the first lens 1413a of the motion compensation lens group 1513. The surfaces S507 and S508 represent the two surfaces of the second lens 1413b of the motion compensation lens group 1513. The surfaces S509 and S510 represent the two surfaces of the third lens 1513c of the motion compensation lens group 1513. The meaning of each of the surfaces S00, S101, S102, S103, and S404 and materials is as described in Table 1A and Table 4A and is not repeated herein.

Moreover, a number of important parameter values of the virtual image display module 1510 are exemplified below. In the present embodiment, the field of view of the virtual image display module 1510 is 36.5 degrees, the f-number is 2.17, the lateral color aberration is 9.5 µm, and the ratio of the diameter of the reflection unit 114 to the diameter of the exit pupil 119 is 4.02. Moreover, the asphericity of each of the aspheric surfaces (such as surfaces S505, S506, S507, S508, S509, and S510) is as shown in Table 5B below:

TABLE 5B

| | S505 | S506 | S507 | S508 | S509 | S510 |
|---|---|---|---|---|---|---|
| Radius of lens | −0.06924 | 0.128325 | 0.1791513 | 0.037663 | −0.07912 | 0.045937 |
| Conic constant (K) | $-6.53 \times 10^{-01}$ | $-9.10 \times 10^{-01}$ | $-1.23 \times 10^{+00}$ | $0.00 \times 10^{+00}$ | 0.267895 | 0 |
| 4th order parameter ($A_4$) | $-3.00 \times 10^{-06}$ | $-3.29 \times 10^{-04}$ | $-4.10 \times 10^{-04}$ | $-2.63 \times 10^{-04}$ | 0.000272 | 0.000688 |
| 6th order parameter ($A_6$) | $1.16 \times 10^{-08}$ | $9.06 \times 10^{-07}$ | $1.61 \times 10^{-06}$ | $1.43 \times 10^{-06}$ | $-4.16 \times 10^{-06}$ | $-2.36 \times 10^{-05}$ |
| 8th order parameter ($A_8$) | $2.04 \times 10^{-10}$ | $-1.23 \times 10^{-09}$ | $-2.71 \times 10^{-09}$ | $-4.09 \times 10^{-09}$ | $-3.44 \times 10^{-09}$ | $1.11 \times 10^{-07}$ |
| 10th order parameter ($A_{10}$) | $1.84 \times 10^{-14}$ | $-1.32 \times 10^{-14}$ | $4.02 \times 10^{-15}$ | $3.06 \times 10^{-13}$ | $2.61 \times 10^{-11}$ | $1.21 \times 10^{-10}$ |

In Table 5B, the formula of each of the aspheric surfaces (such as surfaces S505, S506, S507, S508, S509, and S510) is the same as the formula for Table 1B, and the physical meaning of each of the parameters is as described in Table 1B and is not repeated herein.

Moreover, in the present embodiment, the user UR can also adjust the relative position of the image display unit 111 and the motion compensation lens group 1513 of the virtual image display module 1510 through the control unit 123 according to personal habits to correspondingly change the imaging position and the size of the image frame of the virtual image VI to facilitate the use of the virtual image display system 200a or perform relevant visual compensation. In particular, the relationship between the relative position of the image display unit 111 and the motion compensation lens group 1513 and the imaging position and the size of the image frame of the virtual image VI is as described in Table 5C below:

TABLE 5C

| Surface | Distance (mm) | Size of image frame (inch) |
|---|---|---|
| S00 | −250 | 6.5" |
| S510 | −2.89 | |
| S00 | −500 | 13" |
| S510 | −3.61 | |
| S00 | −1000 | 26" |
| S510 | −3.94 | |
| S00 | −2000 | 52" |
| S510 | −4.1 | |
| S00 | −3000 | 78" |
| S510 | −4.15 | |
| S00 | −4000 | 104" |
| S510 | −4.17 | |
| S00 | −5000 | 130" |
| S510 | −4.19 | |
| S00 | −6000 | 156" |
| S510 | −4.2 | |

In Table 5C, the distance of the surface S510 represents the distance between the surface S510 of the third lens 1513c of the motion compensation lens group 1513 facing the image display unit 111 and the display surface (i.e., surface S511) of the image display unit 111 along the direction of the optical axis AX. Moreover, in the present embodiment, when the distance of the surface S510 is 4.2485 mm, the largest size of the image frame of the virtual image VI can be obtained. Moreover, the meaning of the distance and the other data of the surface S00 is as described in Table 4C and is not repeated herein.

Moreover, the relationship between the relative position of each of the image display unit 111 and the motion compensation lens group 1513 and the refractive power of the eye EY of the user UR is as described in Table 5D and Table 5E:

TABLE 5D

Myopia

| | Virtual image located 3 m in front of eye | | | Virtual image located 50 cm in front of eye | |
|---|---|---|---|---|---|
| Refractive power | Degree | Distance of surface S510 (mm) | Refractive power | Degree | Distance of surface S510 (mm) |
| −1 D | −200a | −3.84 | −1 D | −200a | −3.28 |
| −2 D | −200 | −3.52 | −2 D | −200 | −2.94 |
| −3 D | −300 | −3.19 | −3 D | −300 | −2.59 |

TABLE 5D-continued

Myopia

| | Virtual image located 3 m in front of eye | | | Virtual image located 50 cm in front of eye | |
|---|---|---|---|---|---|
| Refractive power | Degree | Distance of surface S510 (mm) | Refractive power | Degree | Distance of surface S510 (mm) |
| −4 D | −400 | −2.85 | −4 D | −400 | −2.23 |
| −5 D | −500 | −2.49 | −5 D | −500 | −1.86 |
| −6 D | −600 | −2.12 | −6 D | −600 | −1.47 |
| −7 D | −700 | −1.74 | −7 D | −700 | −1.06 |
| −8 D | −800 | −1.36 | −8 D | −800 | −0.66 |
| −9 D | −900 | −0.95 | −9 D | −900 | −0.23 |
| −10 D | −1000 | −0.54 | −10 D | −1000 | 0.21 |

TABLE 5E

Hyperopia

| | Virtual image located 3 m in front of eye | | | Virtual image located 50 cm in front of eye | |
|---|---|---|---|---|---|
| Refractive power | Degree | Distance of surface S510 (mm) | Refractive power | Degree | Distance of surface S510 (mm) |
| 1 D | 200a | −4.45 | 1 D | 200a | −3.93 |
| 2 D | 200 | −4.74 | 2 D | 200 | −4.23 |
| 3 D | 300 | −5.02 | 3 D | 300 | −4.53 |

In Table 5D and Table 5E, the meaning of each of the refractive power and the degree is as described in Table 1D and Table 1E and is not repeated herein. Moreover, the meaning of the distance of the surface S510 is as described in Table 5C and is not repeated herein.

Moreover, it should also be mentioned that, in the previous embodiments, the virtual image display modules 1210, 1310, 1410, and 1510 can all use the structure of the first compensation lens 116 to form a structural design similar to the virtual image display module 110a or 110b and can achieve a function similar to the virtual image display module 110a or 110b. In the embodiments, when the first compensation lens 116 is a lens, the relationship between the focal length of the first compensation lens 116 and the eyesight of the eye EY of the user UR is as shown in Table 1H and is not repeated herein. Moreover, when the first compensation lens 116 is a liquid lens, the detailed optical parametric design of the first compensation lens 116 is as shown in Table 1I, and the relationship between the eyesight of the eye EY of the user UR and the optical parameters of the first compensation lens 116 is as exemplified in Table 1J and is not repeated herein.

Moreover, in the previous embodiments, the virtual image display modules 1210, 1310, 1410, and 1510 can also be combined with components such as the ambient light adjustment unit 140, the frame 150, the drive unit module 160, the rotatable support base 170, the mechanism adjustment unit module 180, the casing 190, the image capture module ICM, the displacement sensing module DSM, and a voice capture module SCM to form an appearance similar to the virtual image display system 100 and have the function provided by the virtual image display system 100, and is not repeated herein. In the embodiments, the virtual image display modules 1210 and 1310 can be used with the ambient light adjustment unit 140 having a shutter, a photochromic lens, a polarizer, a filter, or a liquid crystal unit. Moreover, the virtual image display modules 1410 and 1510 can be used with the ambient light adjustment unit 140 having a shutter, a photochromic lens, a filter, or a liquid crystal unit.

Moreover, it should also be mentioned that, although the virtual image display system 100 is exemplified as having two virtual image display modules to form the appearance of a machine having binocular vision, the disclosure is not limited thereto. In other embodiments, the virtual image display module can also only have one virtual image display module to form the structural design of a machine having monocular vision. FIG. 16A to FIG. 16D are used for further explanation below.

Figure 16A:
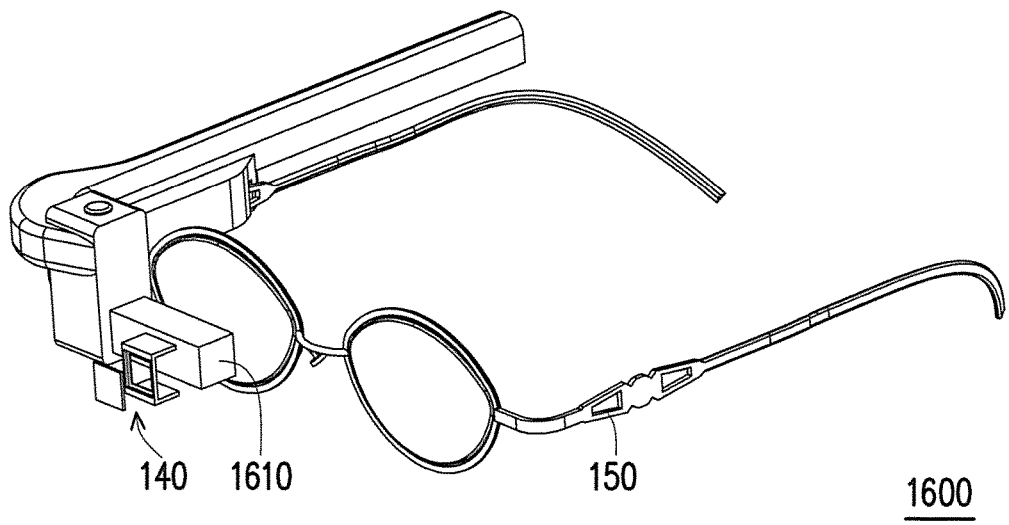
FIG. 16A is a schematic diagram of the exterior of a virtual image display system of another embodiment of the disclosure.
Figure 16B:
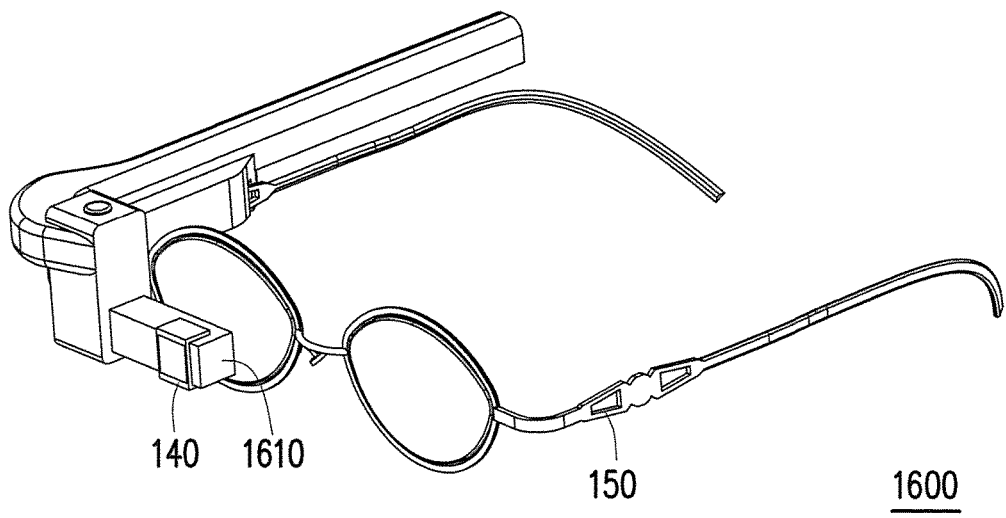
FIG. 16B is an exploded view of a portion of the virtual image display system of FIG. 16A.

FIG. 16A is a schematic diagram of the exterior of a virtual image display system of another embodiment of the disclosure. FIG. 16B is an exploded view of a portion of the virtual image display system of FIG. 16A. Referring to FIG. 16A and FIG. 16B, the virtual image display system 1600 of the present embodiment is similar to the virtual image display system 100 of FIG. 4, and the difference between the two is as described below. Specifically, retelling to FIG. 16A and FIG. 16B, the virtual image display system 1600 mainly includes a virtual image display module 1610 and the virtual image display module 1610 is disposed on one side of the frame 150. More specifically, as shown in FIG. 16A and FIG. 16B, in the present embodiment, the ambient light adjustment unit 140 is, for instance, a U-shaped structure, and can be assembled on the virtual image display module 1610. FIG. 16C to FIG. 19 are used to further explain the overall design of the optical structure of the virtual image display module 1610 below.

Figure 16C:
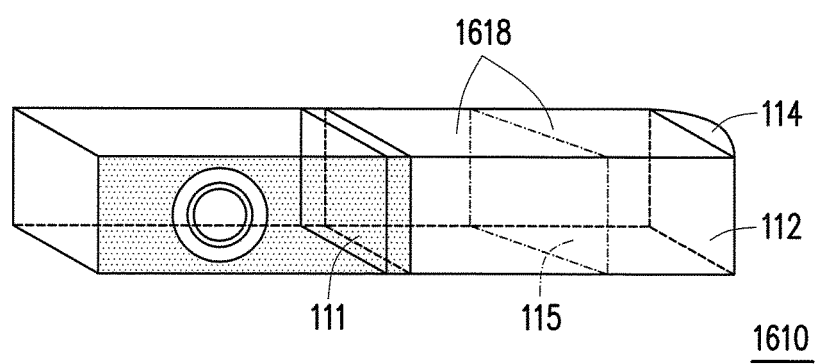
FIG. 16C is a schematic diagram of the architecture of a virtual image display module of FIG. 16A.
Figure 16D:
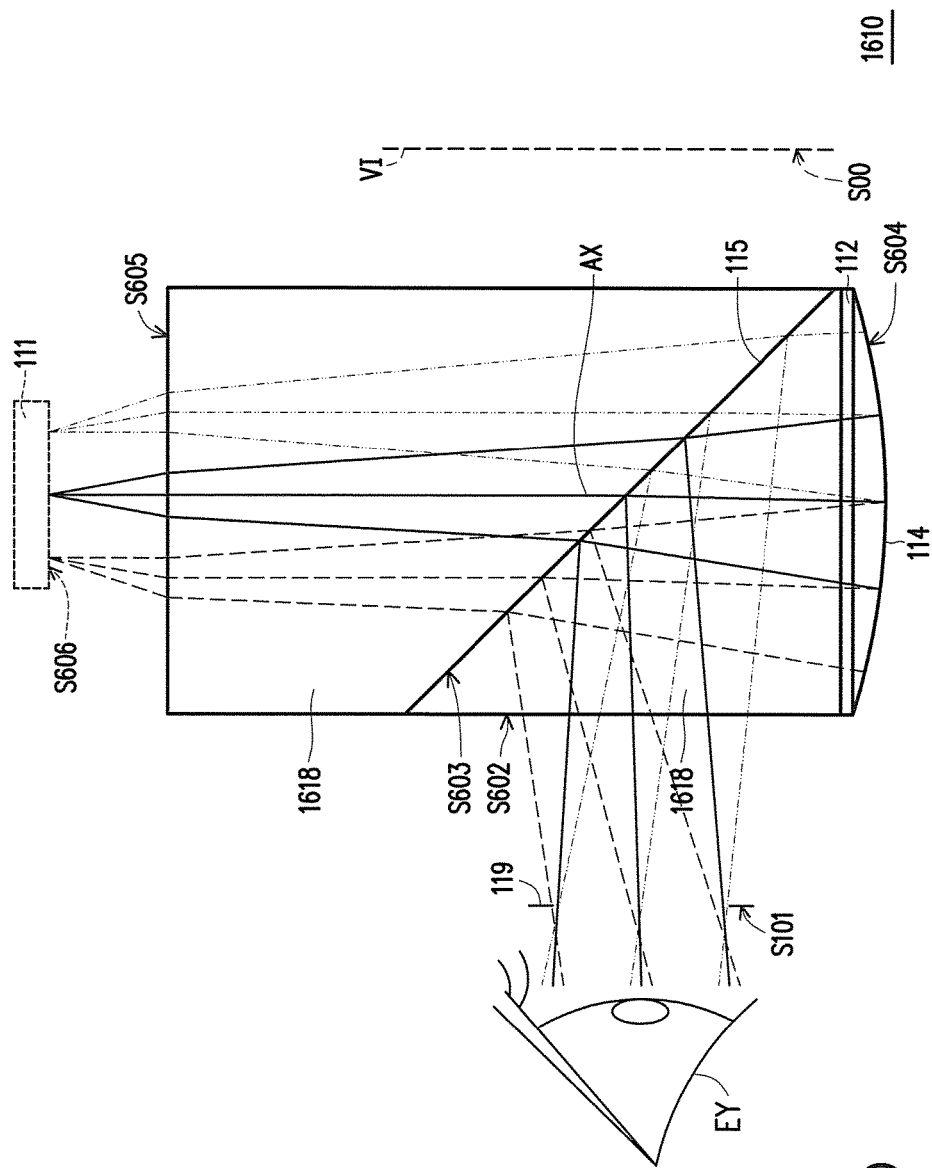
FIG. 16D is a schematic diagram of the architecture of the virtual image display module of FIG. 16C.

FIG. 16C is a stereoscopic schematic diagram of the architecture of a virtual image display module of FIG. 16A. FIG. 16D is a schematic diagram of the architecture of the virtual image display system of FIG. 16C. Referring to FIG. 16C and FIG. 16D, the virtual image display module 1610 of the present embodiment is similar to the virtual image display module 110 of FIG. 6A, and the difference between the two is as described below. Specifically, referring to FIG. 16C, the virtual image display module 1610 further includes a light guide rod 1618 located between the image display unit 111 and the beam splitting unit 115. Moreover, in the present embodiment, the light guide rod 1618 can further be optionally disposed between the reflection unit 114 and the beam splitting unit 115. In other words, in the present embodiment, the light guide rod 1618 is filled between the image display unit 111 and the beam splitting unit 115 and between the reflection unit 114 and the beam splitting unit 115.

Moreover, specifically, in the present embodiment, the Abbe number of the light guide rod 1618 is greater than 40 to reduce the effect of aberration caused by optical elements to the image beam IB. As a result, the image quality can be further enhanced. Moreover, in the present embodiment, the sheet glass 117 is not disposed in the virtual image display module 1610, but the disclosure is not limited thereto. In other embodiments, optical elements such as the sheet glass 117 can be optionally disposed in the virtual image display module 1610 according to actual need. Moreover, in other embodiments, the wave plate 112 can also be optionally disposed between the reflection unit 114 and the beam splitting unit 115 according to actual need. In particular, the detailed optical parametric design of the virtual image display module 1610 is as shown in Table 6A:

TABLE 6A

| Surface | Surface type | Radius of curvature | Distance | Material | Note |
|---|---|---|---|---|---|
| S00 | Sphere | Infinity | −3000 | | Virtual image VI |
| S101 | Sphere | Infinity | 15 | | Exit pupil 119 |
| S602 | Sphere | Infinity | 6 | SFSL5 | Light guide rod 1618 |
| S603 | Sphere | Infinity | −9.3 | SFSL5 | Beam splitting unit 115 |
| S604 | Aspheric surface | 41.69609 | 17.6 | SFSL5 | Reflecting unit 114 |
| S605 | Sphere | Infinity | 2.11197728 | | |
| S606 | Sphere | Infinity | 0.00 | | Image display unit 111 |

In Table 6A, the unit of the radius of curvature is millimeter (mm) and the surfaces S602 and S605 respectively represent the incident surface and the light exit surface of the light guide rod 1618 light enters and exits. The surface S603 represents the surface of the beam splitting unit 115 facing the exit pupil 119. The surface S604 represents the reflecting surface of the reflection unit 114. The surface S606 represents the display surface of the image display unit 111. The meaning of each of the surfaces and materials is as described in Table 1A and is not repeated herein.

Moreover, a number of important parameter values of the virtual image display module 1610 are exemplified below. In the present embodiment, the field of view of the virtual image display module 1610 is 20 degrees, the lateral color aberration is 10.5 μm, the diameter of the exit pupil 119 is 4 mm, the eye relief is 15 mm, and the value of the modulation transfer function (MTF) simulated under a spatial frequency of 45 lp/mm is greater than 0.59. Moreover, the asphericity of the aspheric surface (such as surface S604) is as shown in Table 6B below:

TABLE 6B

| | S604 |
|---|---|
| Radius of lens | 41.69609 |
| Conic constant (K) | 7.474396 |
| 4th order parameter ($A_4$) | $-1.13 \times 10^{-05}$ |
| 6th order parameter ($A_6$) | $-6.24 \times 10^{-08}$ |
| 8th order parameter ($A_8$) | 0 |
| 10th order parameter ($A_{10}$) | 0 |

In Table 6B, the formula of the aspheric surface (such as surface S604) is the same as the formula for Table 1B, and the physical meaning of each of the parameters is as described in Table 1B and is not repeated herein.

Moreover, in the present embodiment, the user UR can also adjust the relative position of each of the image display unit 111 and the light guide rod 1618 of the virtual image display module 161 through the control unit 123 according to personal habits to correspondingly change the imaging position and the size of the image frame of the virtual image VI to facilitate the use of the virtual image display system 1600 or perform relevant visual compensation. In particular, the relationship between the relative position of each of the image display unit 111 and the light guide rod 1618 and the imaging position of the virtual image VI is as described in Table 6C below:

TABLE 6C

| Surface | Distance (mm) |
|---|---|
| S00 | −250 |
| S605 | 1.3768 |
| S00 | −500 |
| S605 | 1.7858 |
| S00 | −1000 |
| S605 | 1.9831 |
| S00 | −2000 |
| S605 | 2.0799 |
| S00 | −3000 |
| S605 | 2.112 |
| S00 | −4000 |
| S605 | 2.1279 |
| S00 | −5000 |
| S605 | 2.1375 |
| S00 | −6000 |
| S605 | 2.1439 |

In Table 6C, the distance of the surface S605 represents the distance between the surface S605 of the light guide rod 1618 facing the image display unit 111 and the display surface (i.e., surface S606) of the image display unit 111 along the direction of the optical axis AX. Moreover, in the present embodiment, when the distance of the surface S605 is 2.1757 mm, the largest size of the image frame of the virtual image VI can be obtained. Moreover, the meaning of the distance and the other data of the surface S00 is as described in Table 1C and is not repeated herein.

Moreover, although the material of the light guide rod 1618 above is exemplified as a material having the material number SFSL5, the disclosure is not limited thereto. In another embodiment, the material of the light guide rod 1618 can also be poly(methyl methacrylate) (PMMA). In the present embodiment, the detailed optical parametric design of the virtual image display module 1610 is as shown in Table 6D:

In Table 6D, the unit of the radius of curvature is millimeter (mm) and the meaning of each of the surfaces is as described in Table 6A and is not repeated herein.

Moreover, in the present embodiment, the field of view of the virtual image display module 1610 is 20 degrees, the lateral color aberration is 13 μm, the diameter of the exit pupil 119 is 4 mm, the eye relief is 15 mm, and the value of the modulation transfer function (MTF) simulated under a spatial frequency of 45 lp/mm is greater than 0.53. Moreover, the asphericity of the aspheric surface (such as surface S604) is as shown in Table 6E below:

TABLE 6E

| | S604 |
|---|---|
| Radius of lens | 43.32001 |
| Conic constant (K) | 3.16934 |
| 4th order parameter ($A_4$) | $-3.69 \times 10^{-06}$ |
| 6th order parameter ($A_6$) | $-2.30 \times 10^{-08}$ |
| 8th order parameter ($A_8$) | 0 |
| 10th order parameter ($A_{10}$) | 0 |

In Table 6E, the formula of the aspheric surface (such as surface S604) is the same as the formula for Table 1B, and the physical meaning of each of the parameters is as described in Table 1B and is not repeated herein.

Moreover, although the virtual image display module 1610 above is exemplified as having the same material for the light guide rod 1618 and the reflection unit 114, the disclosure is not limited thereto. In other embodiments, the materials of the light guide rod 1618 and the reflection unit 114 can also be different. In the following, FIG. 17 is used for further explanation.

Figure 17:
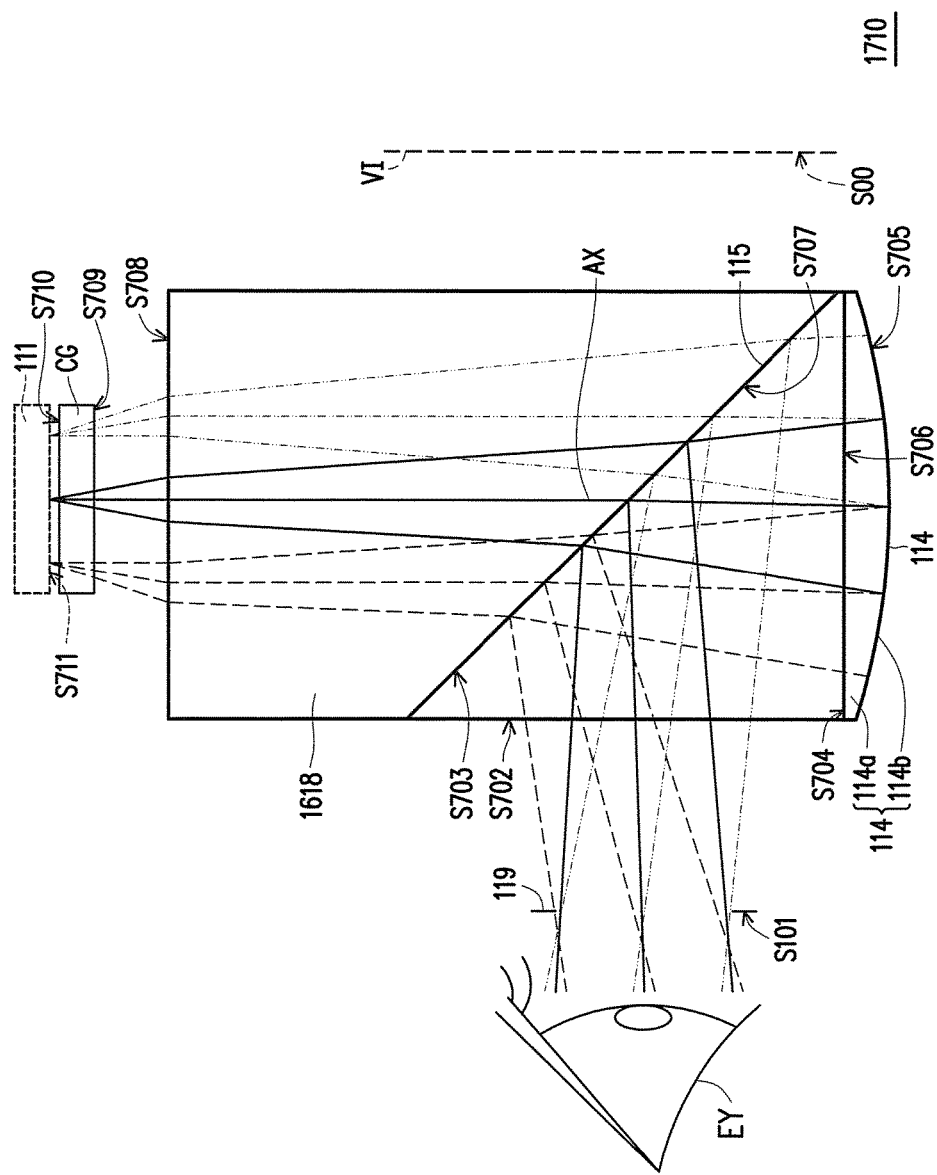
FIG. 17 is a schematic diagram of the architecture of another virtual image display module of FIG. 16A.

FIG. 17 is a schematic diagram of the architecture of another virtual image display system of FIG. 16A. Referring to FIG. 17, the virtual image display module 1710 of the present embodiment is similar to the virtual image display module 1610 of FIG. 16D, and the difference between the two is as described below. Specifically, the materials of the light guide rod 1618 and the reflection unit 114 of the virtual image display module 1710 are different. Moreover, in the present embodiment, the reflection unit 114 includes a lens 114a and a reflection coating 114b. In particular, the detailed optical parametric design of the virtual image display module 1610 is as shown in Table 7A:

TABLE 6D

| Surface | Surface type | Radius of curvature | Distance | Material | Note |
|---|---|---|---|---|---|
| S00 | Sphere | Infinity | −2500 | | Virtual image VI |
| S101 | Sphere | Infinity | 15 | | Exit pupil 119 |
| S602 | Sphere | Infinity | 6 | 'PMMAO' | Light guide rod 1618 |
| S603 | Sphere | Infinity | −9.3 | 'PMMAO' | Beam splitting unit 115 |
| S604 | Aspheric surface | 43.32001 | 17.6 | 'PMMAO' | Reflecting unit 114 |
| S605 | Sphere | Infinity | 2.632875 | | |
| S606 | Sphere | Infinity | 0 | | Image display unit 111 |

TABLE 7A

| Surface | Surface type | Radius of curvature | Distance | Material | Note |
|---|---|---|---|---|---|
| S00 | Sphere | Infinity | −2500 | | Virtual image VI |
| S101 | Sphere | Infinity | 15 | | Exit pupil 119 |
| S702 | Sphere | Infinity | 5.9 | BK7 | Light guide rod 1618 |
| S703 | Sphere | Infinity | −7 | BK7 | Beam splitting unit 115 |
| S704 | Sphere | Infinity | 1.5 | 'PMMAO' | Lens 114a |
| S705 | Aspheric surface | 40.909 | −1.5 | 'PMMAO' | Reflection coating 114b |
| S706 | Sphere | Infinity | 7 | BK7 | Light guide rod 1618 |
| S707 | Sphere | Infinity | 9.5 | BK7 | Beam splitting unit 115 |
| S708 | Sphere | Infinity | 1.51367433 | | |
| S709 | Sphere | Infinity | 1.4 | BK7 | Cover glass CG |
| S710 | Sphere | Infinity | 0.115 | | |
| S711 | Sphere | Infinity | 0 | | Image display unit 111 |

In Table 7A, the unit of the radius of curvature is millimeter (mm) and the surface S702 represents the incident surface of the light guide rod 1618 light enters. The surface S703 represents the surface of the beam splitting unit 115 facing the exit pupil 119. The surface S704 represents the surface of the lens 114a of the reflection unit 114 facing the beam splitting unit 115. The surface S705 represents the reflective surface of the reflection coating 114b of the reflection unit 114. The surface S706 represents the surface of the light guide rod 1618 light enters again. The surface S707 represents the surface of the beam splitting unit 115 facing the reflection unit 114. The surface S708 represents the surface of the light guide rod 1618 light exits. The surface S709 and the surface S710 respectively represent the two surfaces of the cover glass CG. The surface S711 represents the display surface of the image display unit 111. The meaning of each of the surfaces and materials is as described in Table 1A and Table 6D and is not repeated herein.

Moreover, in the present embodiment, the field of view of the virtual image display module 1710 is 20 degrees, the lateral color aberration is 13 μm, the diameter of the exit pupil 119 is 4 mm, the eye relief is 15 mm, and the value of the modulation transfer function (MTF) simulated under a spatial frequency of 45 lp/mm is greater than 0.53. Moreover, the asphericity of the aspheric surface (such as surface S705) is as shown in Table 7B below:

TABLE 7B

| | S705 |
|---|---|
| Radius of lens | 43.32001 |
| Conic constant (K) | 0 |
| 4th order parameter ($A_4$) | $1.18 \times 10^{-06}$ |
| 6th order parameter ($A_6$) | $-1.32 \times 10^{-08}$ |
| 8th order parameter ($A_8$) | 0 |
| 10th order parameter ($A_{10}$) | 0 |

In Table 7B, the formula of the aspheric surface (such as surface S705) is the same as the formula for Table 1B, and the physical meaning of each of the parameters is as described in Table 1B and is not repeated herein.

Moreover, in another embodiment, the material of the light guide rod 1618 of the virtual image display module 1710 can also be poly(methyl methacrylate) (PMMA) and the material of the lens 114a of the reflection unit 114 can also be an APEL plastic material having the material number 'A5514_25'. In the present embodiment, the detailed optical parametric design of the virtual image display module 1710 is as shown in Table 7C:

TABLE 7C

| Surface | Surface type | Radius of curvature | Distance | Material | Note |
|---|---|---|---|---|---|
| S00 | Sphere | Infinity | −2500 | | Virtual image VI |
| S101 | Sphere | Infinity | 15 | | Exit pupil 119 |
| S702 | Sphere | Infinity | 5.9 | 'PMMAO' | Light guide rod 1618 |
| S703 | Sphere | Infinity | −7 | PMMAO' | Beam splitting unit 115 |
| S704 | Sphere | Infinity | 1.5 | A5514_25' | Lens 114a |
| S705 | Aspheric surface | 44.846 | −1.5 | 'A5514_25' | Reflection coating 114b |
| S706 | Sphere | Infinity | 7 | 'PMMAO' | Light guide rod 1618 |
| S707 | Sphere | Infinity | 9.5 | 'PMMAO' | Beam splitting unit 115 |
| S708 | Sphere | Infinity | 1.363708 | | |
| S709 | Sphere | Infinity | 1.4 | BK7 | Cover glass CG |
| S710 | Sphere | Infinity | 0.115 | | |
| S711 | Sphere | Infinity | Infinity | | Image display unit 111 |

In Table 7C, the unit of the radius of curvature is millimeter (mm) and the meaning of each of the surfaces is as described in Table 7A, and is not repeated herein.

Moreover, in the present embodiment, the field of view of the virtual image display module 1710 is 20 degrees, the lateral color aberration is 14 μm, the diameter of the exit pupil 119 is 4 mm, the eye relief is 15 mm, and the value of the modulation transfer function (MTF) simulated under a spatial frequency of 45 lp/mm is greater than 0.5. Moreover, the asphericity of the aspheric surface (such as surface S705) is as shown in Table 7D below:

TABLE 7D

|  | S705 |
| --- | --- |
| Radius of lens | 44.84618 |
| Conic constant (K) | 0 |
| 4th order parameter ($A_4$) | $1.06 \times 10^{-06}$ |
| 6th order parameter ($A_6$) | $-1.36 \times 10^{-08}$ |
| 8th order parameter ($A_8$) | 0 |
| 10th order parameter ($A_{10}$) | 0 |

In Table 7D, the formula of the aspheric surface (such as surface S705) is the same as the formula for Table 1B, and the physical meaning of each of the parameters is as described in Table 1B and is not repeated herein.

Figure 18:
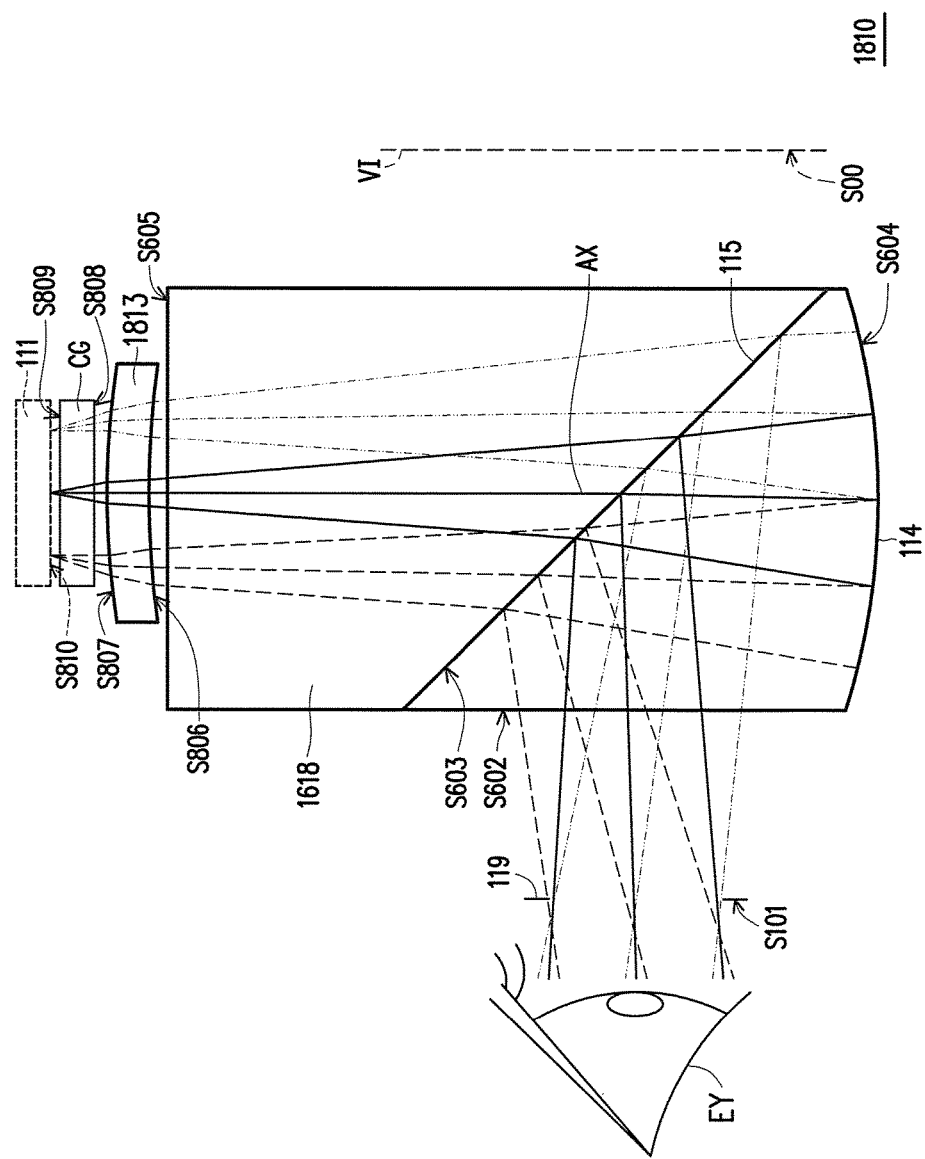
FIG. 18 is a schematic diagram of the architecture of yet another virtual image display module of FIG. 16A.

Moreover, in another embodiment, the virtual image display module 1710 can further include a fourth lens. FIG. 18 is used for further explanation below.

FIG. 18 is a schematic diagram of the architecture of yet another virtual image display system of FIG. 16A. Referring to FIG. 18, the virtual image display module 1810 of the present embodiment is similar to the virtual image display module 1610 of FIG. 16D, and the difference between the two is as described below. Specifically, as shown in FIG. 18, the virtual image display module 1810 further includes a fourth lens 1813 and is located between the light guide rod 1618 and the image display unit 111. Moreover, in the present embodiment, the Abbe number of the fourth lens 1813 is less than 40 to reduce the effect of aberration caused by optical elements to the image beam IB. As a result, the image quality can be further enhanced. In particular, the detailed optical parametric design of the virtual image display module 1810 is as shown in Table 8A:

In Table 8A, the unit of the radius of curvature is millimeter (mm) and the surface S806 and the surface S807 respectively represent the two surfaces of the fourth lens 1813. The surface S808 and the surface S809 respectively represent the two surfaces of the cover glass CG. The surface S810 represents the display surface of the image display unit 111. The meaning of each of the surfaces and materials is as described in Table 1A and Table 6D and is not repeated herein.

Moreover, in the present embodiment, the field of view of the virtual image display module 1810 is 20 degrees, the lateral color aberration is 6.3 μm, the diameter of the exit pupil 119 is 4 mm, the eye relief is 15 mm, and the value of the modulation transfer function (MTF) simulated under a spatial frequency of 45 lp/mm is greater than 0.45. Moreover, the asphericity of the aspheric surface (such as surface S604) is as shown in Table 8B below:

TABLE 8B

|  | S604 |
| --- | --- |
| Radius of lens | 40.40638 |
| Conic constant (K) | 0 |
| 4th order parameter ($A_4$) | $3.61 \times 10^{-06}$ |
| 6th order parameter ($A_6$) | $-2.22 \times 10^{-08}$ |
| 8th order parameter ($A_8$) | 0 |
| 10th order parameter ($A_{10}$) | 0 |

In Table 8B, the formula of the aspheric surface (such as surface S604) is the same as the formula for Table 1B, and the physical meaning of each of the parameters is as described in Table 1B and is not repeated herein.

Moreover, in another embodiment, the material of the fourth lens 1813 of the virtual image display module 1810 can be a polyester having the material number 'OKP4HT' in addition to an optical glass having the material number STIH53. Moreover, the two surfaces of the fourth lens 1813 can both be designed to be aspheric surfaces. In the present embodiment, the detailed optical parametric design of the virtual image display module 1810 is as shown in Table 8C:

TABLE 8A

| Surface | Surface type | Radius of curvature | Distance | Material | Note |
| --- | --- | --- | --- | --- | --- |
| S00 | Sphere | Infinity | −2500 |  | Virtual image VI |
| S101 | Sphere | Infinity | 15 |  | Exit pupil 119 |
| S602 | Sphere | Infinity | 6 | 'PMMAO' | Light guide rod 1618 |
| S603 | Sphere | Infinity | −8.5 | 'PMMAO' | Beam splitting unit 115 |
| S604 | Aspheric surface | 40.406 | 17 | 'PMMAO' | Reflecting unit 114 |
| S605 | Sphere | Infinity | 0.4 |  |  |
| S806 | Sphere | −14.000 | 1 | STIH53 | Fourth lens 1813 |
| S807 | Sphere | −27.489 | 0.23893282 |  |  |
| S808 | Sphere | Infinity | 1.4 | BK7 | Cover glass CG |
| S809 | Sphere | Infinity | 0.115 |  |  |
| S810 | Sphere | Infinity | 0 |  | Image display unit 111 |

TABLE 8C

| Surface | Surface type | Radius of curvature | Distance | Material | Note |
|---|---|---|---|---|---|
| S00 | Sphere | Infinity | −2500 | | Virtual image VI |
| S101 | Sphere | Infinity | 15 | | Exit pupil 119 |
| S602 | Sphere | Infinity | 5.8 | 'PMMAO' | Light guide rod 1618 |
| S603 | Sphere | Infinity | −8.5 | 'PMMAO' | Beam splitting unit 115 |
| S604 | Aspheric surface | 40.909 | 17 | 'PMMAO' | Reflecting unit 114 |
| S605 | Sphere | Infinity | 0.4 | | |
| S806 | Aspheric surface | −10.000 | 1 | 'OKP4HT' | Fourth lens 1813 |
| S807 | Aspheric surface | −13.215 | 0.350033 | | |
| S808 | Sphere | Infinity | 1.4 | BK7 | Cover glass CG |
| S809 | Sphere | Infinity | 0.115 | | |
| S810 | Sphere | Infinity | 0 | | Image display unit 111 |

In Table 8C, the unit of the radius of curvature is millimeter (mm) and the meaning of each of the surfaces is as described in Table 8A and is not repeated herein.

Moreover, in the present embodiment, the field of view of the virtual image display module 1810 is 20 degrees, the lateral color aberration is 6.6 μm, the diameter of the exit pupil 119 is 4 mm, the eye relief is 15 mm, and the value of the modulation transfer function (MTF) simulated under a spatial frequency of 45 lp/mm is greater than 0.47. Moreover, the asphericity of the aspheric surface (such as surface S604) is as shown in Table 8D below:

TABLE 8D

| | S604 | S806 | S807 |
|---|---|---|---|
| Radius of lens | 40.40638 | −10 | −13.2154 |
| Conic constant (K) | 0 | 0 | 0 |
| 4th order parameter ($A_4$) | $3.61 \times 10^{-06}$ | 0.004792 | 0.007723 |
| 6th order parameter ($A_6$) | $-2.22 \times 10^{-08}$ | −0.00031 | −0.00057 |
| 8th order parameter ($A_8$) | 0 | 0 | 0 |
| 10th order parameter ($A_{10}$) | 0 | 0 | 0 |

In Table 8D, the formula of the aspheric surface (such as surface S604) is the same as the formula for Table 1B, and the physical meaning of each of the parameters is as described in Table 1B and is not repeated herein.

Figure 19:
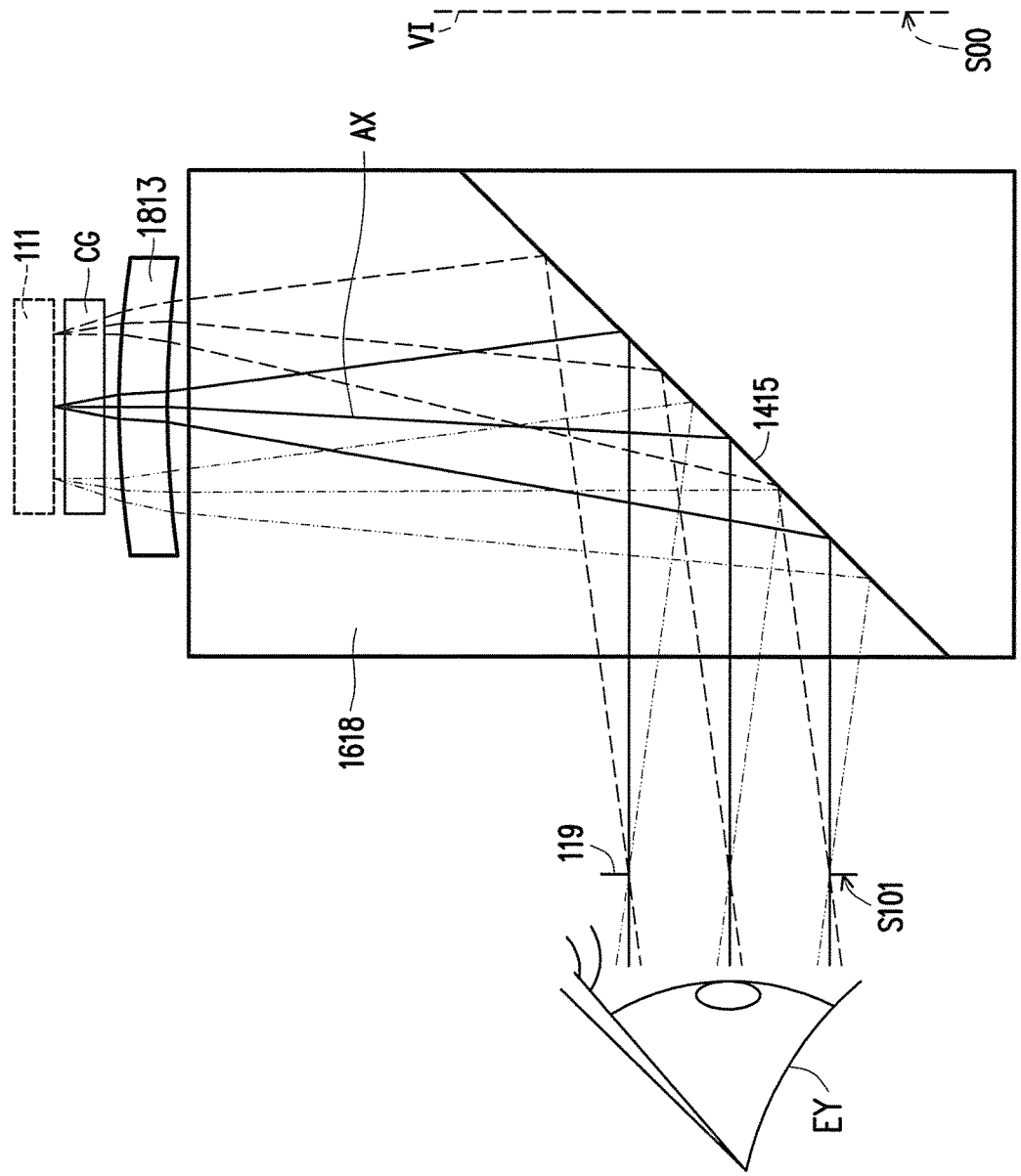
FIG. 19 is a schematic diagram of the architecture of still yet another virtual image display model of FIG. 16A.

Moreover, it should also be mentioned that, although the virtual image display modules 1610, 1710, and 1810 of the previous embodiments are all exemplified as including the reflection unit 114, the disclosure is not limited thereto. In other embodiments, the virtual image display module can also achieve the effect of providing partial light penetration and partial reflection to the incident light. FIG. 19 is used for further explanation below.

FIG. 19 is a schematic diagram of the architecture of still yet another virtual image display system of FIG. 16A. Referring to FIG. 19, the virtual image display module 1910 of the present embodiment is similar to the virtual image display module 1410 of FIG. 14B and the virtual image display module 1810 of FIG. 18, and the difference is described below. Specifically, the virtual image display module 1910 includes the fourth lens 1813 and is located between the light guide rod 1618 and the image display unit 111, and the virtual image display module 1410 includes the motion compensation lens group 1413 containing at least two aspheric lenses. Specifically, in the present embodiment, since the beam splitting unit 1415 of the virtual image display module 1910 is a partially-transmissive partially-reflective beam splitting element, the effect of partial light penetration and partial reflection can be provided to the incident light. For instance, in the present embodiment, the beam splitting unit 1415 can be an optical coated element having 30-70% transmittance and 30-70% reflectance. It should be mentioned that, the parameter range of the ratio of the transmittance to the reflectance is only used as an aid to explain the present embodiment, and the endpoints value and the size of the range thereof are not used to limit the disclosure.

Therefore, the beam splitting unit 1415 of the virtual image display module 1910 can cause at least a part of the object beam SB to pass through the beam splitting unit 1415 and be transmitted to the eye EY. Moreover, at least a part of the image beam IB emitted by the image display unit 111 can also be reflected by the beam splitting unit 1415 and be transmitted to the eye EY. In other words, the beam splitting unit 1415 of the virtual image display module 1910 can also achieve a similar function to the virtual image display modules 1610, 1710, and 1810 above and can allow the user UR to observe the physical image in front of the virtual image display modules 1610, 1710, and 1810 and the virtual image VI to be displayed by the image beam IB provided by the image display unit 111 at the same time, and also can be applied in the virtual image display system 1600 of FIG. 16A.

Moreover, in the present embodiment, although the virtual image display module 1910 is exemplified as having one fourth lens 1813, the disclosure is not limited thereto. In other embodiments, the virtual image display module 1910 can also have a structural design containing more than one lens. For instance, in the embodiment of each of the virtual image display modules 1410 and 1510 above, two solid prisms can be glued together and the interface thereof can be made to have 30-70% light transmittance and 30-70% light reflectance. In other words, the interface thereof can achieve a similar function to the beam splitting unit 1415, and one of the prisms can also achieve a similar function to the light guide rod 1618 such that the overall optical structure can achieve a similar function to the virtual image display module 1910. Other relevant implementation details are described in relevant paragraphs and are not repeated herein.

Moreover, in the previous embodiments, the virtual image display modules 1610, 1710, 1810, and 1910 can all use the structure of the first compensation lens 116 to form a structural design similar to the virtual image display module 110a or 110b and can achieve a function similar to the virtual image display module 110a or 110b. For instance, as shown in FIG. 16A, the first compensation lens 116 can be a lens located on the frame 150, but the disclosure is not limited thereto.

Figure 20A:
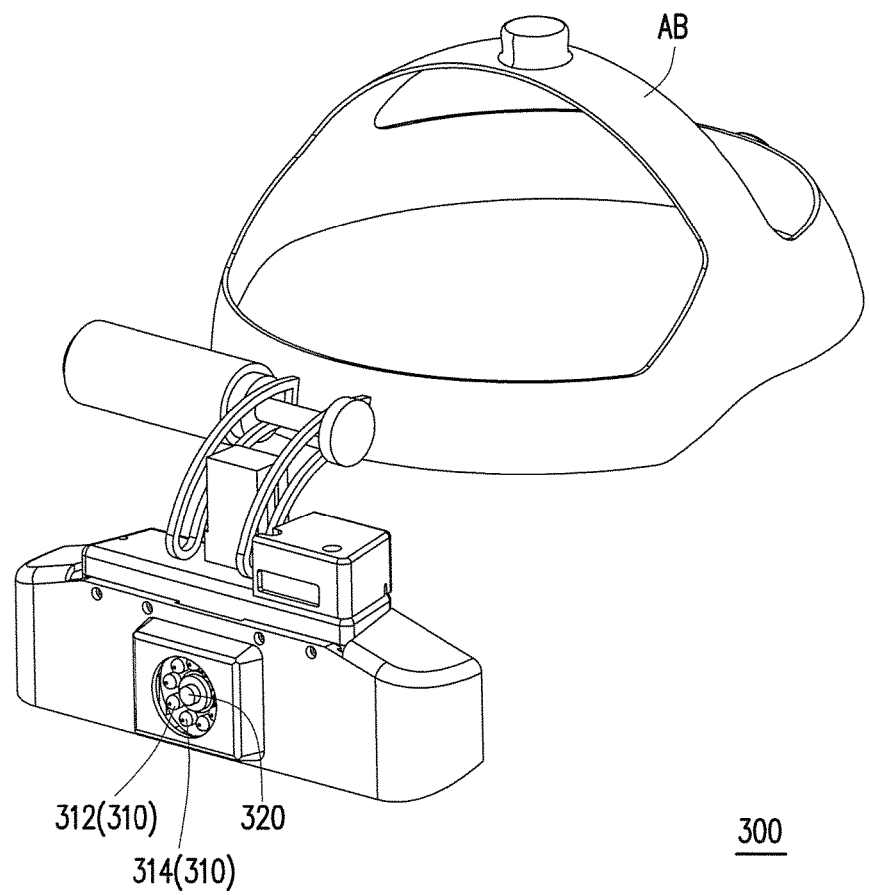
FIG. 20A is a schematic perspective view of a virtual image display system according to another embodiment of the disclosure.
Figure 20B:
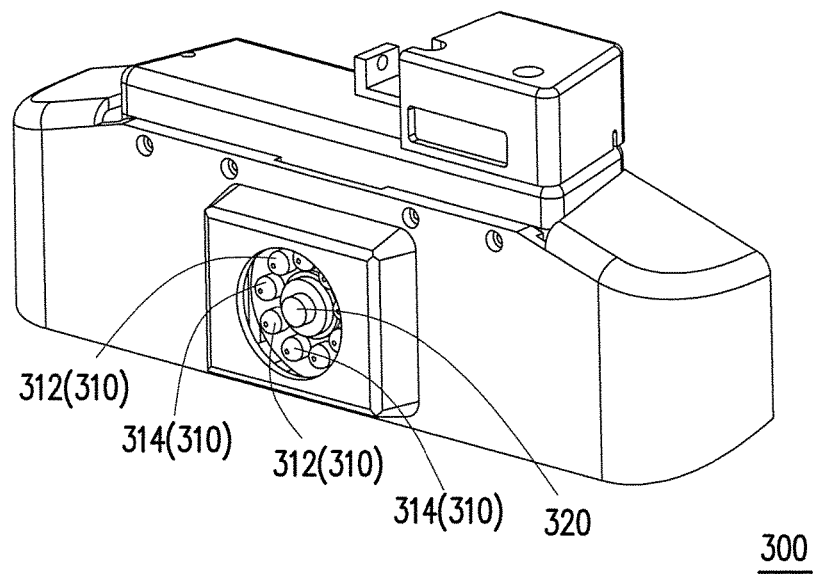
FIG. 20B is a schematic perspective view of the virtual image display system in FIG. 20A without showing the headband in FIG. 20A.
Figure 20C:
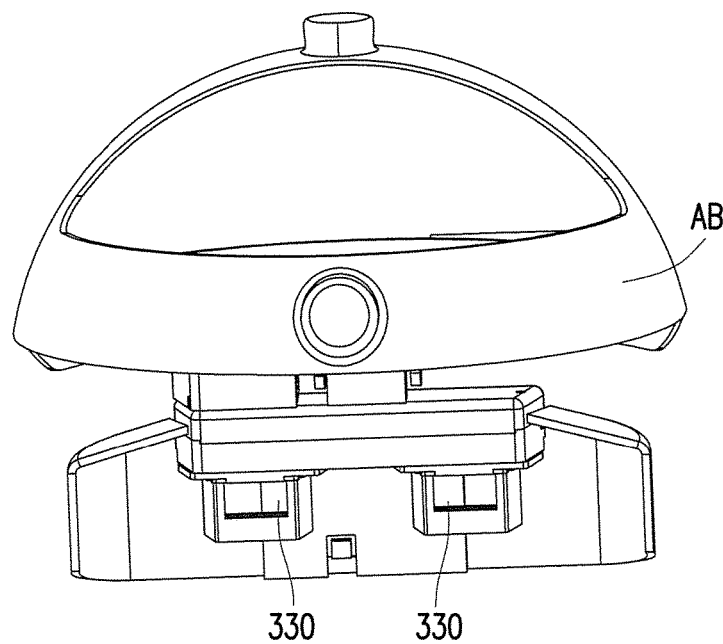
FIG. 20C is a schematic rear view of the virtual image display system in FIG. 20A.

FIG. 20A is a schematic perspective view of a virtual image display system according to another embodiment of the disclosure, FIG. 20B is a schematic perspective view of the virtual image display system in FIG. 20A without showing the headband in FIG. 20A, and FIG. 20C is a schematic rear view of the virtual image display system in FIG. 20A. Referring to FIGS. 20A to 20C, the virtual image display system 300 in this embodiment is adapted for venipuncture applications. The virtual image display system 300 comprises at least one infrared light source 310 (a plurality of infrared light sources 310 are exemplarily shown), at least one image sensing module 320 (one image sensing module 320 is exemplarily shown), and at least one virtual image display module 330 (two virtual image display modules 330 are exemplarily shown in FIG. 20C). The infrared light sources 310 are configured to emit infrared lights to a tissue having a vein (e.g. a tissue having venae of a person). The image sensing module 320 is configured to receive the infrared lights from the tissue so as to sense an image of the vein. The at least one virtual image display module 330 is disposed in front of at least one eye of a user. In this embodiment, two virtual image display module 330 are disposed in front of two eyes of the user. Each of the virtual image display modules 330 comprises an image display unit 111 (as shown in FIG. 4) electrically connected to the image sensing module 320 and configured to show an image of the vein (e.g. the virtual image of the vein) to the eye of the user. As a result, the user (e.g. a nurse or a doctor) may be easy to find the vein of a person (e.g. a patient) and perform venipuncture. Therefore, the possibility of success of performing venipuncture is effectively improved.

In this embodiment, the at least one infrared light source 310 is a plurality of infrared light sources 310 (e.g. the infrared light sources 312 and 314) configured to emit infrared lights having at least two wavelengths. For example, the infrared light source 312 may emit an infrared light with a wavelength of 850 nm, and the infrared light source 314 may emit an infrared light with a wavelength of 940 nm. The two infrared light with different wavelengths may penetrate the tissue to different depths, so that the user may see the veins at different depths through the virtual image display system 300.

In this embodiment, the infrared light source 310 may be a light-emitting diode (LED) or a laser diode, and the image sensing module 320 may be camera including a charge coupled device (CCD) or a complementary metal oxide semiconductor (CMOS) image sensor.

In this embodiment, the infrared light sources 310 surround the image sensing module 320. Moreover, in this embodiment, the image sensing module 320 comprises a fixed focus lens or a zoom lens. When the image sensing module 320 comprises a zoom lens, the zoom lens may zoom in the veins and magnify the veins. In this embodiment, the virtual image display system 300 in this embodiment further comprises a headband AB connected to the virtual image display module 330, the infrared light sources 310, and the image sensing module 320, so that the user may put the virtual image display module 330 on his or her head.

Figure 21A:
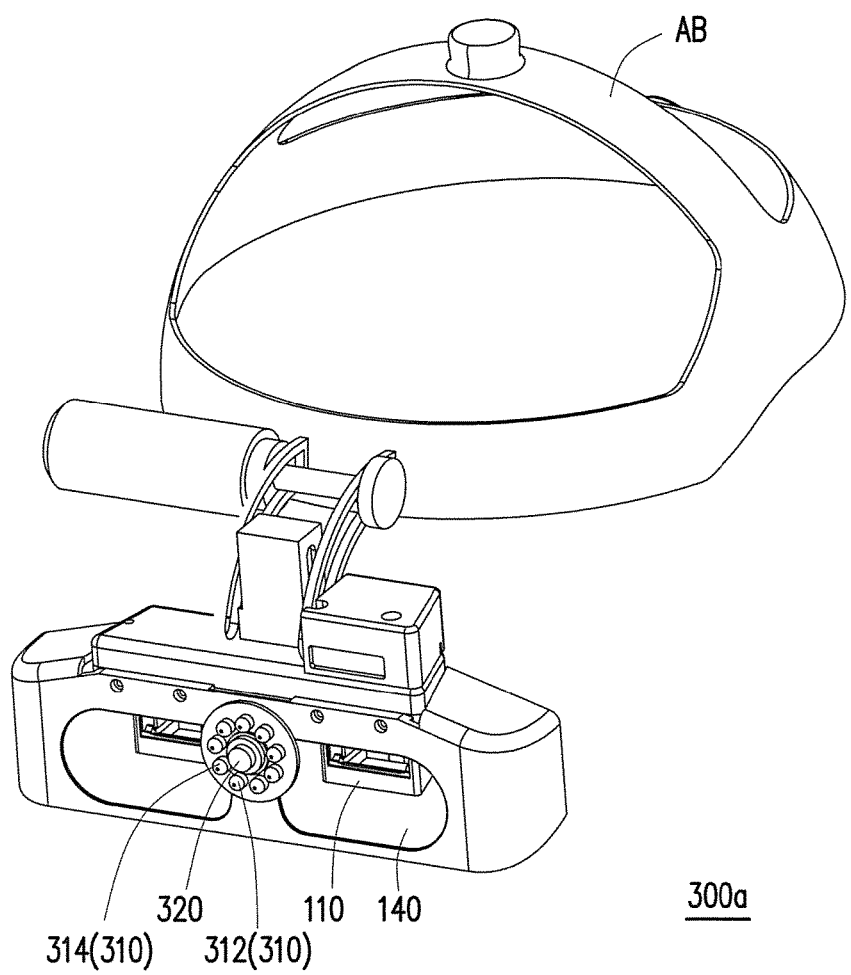
FIG. 21A is a schematic perspective view of a virtual image display system according to another embodiment of the disclosure.
Figure 21B:
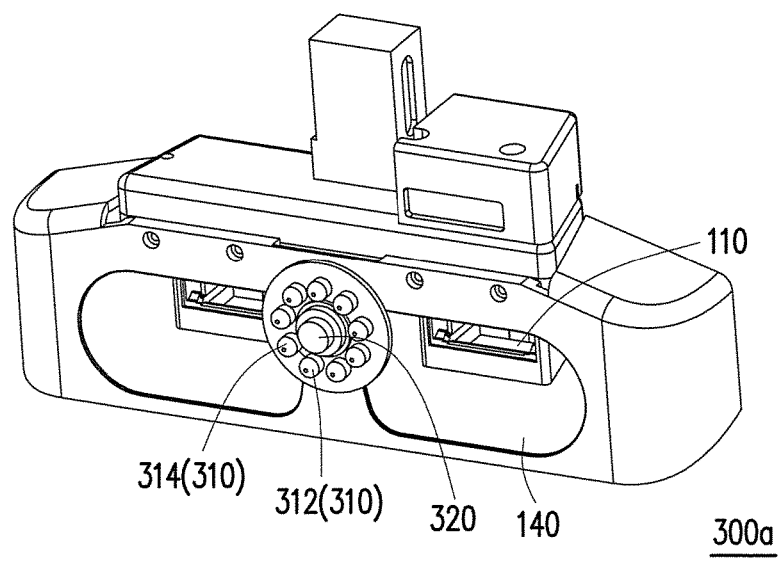
FIG. 21B is a schematic perspective view of the virtual image display system in FIG. 21A without showing the headband in FIG. 21A.

FIG. 21A is a schematic perspective view of a virtual image display system according to another embodiment of the disclosure, FIG. 21B is a schematic perspective view of the virtual image display system in FIG. 21A without showing the headband in FIG. 21A. Referring to FIG. 21A and FIG. 21B, the structures in FIG. 21A other than the infrared light sources 310 and the image sensing module 320 are similar to the structures shown in FIGS. 8C and 8D. Alternatively, the structures in FIG. 21A other than the infrared light sources 310 and the image sensing module 320 may be the virtual image display system shown in the embodiments of FIGS. 1 to 19, and may comprises the virtual image display module comprising the beam splitting unit 115. For example, as shown in FIG. 4, the image display unit 111 is configured to provide an image beam IB, and the at least one virtual image display module 110 further comprises a beam splitting unit 115 disposed on transmission paths of the image beam IB and an object beam SB from an environment object. The beam splitting unit 115 causes at least a part of the object beam SB to be transmitted to the eye EY, and the beam splitting unit 115 causes at least a part of the image beam IB to be transmitted to the eye EY to display a virtual image.

Moreover, the infrared light sources 310 and the image sensing module 320 is the same as those shown in FIGS. 20A and 20B, and the image display unit 111 may display the image of the veins sensed by the image sensing module 320.

In addition, the virtual image display system 300a may comprise the ambient light adjustment unit 140 (or the ambient light adjustment unit of aforementioned other embodiments).

Figure 22:
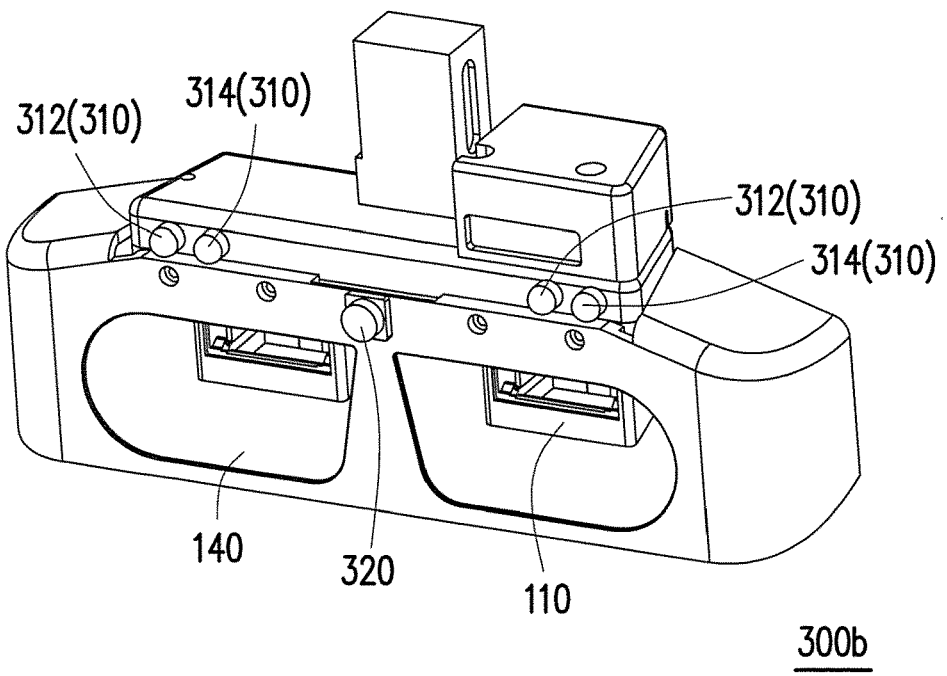
FIG. 22 is a schematic perspective view of a virtual image display system according to another embodiment of the disclosure.

FIG. 22 is a schematic perspective view of a virtual image display system according to another embodiment of the disclosure. Referring to FIG. 22, the virtual image display system 300b in this embodiment is similar to the virtual image display system 300a shown in FIG. 21B, and the difference therebetween is as follows. In this embodiment, the infrared light sources 310 are disposed at two opposite sides of the image sensing module 320.

Figure 23:
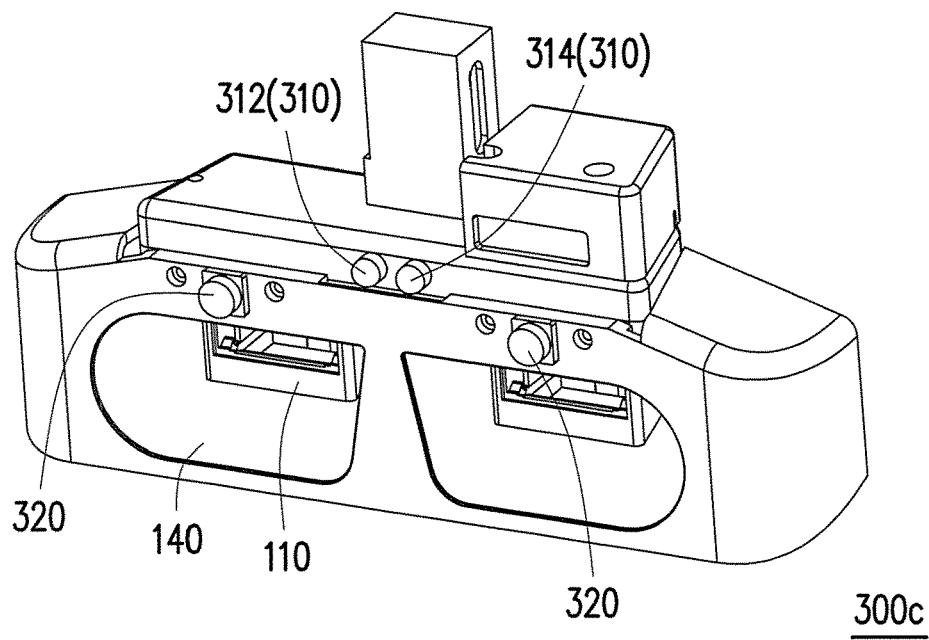
FIG. 23 is a schematic perspective view of a virtual image display system according to another embodiment of the disclosure.

FIG. 23 is a schematic perspective view of a virtual image display system according to another embodiment of the disclosure. Referring to FIG. 23, the virtual image display system 300c in this embodiment is similar to the virtual image display system 300b shown in FIG. 22, and the difference therebetween is as follows. In this embodiment, the virtual image display system 300c comprises two image sensing modules 320 configured to sense a three-dimensional image of the tissue, and the virtual image display system 300c comprises two virtual image display modules 110 (as shown in FIG. 4 or aforementioned other embodiments) configured to display the three-dimensional image of the tissue. In this embodiment, the infrared light sources 310 may be disposed between the two image sensing modules 320.

Figure 24:
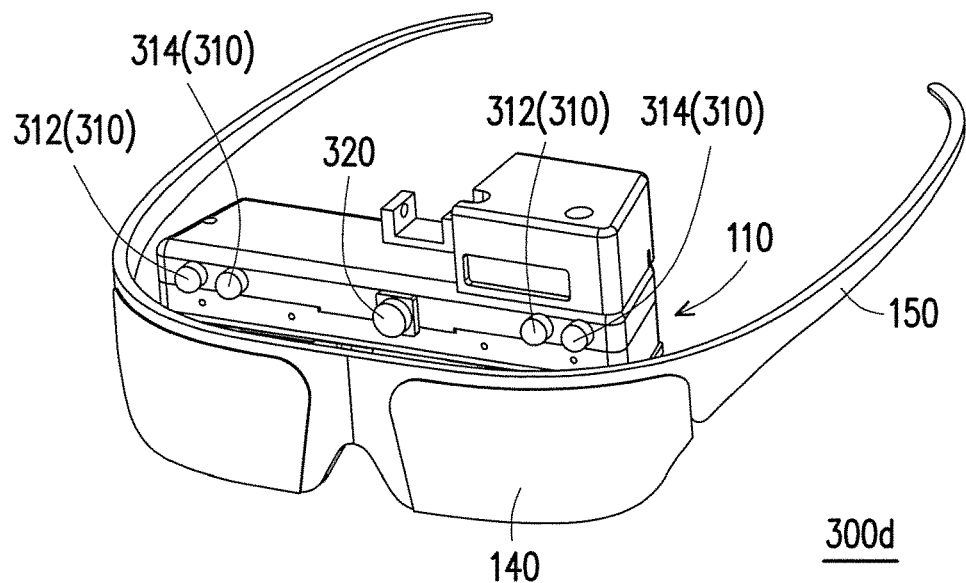
FIG. 24 is a schematic perspective view of a virtual image display system according to another embodiment of the disclosure.

FIG. 24 is a schematic perspective view of a virtual image display system according to another embodiment of the disclosure. Referring to FIG. 24, the virtual image display system 300d in this embodiment is similar to the virtual image display system 300b shown in FIG. 22, and the difference therebetween is as follows. In this embodiment, the virtual image display system 300d comprises a spectacle frame 150, wherein the virtual image display module 110, the infrared light source 310, and the image sensing module 320 are disposed on the spectacle frame 150. Moreover, the ambient light adjustment units 140 may be disposed on the spectacle frame 150, which is similar to the embodiment of FIG. 9B.

Figure 25:
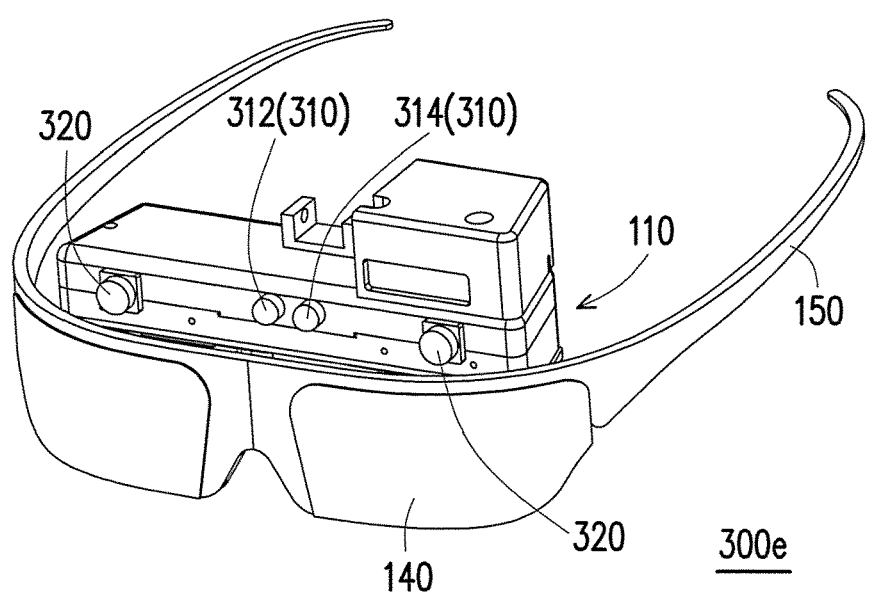
FIG. 25 is a schematic perspective view of a virtual image display system according to another embodiment of the disclosure.

FIG. 25 is a schematic perspective view of a virtual image display system according to another embodiment of the disclosure. Referring to FIG. 25, the virtual image display system 300e in this embodiment is similar to the virtual image display system 300c shown in FIG. 23, and the difference therebetween is as follows. In this embodiment, the virtual image display system 300e comprises a spectacle frame 150, wherein the virtual image display module 110, the infrared light source 310, and the image sensing module 320 are disposed on the spectacle frame 150. Moreover, the ambient light adjustment units 140 may be disposed on the spectacle frame 150, which is similar to the embodiment of FIG. 9B.

Figure 26A:
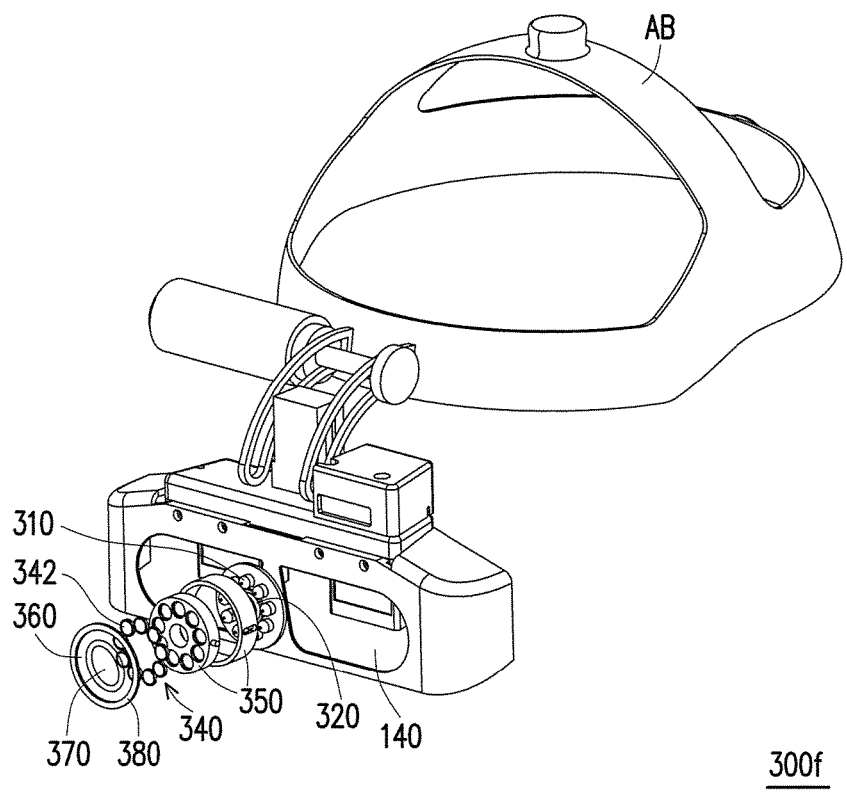
FIG. 26A is a schematic exploded view of a virtual image display system according to another embodiment of the disclosure.
Figure 26B:
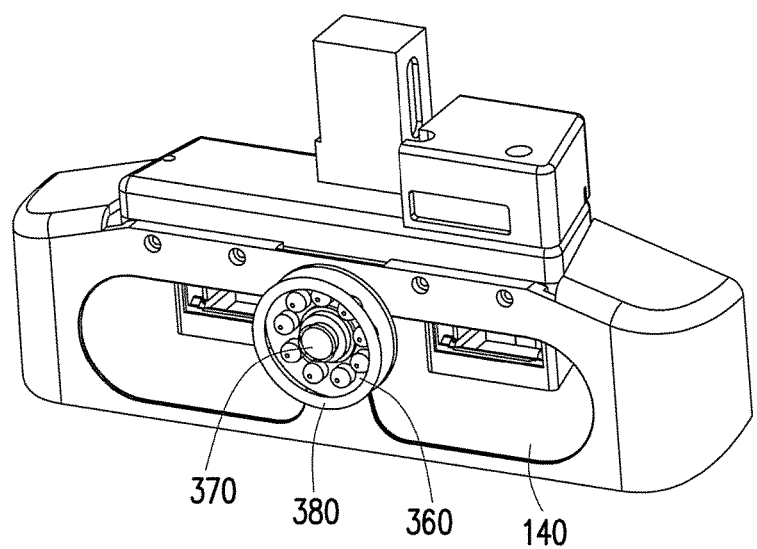
FIG. 26B is a schematic perspective view showing the first polarizer, the second polarizer, the transmission axis adjustment mechanism, the microstructure optical element, and the divergence angle adjustment mechanism in FIG. 26A assembled in front of the infrared light source and the image sensing module.

FIG. 26A is a schematic exploded view of a virtual image display system according to another embodiment of the disclosure. FIG. 26B is a schematic perspective view showing the first polarizer, the second polarizer, the transmission axis adjustment mechanism, the microstructure optical element, and the divergence angle adjustment mechanism in FIG. 26A assembled in front of the infrared light source and the image sensing module. Referring to FIGS. 26A and 26B, the virtual image display system 300f in this embodiment is similar to the virtual image display system 300a in FIG. 21A, and the main difference therebetween is as follows. In this embodiment, the virtual image display system 300f further includes a microstructure optical element 340 disposed in front of the infrared light source 310 and configured to control a light divergence angle of the infrared light emitted from the infrared light source 310. In this embodiment, the microstructure optical element 340 includes a plurality of microlenses 342, the microlenses 342 may be arranged in a ring. However, in other embodiments, the microlenses 342 may be arranged in an array or arranged in other forms.

In this embodiment, the virtual image display system 300f further includes a divergence angle adjustment mechanism 350 connected to the microstructure optical element 340 and configured to adjust a distance between the infrared light source 310 and the microstructure optical element 340. In this embodiment, the divergence angle adjustment mechanism 350 may be any appropriate mechanism capable of adjusting the distance between the infrared light source 310 and the microstructure optical element 340.

Figure 27A:
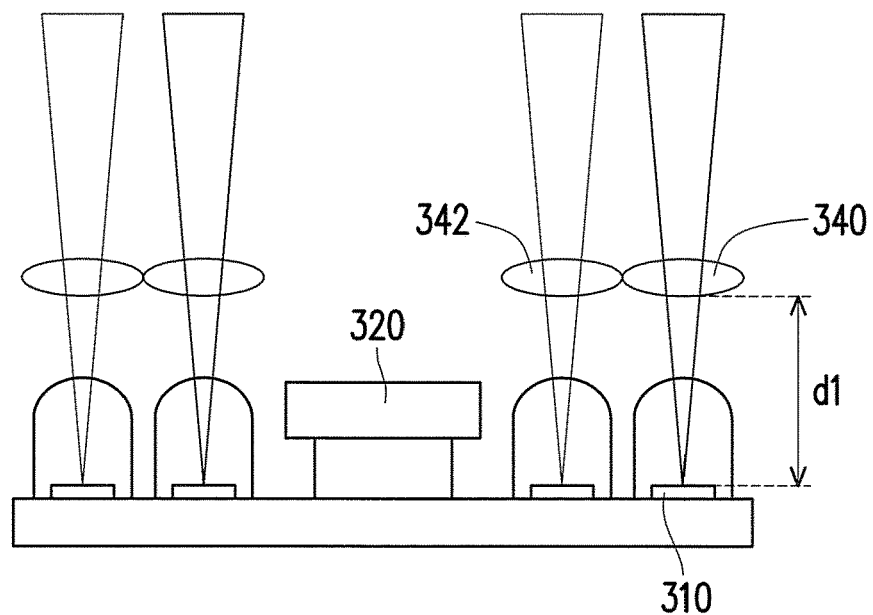
FIG. 27A is a schematic cross-sectional view showing the distance between the infrared light source and the microstructure optical element in FIG. 26A is larger.
Figure 27B:
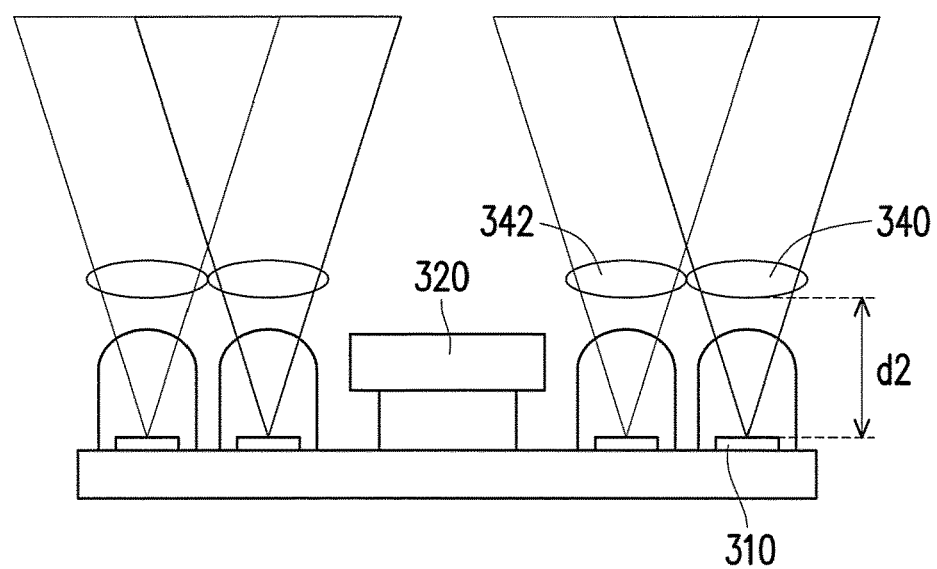
FIG. 27B is a schematic cross-sectional view showing the distance between the infrared light source and the microstructure optical element in FIG. 26A is smaller.

FIG. 27A is a schematic cross-sectional view showing the distance between the infrared light source and the microstructure optical element in FIG. 26A is larger, and FIG. 27B is a schematic cross-sectional view showing the distance between the infrared light source and the microstructure optical element in FIG. 26A is smaller. Referring to FIG. 27A, when a user adjusts the distance between the light-emitting chip of the infrared light source 310 and the microstructure optical element 340 to a larger value d1 through the divergence angle adjustment mechanism 350, the divergence angle of the infrared light emerging from the microstructure optical element 340 is smaller, wherein the value d1 is, for example, about the focal length of the microstructure optical element 340. As a result, the virtual image display system 300f may detect the vein of a person in a larger distance from the infrared light source 310.

In addition, referring to FIG. 27B, when the user adjusts the distance between the light-emitting chip of the infrared light source 310 and the microstructure optical element 340 to a smaller value d2 through the divergence angle adjustment mechanism 350, the divergence angle of the infrared light emerging from the microstructure optical element 340 is larger, wherein the value d2 is, for example, less than the focal length of the microstructure optical element 340. As a result, the virtual image display system 300f may detect the vein of a person in a smaller distance from the infrared light source 310.

Figure 28:
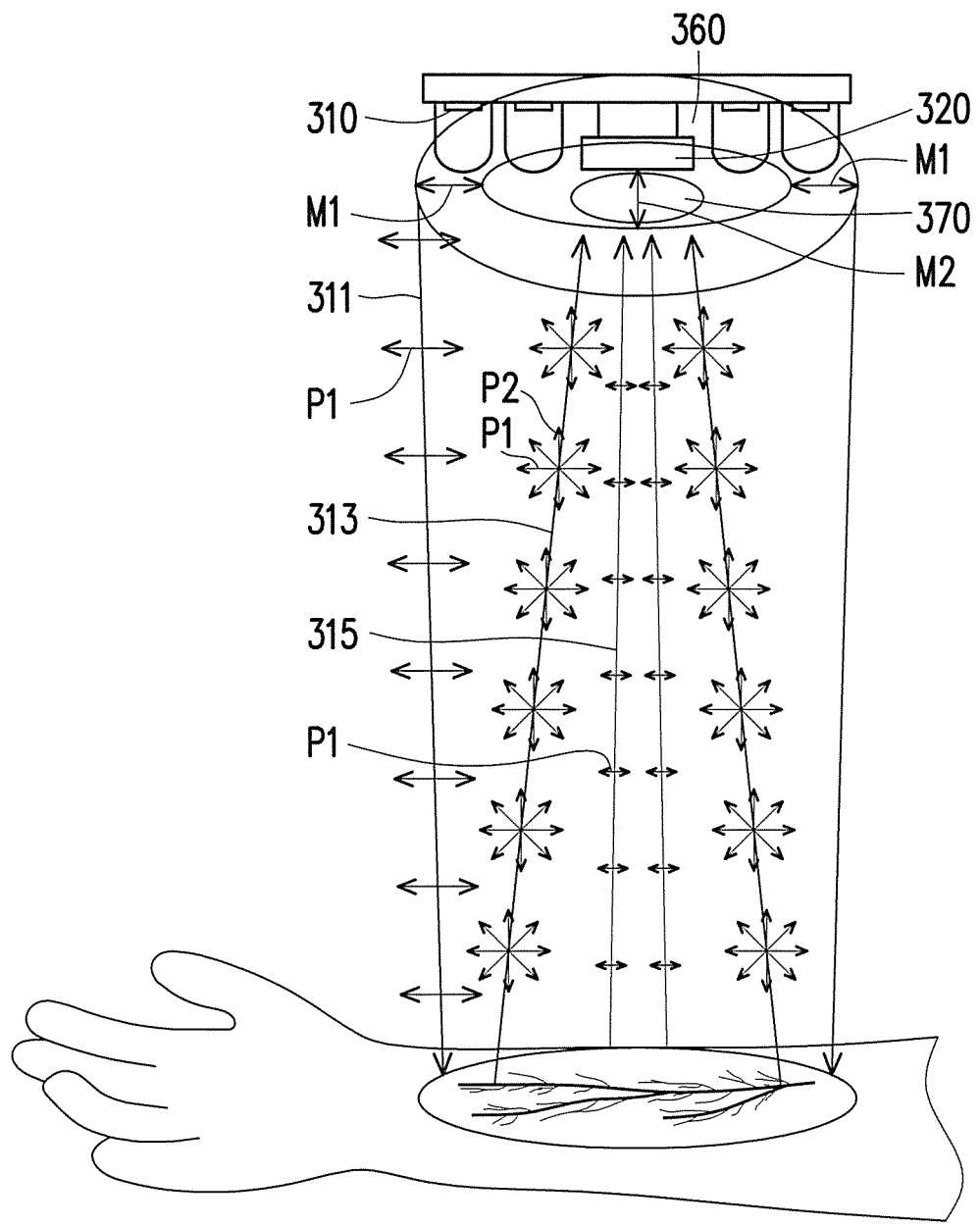
FIG. 28 is a schematic view showing the first polarizer and the second polarizer shown in FIG. 26A and the polarization directions of the infrared light.

FIG. 28 is a schematic view showing the first polarizer and the second polarizer shown in FIG. 26A and the polarization directions of the infrared light. Referring to FIGS. 26A, 26B, and 28, in this embodiment, the virtual image display system 300f further includes a first polarizer 360 and a second polarizer 370. The first polarizer 360 is disposed in front of the infrared light source 310 and configured to allow at least a part of the infrared light 311 having a first polarization direction P1 from the infrared light source 310 to pass through. The transmission axis M1 of the first polarizer 360 is substantially parallel to the first polarization direction P1. The second polarizer 370 is disposed in front of the image sensing module 320 and configured to allow a part of the infrared light 313 having a second polarization direction P2 from the tissue to pass through and be transmitted to the image sensing module 320.

Specifically, when a part of the infrared light 311 having the first polarization direction P1 strikes the skin of the person above the tissue, the skin reflects the infrared light 311 into an infrared light 315 having the first polarization direction P1. The second polarizer 370 has a transmission axis M2 substantially perpendicular to the first polarization direction, for example, so that the second polarizer 370 blocks the infrared light 315. Consequently, the infrared light 311 reflected by the skin is unable to be transmitted to the image sensing module 320.

On the other hand, when another part of the infrared light 311 having the first polarization direction P1 penetrates the skin and is transmitted to the tissue under the skin, the tissue containing the vein scatters the infrared light 311 to form an unpolarized infrared light 313. The unpolarized infrared light 313 is transmitted to the second polarizer 370, and the second polarizer 370 allows a part of the unpolarized infrared light 313 having the second polarization direction P2 to pass through and to be transmitted to the image sensing module 320, wherein the second polarization direction P2 is substantially parallel to the transmission axis M2.

Since the image sensing module 320 receives the part of the infrared light 313 from the tissue containing the vein and does not receive the infrared light 315 reflected by the skin, the image sensing module 320 can detect the image of the vein without being interfered with by the infrared light 315 reflected by the skin. Therefore, the contrast of the image of the vein is increased.

In this embodiment, the virtual image display system 300f further includes at least one transmission axis adjustment mechanism 380 (one transmission axis adjustment mechanism 380 is exemplarily shown in FIGS. 26A and 26B) connected to at least one of the first polarizer 360 and the second polarizer 370, and configured to adjust at least one transmission axes M1, M2 of the first polarizer 360 and the second polarizer 370. In this embodiment, the transmission axis adjustment mechanism 380 is, for example, a ring connected to the second polarizer 370 through the first polarizer 360. The user may rotate the ring to rotate the first polarizer 360 and the second polarizer 370, so as to rotate the transmission axes M1 and M2. In this embodiment, the transmission axis M1 is substantially perpendicular to the transmission axis M2. When using the virtual image display system 300f to see the image of the vein, the user may rotate the transmission axis adjustment mechanism 380 to find an image having an enough or largest contrast.

Figure 29A:
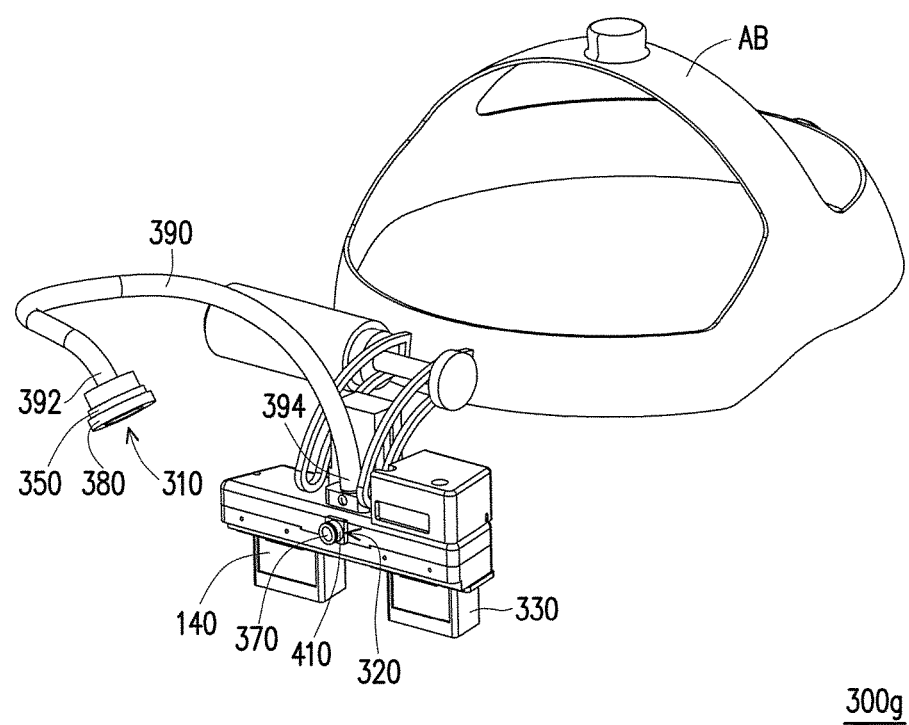
FIG. 29A is a schematic perspective view of a virtual image display system according to another embodiment of the disclosure.
Figure 29B:
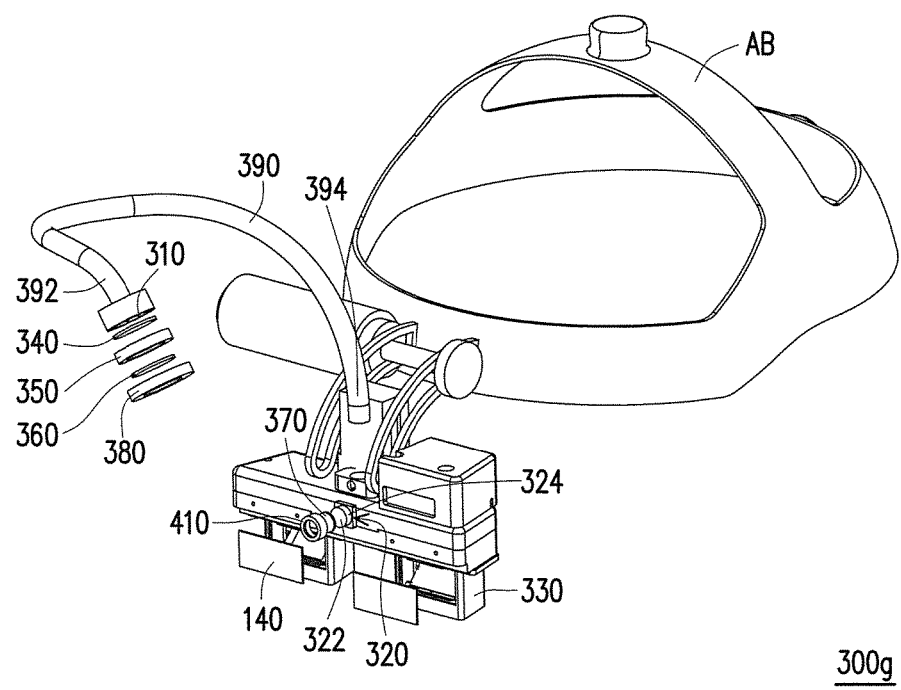
FIG. 29B is a schematic exploded view of the virtual image display in FIG. 29A.

FIG. 29A is a schematic perspective view of a virtual image display system according to another embodiment of the disclosure, and FIG. 29B is a schematic exploded view of the virtual image display in FIG. 29A. Referring to FIGS. 29A and 29B, the virtual image display system 300g in this embodiment is similar to the virtual image display system 300f in FIG. 26A, and the main difference therebetween is as follows. In this embodiment, the virtual image display system 300g further includes a flexible tube 390, wherein the infrared light source 310 is connected to a first end 392 of the flexible tube 390, and a second end 394 of the flexible tube 390 is connected to the virtual image display module 330. In this embodiment, the microstructure optical element 340, the divergence angle adjustment mechanism 350, the first polarizer 360, and the transmission axis adjustment mechanism 380 are also disposed in front of the infrared light source 310 and connected to the first end 392 of the flexible tube 390. The flexible tube 390 may be bent freely by the user, so that the infrared light source 310 may be adjusted to an appropriate position to irradiate the tissue containing the vein.

In this embodiment, the image sensing module 320 may include a lens 322 and a filter 324 disposed between the lens 322 and an image sensor of the image sensing module 320, wherein the image sensor may be a charge coupled device (CCD) or a complementary metal oxide semiconductor (CMOS) image sensor. The filter 324 is, for example, capable of allowing infrared to pass through and blocking visible light.

In this embodiment, the second polarizer 370 is disposed in front of the image sensing module 320, and another transmission axis adjustment mechanism 410 is connected to the second polarizer 370 and configured to adjust the transmission axis M2 of the second polarizer 370. Moreover, the transmission axis adjustment mechanism 380 is connected to the first polarizer 360 and configured to adjust the transmission axis M1 of the first polarizer 360. When using the virtual image display system 300g to detect the vein, the user may adjust the transmission axis adjustment mechanisms 380 and 410 to obtain the image of the vein with an enough or largest contrast.

In another embodiment, the first polarizer 360, the transmission axis adjustment mechanism 380, the second polarizer 370, and the transmission axis adjustment mechanism 410 may be removed from the virtual image display system 300g to form a new embodiment of the virtual image display system, or the microstructure optical element 340 and the divergence angle adjustment mechanism 350 may be further removed to form another new embodiment of the virtual image display system.

Figure 30:
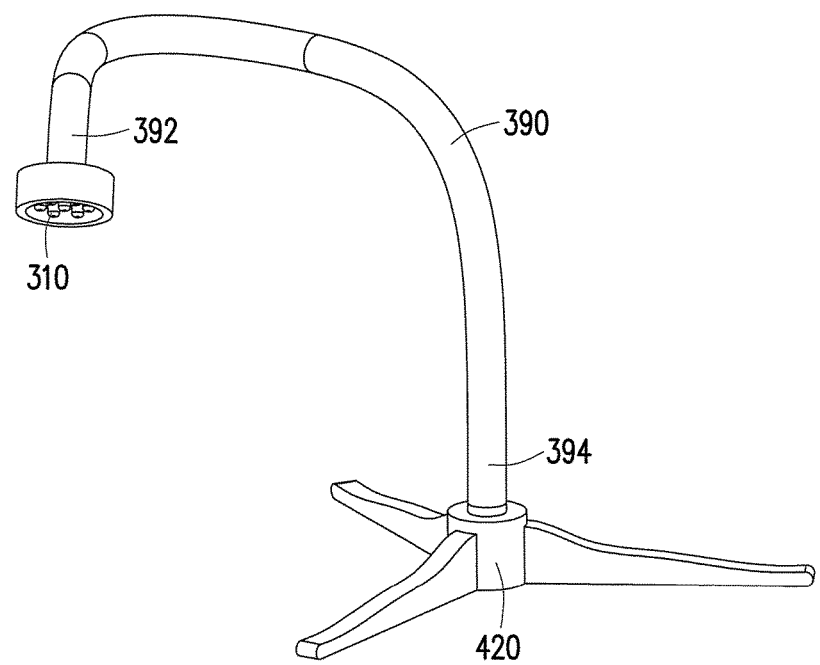
FIG. 30 is a schematic perspective view showing that the infrared light source and the flexible tube in FIG. 29A is separate from the virtual image display module in an virtual image display system according to another embodiment of the disclosure.

FIG. 30 is a schematic perspective view showing that the infrared light source and the flexible tube in FIG. 29A is separate from the virtual image display module in an virtual image display system according to another embodiment of the disclosure. Referring to FIG. 30, the virtual image display system in this embodiment is similar to the virtual image display system 300g in FIG. 29A, and the main difference therebetween is as follows. In this embodiment, the second end 394 of the flexible tube 390 is connected to a base 420 but not connected to the virtual image display module 330 as shown in FIG. 29B. The base 420 is, for example, a stand to support the flexible tube 390 and the infrared light source 310. The first polarizer 360, the transmission axis adjustment mechanism 380, the microstructure optical element 340, and the divergence angle adjustment mechanism 350 may also be connected to the first end 392 of the flexible tube 390 in an embodiment.

Figure 31:
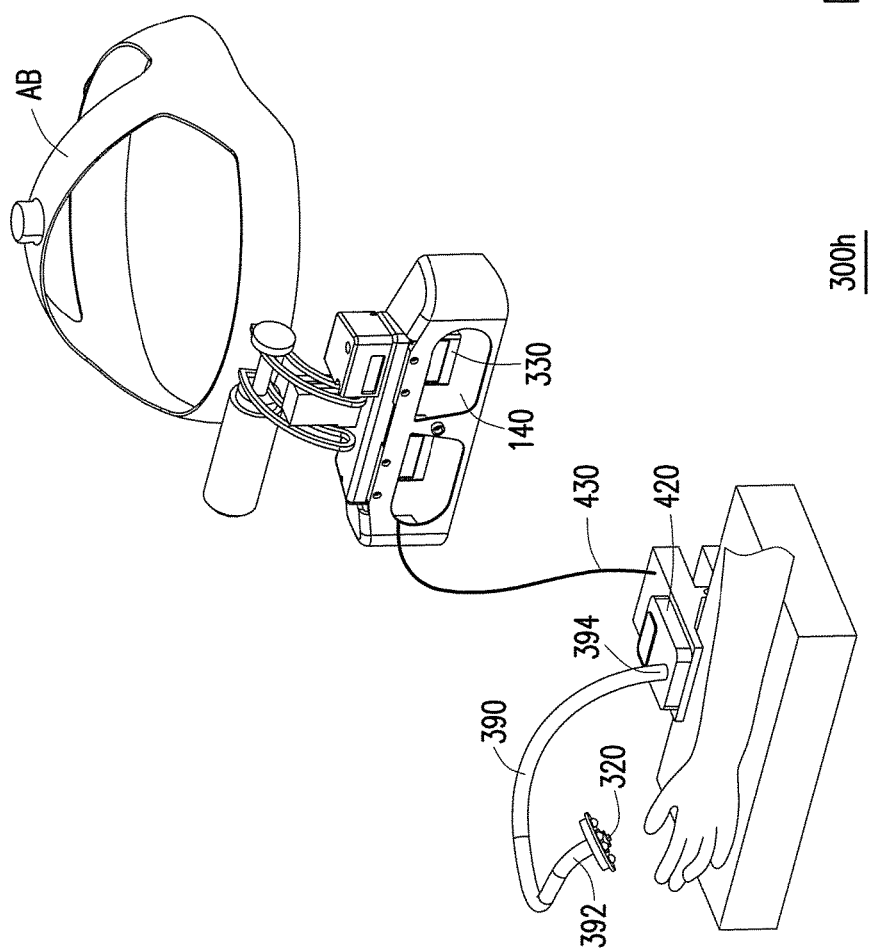
FIG. 31 is a schematic perspective view of a virtual image display system according to another embodiment of the disclosure.

FIG. 31 is a schematic perspective view of a virtual image display system according to another embodiment of the disclosure. Referring to FIG. 31, the virtual image display system 300h in this embodiment is similar to the virtual image display system in the embodiment of FIG. 30, and the main difference therebetween is as follows. In the virtual image display system 300h according to this embodiment, the image sensing module 320 is also connected to the first end 392 of the flexible tube 390, so that the image sensing module 320 may detect the vein of the user in a shorter distance, wherein the base 420 supporting the flexible tube 390 may be disposed on a table where a hand of the user is put. Moreover, the signal of the image sensing module 320 may be transmitted to the virtual image display module 330 by an electric wire 430 or wirelessly.

Based on the above, the virtual image display system of the embodiments of the disclosure allows the user to observe the physical image in front of the virtual image display system and the virtual image to be displayed by the image beam provided by the image display unit at the same time through the disposition of the image display unit and the beam splitting unit of the virtual image display module. The user can also make the virtual image and the physical image be displayed independently or on top of one another in front of the eye according to actual need. Moreover, the virtual image display system can also adjust the brightness or the area size of at least a part of the object beam to achieve the function of adjusting the image contrast and the ratio of area size of the virtual image and the physical image. Moreover, the virtual image display system can achieve the effect of maintaining good image quality and visual compensation through the overall optical design of the virtual image display module. Moreover, since the virtual image display system of the embodiments of the disclosure is lightweight and convenient to wear, the surgeon can freely adjust the viewing angle during surgery to monitor the surgical screen, and therefore an additional monitor is not needed and the surgeon does not need to stare at the same viewing angle for long periods of time. As a result, the cost of the instrument is lowered and fatigue to the eyes, the neck, and the shoulders and physical burden of the surgeon are reduced. Moreover, for less-experienced surgeons, the virtual image display system of the embodiments of the disclosure can help to control of the sense of direction of surgical devices, therefore facilitating learning and proficiency of surgical techniques, and thereby shortening the time of surgical training. Moreover, the virtual image display system of the embodiments of the disclosure is easy to operate, and therefore the operating time of long surgeries can be reduced and the risk of surgery is also reduced. In the virtual image display system according to the embodiment of the disclosure, the infrared light source may emit infrared light to illuminate the vein in the tissue, and the image sensing module may sense the infrared image of the vein, and the virtual image display module may form the virtual image of the vein viewed by the eye of the user. As a result, the user (e.g. a nurse or a doctor) may be easy to find the vein of a person (e.g. a patient) and perform venipuncture. Therefore, the possibility of success of performing venipuncture is effectively improved.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A virtual image display system adapted for venipuncture applications, the virtual image display system comprising:
   at least one infrared light source configured to emit at least one infrared light to a tissue having a vein;

at least one image sensing module configured to receive the infrared light from the tissue so as to sense an image of the vein;

a microstructure optical element disposed in front of the infrared light source and configured to control a light divergence angle of the infrared light;

a divergence angle adjustment mechanism connected to the microstructure optical element and configured to adjust a distance between the infrared light source and the microstructure optical element; and at least one virtual image display module disposed in front of at least one eye of a user, the at least one virtual image display module comprising:
an image display unit configured to show an image of the vein to the at least one eye of the user.

2. The virtual image display system of claim 1, wherein the at least one infrared light source is a plurality of infrared light sources surrounding the image sensing module.

3. The virtual image display system of claim 1, wherein the at least one infrared light source is a plurality of infrared light sources configured to emit infrared lights having at least two wavelengths.

4. The virtual image display system of claim 1, wherein the at least one image sensing module comprises two image sensing modules configured to sense a three-dimensional image of the tissue, and the at least one virtual image display module are two virtual image display modules configured to display the three-dimensional image of the tissue.

5. The virtual image display system of claim 1, wherein the image sensing module comprises a fixed focus lens or a zoom lens.

6. The virtual image display system of claim 1 further comprising a spectacle frame, wherein the virtual image display module, the infrared light source, and the image sensing module are disposed on the spectacle frame.

7. The virtual image display system of claim 1 further comprising a headband connected to the virtual image display module, the infrared light source, and the image sensing module.

8. The virtual image display system of claim 1 further comprising:
a first polarizer disposed in front of the infrared light source and configured to allow at least a part of the infrared light having a first polarization direction from the infrared light source to pass through; and
a second polarizer disposed in front of the image sensing module and configured to allow a part of the infrared light having a second polarization direction from the tissue to pass through and be transmitted to the image sensing module.

9. The virtual image display system of claim 8 further comprising at least one transmission axis adjustment mechanism connected to at least one of the first polarizer and the second polarizer, and configured to adjust at least one transmission axes of the first polarizer and the second polarizer.

10. The virtual image display system of claim 1 further comprising a flexible tube, wherein the infrared light source is connected to a first end of the flexible tube, and a second end of the flexible tube is connected to the virtual image display module or to a base.

11. The virtual image display system of claim 10, wherein the image sensing module is connected to the first end of the flexible tube.

12. The virtual image display system of claim 1, wherein the image display unit is configured to provide an image beam, and the at least one virtual image display module further comprises a beam splitting unit disposed on transmission paths of the image beam and an object beam from an environment object, the beam splitting unit causing at least a part of the object beam to be transmitted to the eye, and the beam splitting unit causing at least a part of the image beam to be transmitted to the eye to display a virtual image.

13. The virtual image display system of claim 12 being adapted for medical surgical applications, with which a surgical device is operated, wherein the image beam comprises at least one type of surgical information.

14. The virtual image display system of claim 12, further comprising an ambient light adjustment unit located on the transmission path of the object beam for adjusting a ratio of a brightness of the at least a part of the object beam to a brightness of the at least a part of the image beam.

15. The virtual image display system of claim 14, wherein the ambient light adjustment unit comprises at least one of at least one filter, a polarizer, a shutter, and a photochromic lens for adjusting the brightness of the at least a part of the object beam reflected to the eye and forming a blocking area of the object beam.

16. The virtual image display system of claim 15, wherein the at least one filter is a plurality of filters, a part of the filters have different sizes, and the user selects one of the filters to switch a size of the blocking area of the object beam.

17. The virtual image display system of claim 14, further comprising a control storage module electrically connected to the virtual image display module, the control storage module comprising:
a storage unit for storing the at least one type of surgical information; and
a control unit controlling the ambient light adjustment unit to adjust an ambient light, controlling the storage unit to adjust an output of the surgical information, and controlling a switching of an imaging position and a size of an image frame of the virtual image.

18. The virtual image display system of claim 17, wherein the ambient light adjustment unit comprises a liquid crystal unit for adjusting the brightness or a polarization state of the at least a part of the object beam passing through a partial area of the liquid crystal unit and forming a blocking area of the object beam in the eye.

19. The virtual image display system of claim 18, wherein the control unit adjusts a range of the partial area of the liquid crystal unit to switch the size of the blocking area of the object beam.

* * * * *